(12) United States Patent
Mercanzini et al.

(10) Patent No.: US 9,440,082 B2
(45) Date of Patent: *Sep. 13, 2016

(54) MICROFABRICATED NEUROSTIMULATION DEVICE

(71) Applicant: ECOLE POLYTECHNIQUE FEDERALE DE LAUSANNE, Lausanne (CH)

(72) Inventors: Andre Mercanzini, Renens (CH); Philippe Renaud, Preverenges (CH)

(73) Assignee: ECOLE POLYTECHNIQUE FEDERALE DE LAUSANNE, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/309,491

(22) Filed: Jun. 19, 2014

(65) Prior Publication Data

US 2014/0303703 A1 Oct. 9, 2014

Related U.S. Application Data

(63) Continuation of application No. 13/128,821, filed as application No. PCT/IB2009/007715 on Nov. 12, 2009, now Pat. No. 8,788,064.

(60) Provisional application No. 61/113,912, filed on Nov. 12, 2008.

(51) Int. Cl.
*A61N 1/37* (2006.01)
*A61N 1/05* (2006.01)
(Continued)

(52) U.S. Cl.
CPC ......... *A61N 1/37205* (2013.01); *A61B 5/6868* (2013.01); *A61N 1/0529* (2013.01); *A61N 1/0531* (2013.01); *A61N 1/0534* (2013.01); *Y10T 29/49117* (2015.01)

(58) Field of Classification Search
CPC ............ A61B 5/04001; A61B 5/0478; A61B 5/6868; A61B 5/4064; A61B 2018/00434; A61N 1/0529; A61N 1/0534; A61N 1/0531; A61N 1/372; A61N 1/37205
USPC ........................ 607/2, 45, 116; 600/378, 544
See application file for complete search history.

(56) References Cited

U.S. PATENT DOCUMENTS

| 4,245,645 A | 1/1981 | Arseneault et al. |
| 4,550,733 A | 11/1985 | Liss et al. |

(Continued)

FOREIGN PATENT DOCUMENTS

| EP | 0 677 743 | 10/1995 |
| EP | 0 743 839 | 11/1996 |

(Continued)

OTHER PUBLICATIONS

Communication from the European Patent Office in Application No. 09795810.2 dated Sep. 14, 2011.
(Continued)

*Primary Examiner* — Christopher A Flory
(74) *Attorney, Agent, or Firm* — James De Vellis; Foley & Lardner LLP

(57) ABSTRACT

Described herein are microelectrode array devices, and methods of fabrication and use of the same, to provide highly localized and efficient electrical stimulation of a neurological target. The device includes multiple microelectrode elements arranged along an elongated probe shaft. The microelectrode elements are dimensioned and shaped so as to target individual neurons, groups of neurons, and neural tissue as may be located in an animal nervous system, such as deep within a human brain. Beneficially, the neurological probe can be used to facilitate location of the neurological target and remain implanted for long-term monitoring and/or stimulation.

21 Claims, 45 Drawing Sheets

(51) Int. Cl.
  *A61B 5/00* (2006.01)
  *A61N 1/372* (2006.01)

(56) References Cited

U.S. PATENT DOCUMENTS

| | | | |
|---|---|---|---|
| 4,837,049 A | 6/1989 | Byers et al. | |
| 4,917,093 A | 4/1990 | Dufresne et al. | |
| 4,928,297 A | 5/1990 | Tsutsui et al. | |
| 4,969,468 A | 11/1990 | Byers et al. | |
| 4,989,617 A | 2/1991 | Memberg et al. | |
| 5,215,088 A | 6/1993 | Normann et al. | |
| 5,391,250 A | 2/1995 | Cheney et al. | |
| 5,400,784 A | 3/1995 | Durand et al. | |
| 5,419,777 A | 5/1995 | Hofling | |
| 5,496,369 A | 3/1996 | Howard, III | |
| 5,628,317 A | 5/1997 | Starkebaum et al. | |
| 5,643,330 A | 7/1997 | Holsheimer et al. | |
| 5,679,355 A | 10/1997 | Alexander et al. | |
| 5,683,422 A | 11/1997 | Rise | |
| 5,697,651 A | 12/1997 | Fernandes | |
| 5,697,975 A | 12/1997 | Howard et al. | |
| 5,702,429 A | 12/1997 | King | |
| 5,713,922 A | 2/1998 | King | |
| 5,713,923 A | 2/1998 | Ward et al. | |
| 5,716,377 A | 2/1998 | Rise et al. | |
| 5,727,552 A | 3/1998 | Ryan | |
| 5,752,979 A | 5/1998 | Benabid | |
| 5,755,759 A | 5/1998 | Cogan | |
| 5,782,798 A | 7/1998 | Rise | |
| 5,792,186 A | 8/1998 | Rise | |
| 5,797,970 A | 8/1998 | Pouvreau | |
| 5,800,474 A | 9/1998 | Benabid et al. | |
| 5,800,535 A | 9/1998 | Howard, III | |
| 5,814,092 A | 9/1998 | King | |
| 5,824,029 A | 10/1998 | Weijand et al. | |
| 5,833,709 A | 11/1998 | Rise et al. | |
| 5,833,714 A | 11/1998 | Loeb | |
| 5,843,148 A | 12/1998 | Gijsbers et al. | |
| 5,893,883 A | 4/1999 | Torgerson et al. | |
| 5,913,882 A | 6/1999 | King | |
| 5,921,924 A | 7/1999 | Avitall | |
| 5,927,277 A | 7/1999 | Baudino et al. | |
| 5,941,906 A | 8/1999 | Barreras et al. | |
| 5,957,958 A | 9/1999 | Schulman et al. | |
| 5,975,085 A | 11/1999 | Rise | |
| 5,978,702 A | 11/1999 | Ward et al. | |
| 5,991,668 A | 11/1999 | Leinders et al. | |
| 6,011,996 A | 1/2000 | Gielen et al. | |
| 6,018,682 A | 1/2000 | Rise | |
| 6,024,095 A | 2/2000 | Stanley, III | |
| 6,033,403 A * | 3/2000 | Tu | A61B 18/1492 606/41 |
| 6,038,480 A | 3/2000 | Hrdlicka et al. | |
| 6,050,992 A | 4/2000 | Nichols | |
| 6,094,598 A * | 7/2000 | Elsberry et al. | 607/116 |
| 6,104,960 A | 8/2000 | Duysens et al. | |
| 6,109,269 A | 8/2000 | Rise et al. | |
| 6,125,300 A | 9/2000 | Weijand et al. | |
| 6,128,537 A | 10/2000 | Rise | |
| 6,129,685 A * | 10/2000 | Howard, III | 600/585 |
| 6,161,047 A | 12/2000 | King et al. | |
| 6,205,359 B1 | 3/2001 | Boveja | |
| 6,205,361 B1 | 3/2001 | Kuzma et al. | |
| 6,216,043 B1 | 4/2001 | Swanson et al. | |
| 6,227,203 B1 * | 5/2001 | Rise et al. | 128/898 |
| 6,253,109 B1 | 6/2001 | Gielen | |
| 6,253,110 B1 | 6/2001 | Brabec et al. | |
| 6,263,237 B1 | 7/2001 | Rise | |
| 6,266,564 B1 | 7/2001 | Hill et al. | |
| 6,295,476 B1 | 9/2001 | Schaenzer | |
| 6,319,241 B1 | 11/2001 | King et al. | |
| 6,330,466 B1 | 12/2001 | Hofmann et al. | |
| 6,337,997 B1 | 1/2002 | Rise | |
| 6,343,226 B1 * | 1/2002 | Sunde et al. | 600/378 |
| 6,353,762 B1 | 3/2002 | Baudino et al. | |
| 6,356,784 B1 | 3/2002 | Lozano et al. | |
| 6,356,786 B1 | 3/2002 | Rezai et al. | |
| 6,356,787 B1 | 3/2002 | Rezai et al. | |
| 6,364,875 B1 | 4/2002 | Stanley, III | |
| 6,366,813 B1 | 4/2002 | DiLorenzo | |
| 6,374,140 B1 | 4/2002 | Rise | |
| 6,375,666 B1 | 4/2002 | Mische | |
| 6,379,353 B1 | 4/2002 | Nichols | |
| 6,415,187 B1 | 7/2002 | Kuzma et al. | |
| 6,434,431 B1 | 8/2002 | Camps et al. | |
| 6,479,999 B1 | 11/2002 | DeMeester et al. | |
| 6,484,059 B2 | 11/2002 | Gielen | |
| 6,493,590 B1 * | 12/2002 | Wessman | A61N 1/0534 607/116 |
| 6,529,774 B1 * | 3/2003 | Greene | 600/545 |
| 6,538,443 B2 | 3/2003 | Morich et al. | |
| 6,549,812 B1 | 4/2003 | Smits | |
| 6,556,873 B1 | 4/2003 | Smits | |
| 6,560,472 B2 | 5/2003 | Hill et al. | |
| 6,560,486 B1 | 5/2003 | Osorio et al. | |
| 6,587,733 B1 | 7/2003 | Cross et al. | |
| 6,591,128 B1 | 7/2003 | Wu et al. | |
| 6,594,524 B2 | 7/2003 | Esteller et al. | |
| 6,597,953 B2 | 7/2003 | Boling | |
| 6,643,552 B2 | 11/2003 | Edell et al. | |
| 6,671,544 B2 | 12/2003 | Baudino | |
| 6,675,046 B2 | 1/2004 | Holsheimer | |
| 6,687,538 B1 | 2/2004 | Hrdlicka et al. | |
| 6,690,973 B2 | 2/2004 | Hill et al. | |
| 6,708,064 B2 | 3/2004 | Rezai | |
| 6,718,208 B2 | 4/2004 | Hill et al. | |
| 6,718,211 B2 | 4/2004 | Smits | |
| 6,741,893 B2 | 5/2004 | Smits | |
| 6,745,079 B2 | 6/2004 | King | |
| 6,757,970 B1 * | 7/2004 | Kuzma et al. | 29/847 |
| 6,795,737 B2 | 9/2004 | Gielen et al. | |
| 6,804,552 B2 | 10/2004 | Thompson et al. | |
| 6,818,396 B1 | 11/2004 | Bloch et al. | |
| 6,829,498 B2 | 12/2004 | Kipke et al. | |
| 6,850,802 B2 | 2/2005 | Holsheimer | |
| 6,871,098 B2 | 3/2005 | Nuttin et al. | |
| 6,882,881 B1 | 4/2005 | Lesser et al. | |
| 6,892,097 B2 | 5/2005 | Holsheimer | |
| 6,892,438 B1 | 5/2005 | Hill et al. | |
| 6,904,306 B1 | 6/2005 | Wu et al. | |
| 6,909,920 B2 | 6/2005 | Lokhoff et al. | |
| 6,920,359 B2 | 7/2005 | Meadows et al. | |
| 6,928,320 B2 | 8/2005 | King | |
| 6,950,706 B2 | 9/2005 | Rodriguez et al. | |
| 6,950,709 B2 | 9/2005 | Baudino | |
| 6,978,171 B2 | 12/2005 | Goetz et al. | |
| 6,978,178 B2 | 12/2005 | Sommer et al. | |
| 6,999,819 B2 | 2/2006 | Swoyer et al. | |
| 7,006,859 B1 | 2/2006 | Osorio et al. | |
| 7,010,351 B2 | 3/2006 | Firlik et al. | |
| 7,010,356 B2 | 3/2006 | Jog et al. | |
| 7,024,246 B2 | 4/2006 | Acosta et al. | |
| 7,035,690 B2 | 4/2006 | Goetz | |
| 7,047,082 B1 * | 5/2006 | Schrom et al. | 607/116 |
| 7,047,084 B2 | 5/2006 | Erickson et al. | |
| 7,050,856 B2 | 5/2006 | Stypulkowski | |
| 7,051,419 B2 * | 5/2006 | Schrom et al. | 29/594 |
| 7,061,240 B2 | 6/2006 | Ham et al. | |
| 7,063,767 B1 | 6/2006 | Tyson et al. | |
| 7,076,292 B2 | 7/2006 | Forsberg | |
| 7,077,822 B1 * | 7/2006 | Howard, III | 604/93.01 |
| 7,107,104 B2 | 9/2006 | Keravel et al. | |
| 7,133,718 B2 | 11/2006 | Bakken et al. | |
| 7,146,222 B2 * | 12/2006 | Boling | 607/116 |
| 7,151,961 B1 | 12/2006 | Whitehurst et al. | |
| 7,174,219 B2 | 2/2007 | Wahlstrand et al. | |
| 7,177,701 B1 * | 2/2007 | Pianca | 607/116 |
| 7,181,288 B1 | 2/2007 | Rezai et al. | |
| 7,184,829 B2 | 2/2007 | Hill et al. | |
| 7,187,978 B2 | 3/2007 | Malek et al. | |
| 7,191,016 B2 | 3/2007 | Marshall et al. | |
| 7,191,018 B2 | 3/2007 | Gielen et al. | |
| 7,200,439 B2 | 4/2007 | Zdeblick et al. | |
| 7,203,548 B2 | 4/2007 | Whitehurst et al. | |

(56) References Cited

U.S. PATENT DOCUMENTS

| | | | |
|---|---|---|---|
| 7,204,798 | B2 | 4/2007 | Zdeblick et al. |
| 7,204,833 | B1 | 4/2007 | Osorio et al. |
| 7,209,787 | B2 | 4/2007 | DiLorenzo |
| 7,212,851 | B2 | 5/2007 | Donoghue et al. |
| 7,212,867 | B2 | 5/2007 | Van Venroo |
| 7,214,189 | B2 | 5/2007 | Zdeblick |
| 7,216,000 | B2 | 5/2007 | Sieracki et al. |
| 7,216,001 | B2 | 5/2007 | Hacker et al. |
| 7,231,256 | B2 | 6/2007 | Wahlstrand et al. |
| 7,236,822 | B2 | 6/2007 | Dobak, III |
| 7,242,984 | B2 | 7/2007 | DiLorenzo |
| 7,276,061 | B2 * | 10/2007 | Schaer ............... A61B 18/1492 607/41 |
| 7,280,867 | B2 | 10/2007 | Frei et al. |
| 7,282,030 | B2 | 10/2007 | Frei et al. |
| 7,282,050 | B2 | 10/2007 | Starkebaum et al. |
| 7,286,878 | B2 | 10/2007 | Stypulkowski |
| 7,286,882 | B2 | 10/2007 | Cole |
| 7,288,066 | B2 | 10/2007 | Drew |
| 7,289,851 | B2 | 10/2007 | Gunderson et al. |
| 7,289,852 | B2 | 10/2007 | Helfinstine et al. |
| 7,295,880 | B2 | 11/2007 | Gielen |
| 7,298,143 | B2 | 11/2007 | Jaermann et al. |
| 7,307,223 | B2 | 12/2007 | Tyson et al. |
| 7,313,430 | B2 | 12/2007 | Urquhart et al. |
| 7,313,440 | B2 | 12/2007 | Miesel |
| 7,315,759 | B2 | 1/2008 | Markowitz et al. |
| 7,317,947 | B2 | 1/2008 | Wahlstrand et al. |
| 7,317,948 | B1 | 1/2008 | King et al. |
| 7,319,899 | B2 | 1/2008 | Keizer |
| 7,319,904 | B2 | 1/2008 | Cross et al. |
| 7,321,798 | B2 | 1/2008 | Muhlenberg et al. |
| 7,321,837 | B2 | 1/2008 | Osorio et al. |
| 7,322,832 | B2 | 1/2008 | Kronich et al. |
| 7,328,057 | B2 | 2/2008 | Freas et al. |
| 7,328,068 | B2 | 2/2008 | Spinelli et al. |
| 7,328,069 | B2 | 2/2008 | Gerber |
| 7,330,760 | B2 | 2/2008 | Heruth et al. |
| 7,337,010 | B2 | 2/2008 | Howard et al. |
| 7,343,206 | B2 | 3/2008 | Sage et al. |
| 7,346,395 | B2 | 3/2008 | Lozano et al. |
| 7,356,369 | B2 | 4/2008 | Phillips et al. |
| 7,359,837 | B2 | 4/2008 | Drew |
| 7,366,572 | B2 | 4/2008 | Heruth et al. |
| 7,367,956 | B2 | 5/2008 | King |
| 7,369,891 | B2 | 5/2008 | Augustijn et al. |
| 7,369,893 | B2 | 5/2008 | Gunderson |
| 7,369,894 | B2 | 5/2008 | Gerber |
| 7,385,443 | B1 | 6/2008 | Denison |
| 7,388,378 | B2 | 6/2008 | Gray et al. |
| 7,389,147 | B2 | 6/2008 | Wahlstrand et al. |
| 7,390,311 | B2 | 6/2008 | Hildebrand et al. |
| 7,391,257 | B1 | 6/2008 | Denison et al. |
| 7,392,089 | B2 | 6/2008 | Wahlstrand et al. |
| 7,395,113 | B2 | 7/2008 | Heruth et al. |
| 7,400,927 | B1 | 7/2008 | Litvin |
| 7,406,351 | B2 | 7/2008 | Wesselink |
| 7,418,292 | B2 | 8/2008 | Shafer |
| 7,421,297 | B2 | 9/2008 | Giftakis et al. |
| 7,427,280 | B2 | 9/2008 | Gerber |
| 7,429,938 | B1 | 9/2008 | Corndorf |
| 7,433,734 | B2 | 10/2008 | King |
| 7,442,183 | B2 | 10/2008 | Baudino et al. |
| 7,447,545 | B2 | 11/2008 | Heruth et al. |
| 7,450,996 | B2 | 11/2008 | MacDonald et al. |
| 7,463,917 | B2 | 12/2008 | Martinez |
| 7,463,928 | B2 | 12/2008 | Lee et al. |
| 7,474,247 | B1 | 1/2009 | Heinks et al. |
| 7,479,910 | B1 | 1/2009 | Heinks et al. |
| 7,483,748 | B2 | 1/2009 | Torgerson et al. |
| 7,489,966 | B2 | 2/2009 | Leinders et al. |
| 7,489,970 | B2 | 2/2009 | Lee et al. |
| 7,491,181 | B2 | 2/2009 | Heruth et al. |
| 7,497,844 | B2 | 3/2009 | Spear et al. |
| 7,497,863 | B2 | 3/2009 | Solar et al. |
| 7,502,217 | B2 | 3/2009 | Zhao et al. |
| 7,505,815 | B2 | 3/2009 | Lee et al. |
| 7,505,869 | B2 | 3/2009 | Hartlaub |
| 7,515,961 | B2 | 4/2009 | Germanson et al. |
| 7,519,431 | B2 | 4/2009 | Goetz et al. |
| 7,519,432 | B2 | 4/2009 | Bolea et al. |
| 7,520,890 | B2 * | 4/2009 | Phillips .................... A61F 2/07 623/1.13 |
| 7,526,339 | B2 | 4/2009 | Lahti et al. |
| 7,526,340 | B2 | 4/2009 | Drew |
| 7,526,341 | B2 | 4/2009 | Goetz et al. |
| 7,529,582 | B1 | 5/2009 | DiLorenzo |
| 7,529,586 | B2 | 5/2009 | Wahlstrand et al. |
| 7,542,803 | B2 | 6/2009 | Heruth et al. |
| 7,546,164 | B2 | 6/2009 | King |
| 7,546,166 | B2 | 6/2009 | Michels et al. |
| 7,548,775 | B2 | 6/2009 | Kipke et al. |
| 7,548,786 | B2 | 6/2009 | Lee et al. |
| 7,551,951 | B1 | 6/2009 | Osorio et al. |
| 7,551,960 | B2 | 6/2009 | Forsberg et al. |
| 7,555,345 | B2 | 6/2009 | Wahlstrand et al. |
| 7,561,921 | B2 | 7/2009 | Phillips et al. |
| 7,563,141 | B2 | 7/2009 | Alexander et al. |
| 7,563,541 | B2 | 7/2009 | Howard et al. |
| 7,578,819 | B2 | 8/2009 | Bleich et al. |
| 7,580,756 | B2 | 8/2009 | Schulte et al. |
| 7,582,387 | B2 | 9/2009 | Howard et al. |
| 7,590,451 | B2 | 9/2009 | Tronnes et al. |
| 7,590,453 | B2 | 9/2009 | Heruth et al. |
| 7,590,455 | B2 | 9/2009 | Heruth et al. |
| 7,591,970 | B2 | 9/2009 | Olson |
| 7,594,828 | B2 | 9/2009 | Alexander et al. |
| 7,594,889 | B2 | 9/2009 | St. Ores et al. |
| 7,596,399 | B2 | 9/2009 | Singhal et al. |
| 7,596,408 | B2 | 9/2009 | Singhal et al. |
| 7,596,415 | B2 | 9/2009 | Brabec et al. |
| 7,599,730 | B2 | 10/2009 | Hunter et al. |
| 7,603,161 | B2 | 10/2009 | Wurmfeld et al. |
| 7,603,177 | B2 | 10/2009 | Sieracki et al. |
| 7,604,629 | B2 | 10/2009 | Gerber et al. |
| 7,604,644 | B2 | 10/2009 | Schulte et al. |
| 7,608,458 | B2 | 10/2009 | Soykan et al. |
| 7,610,083 | B2 | 10/2009 | Drew et al. |
| 7,611,483 | B2 | 11/2009 | Gerber et al. |
| 7,614,743 | B2 | 11/2009 | Geiger |
| 7,615,015 | B2 | 11/2009 | Coleman |
| 7,616,998 | B2 | 11/2009 | Nuttin et al. |
| 7,617,002 | B2 | 11/2009 | Goetz |
| 7,620,454 | B2 | 11/2009 | Dinsmoor et al. |
| 7,622,303 | B2 | 11/2009 | Soykan et al. |
| 7,622,988 | B2 | 11/2009 | Denison et al. |
| 7,623,053 | B2 | 11/2009 | Terry et al. |
| 7,623,918 | B2 | 11/2009 | Goetz |
| 7,623,919 | B2 | 11/2009 | Goetz et al. |
| 7,623,923 | B2 | 11/2009 | Gerber et al. |
| 7,623,930 | B2 | 11/2009 | Zeijlemaker et al. |
| 7,624,293 | B2 | 11/2009 | Osorio et al. |
| 7,628,780 | B2 | 12/2009 | Bonner et al. |
| 7,631,415 | B2 | 12/2009 | Phillips et al. |
| 7,632,225 | B2 | 12/2009 | Stypulkowski |
| 7,635,541 | B2 | 12/2009 | Scott et al. |
| 7,637,867 | B2 | 12/2009 | Zdeblick |
| 7,640,059 | B2 | 12/2009 | Forsberg et al. |
| 7,640,060 | B2 | 12/2009 | Zdeblick |
| 7,641,992 | B2 | 1/2010 | Howard et al. |
| 7,642,013 | B2 | 1/2010 | Howard et al. |
| 7,647,111 | B2 | 1/2010 | Ries et al. |
| 7,647,116 | B2 | 1/2010 | Bauhahn |
| 7,647,117 | B2 | 1/2010 | Bauhahn |
| 7,647,121 | B2 | 1/2010 | Wahlstrand et al. |
| 7,650,291 | B2 | 1/2010 | Rosenfeld et al. |
| 7,653,433 | B2 | 1/2010 | Lozano et al. |
| 7,657,318 | B2 | 2/2010 | King et al. |
| 7,657,319 | B2 | 2/2010 | Goetz et al. |
| 7,660,620 | B2 | 2/2010 | Zeijlemaker et al. |
| 7,660,630 | B2 | 2/2010 | Dudding et al. |
| 7,662,140 | B2 | 2/2010 | Heruth et al. |
| 7,662,509 | B2 | 2/2010 | Howard et al. |
| 7,663,066 | B2 | 2/2010 | Tyson et al. |

(56) References Cited

U.S. PATENT DOCUMENTS

| | | | |
|---|---|---|---|
| 7,664,551 B2 | 2/2010 | Cigaina |
| 7,664,552 B2 | 2/2010 | Wahlstrand et al. |
| 7,668,601 B2 | 2/2010 | Hegland et al. |
| 7,671,594 B2 | 3/2010 | Gray |
| 7,676,271 B2 | 3/2010 | Wahlstrand et al. |
| 7,676,273 B2 | 3/2010 | Goetz et al. |
| 7,676,274 B2 | 3/2010 | Hung et al. |
| 7,680,540 B2 | 3/2010 | Jensen et al. |
| 7,682,355 B2 | 3/2010 | Gerber et al. |
| 7,682,745 B2 | 3/2010 | Howard et al. |
| 7,684,860 B2 | 3/2010 | Wahlstrand et al. |
| 7,684,873 B2 | 3/2010 | Gerber |
| 7,689,289 B2 | 3/2010 | King |
| 7,697,972 B2 | 4/2010 | Verard et al. |
| 7,697,995 B2 | 4/2010 | Cross et al. |
| 7,706,124 B2 | 4/2010 | Zhao et al. |
| 7,706,889 B2 | 4/2010 | Gerber et al. |
| 7,711,421 B2 | 5/2010 | Shafer et al. |
| 7,711,428 B2 | 5/2010 | Janzig et al. |
| 7,711,436 B2 | 5/2010 | Stone |
| 7,713,194 B2 | 5/2010 | Zdeblick |
| 7,713,195 B2 | 5/2010 | Zdeblick |
| 7,720,548 B2 | 5/2010 | King |
| 7,729,768 B2 | 6/2010 | White et al. |
| 7,729,780 B2 | 6/2010 | Vardiman |
| 7,738,958 B2 | 6/2010 | Zdeblick et al. |
| 7,742,823 B2 | 6/2010 | King et al. |
| 7,756,588 B2 | 7/2010 | Jog et al. |
| 7,797,029 B2 | 9/2010 | Gibson et al. |
| 7,822,483 B2 | 10/2010 | Stone et al. |
| 7,853,303 B2 | 12/2010 | Nikumb et al. |
| 7,877,149 B2 | 1/2011 | Zdeblick |
| 7,899,539 B2 | 3/2011 | Whitehurst et al. |
| 7,925,329 B2 | 4/2011 | Zdeblick et al. |
| 7,930,035 B2 | 4/2011 | Dilorenzo |
| 7,935,056 B2 | 5/2011 | Zdeblick |
| 7,941,202 B2 | 5/2011 | Hetke et al. |
| 7,945,336 B2 | 5/2011 | Sauter-Starace et al. |
| 7,969,161 B2 | 6/2011 | Behzadi et al. |
| 7,974,705 B2 | 7/2011 | Zdeblick et al. |
| 7,978,064 B2 | 7/2011 | Zdeblick et al. |
| 7,979,105 B2 | 7/2011 | Kipke et al. |
| 7,983,751 B2 | 7/2011 | Zdeblick et al. |
| 8,000,794 B2 | 8/2011 | Lozano |
| 8,000,808 B2 | 8/2011 | Hegland et al. |
| 8,032,224 B2 | 10/2011 | Miesel et al. |
| 8,036,737 B2 | 10/2011 | Goetz et al. |
| 8,036,743 B2 | 10/2011 | Savage et al. |
| 8,036,748 B2 | 10/2011 | Zdeblick et al. |
| 8,055,334 B2 | 11/2011 | Savage et al. |
| 8,055,353 B2 | 11/2011 | Kreidler et al. |
| 8,099,170 B2 | 1/2012 | Jensen et al. |
| 8,114,021 B2 | 2/2012 | Robertson et al. |
| 8,115,618 B2 | 2/2012 | Robertson et al. |
| 8,121,687 B2 | 2/2012 | Jensen et al. |
| 8,123,684 B2 | 2/2012 | Zdeblick |
| 8,172,762 B2 | 5/2012 | Robertson |
| 8,187,161 B2 | 5/2012 | Li et al. |
| 8,195,308 B2 | 6/2012 | Frank et al. |
| 8,204,586 B2 | 6/2012 | Zdeblick |
| 8,258,962 B2 | 9/2012 | Robertson et al. |
| 8,261,428 B2 | 9/2012 | Fang et al. |
| 8,280,514 B2 | 10/2012 | Lozano et al. |
| 8,332,020 B2 | 12/2012 | Zdeblick |
| 8,355,768 B2 | 1/2013 | Masmanidis et al. |
| 8,412,347 B2 | 4/2013 | Zdeblick |
| 8,473,061 B2 | 6/2013 | Moffitt et al. |
| 8,473,069 B2 | 6/2013 | Bi et al. |
| 8,489,203 B2 | 7/2013 | Ortmann |
| 8,788,064 B2 * | 7/2014 | Mercanzini et al. ......... 607/116 |
| 8,874,232 B2 | 10/2014 | Chen |
| 8,897,891 B2 | 11/2014 | Romero |
| 8,938,308 B2 | 1/2015 | Meadows |
| 2002/0062143 A1 | 5/2002 | Baudino et al. |
| 2003/0004553 A1 | 1/2003 | Grill et al. |
| 2003/0023282 A1 | 1/2003 | Barrett et al. |
| 2003/0036780 A1 | 2/2003 | Barrett et al. |
| 2003/0060822 A1 * | 3/2003 | Schaer ............... A61B 18/1492 606/41 |
| 2003/0083724 A1 * | 5/2003 | Jog ....................... A61N 1/0536 607/122 |
| 2003/0100823 A1 * | 5/2003 | Kipke ................. A61B 5/04001 600/378 |
| 2003/0135253 A1 * | 7/2003 | Kokones et al. ............. 607/117 |
| 2003/0176892 A1 | 9/2003 | Shalev |
| 2004/0002635 A1 | 1/2004 | Hargrove et al. |
| 2004/0015205 A1 | 1/2004 | Whitehurst et al. |
| 2004/0039434 A1 * | 2/2004 | Schrom et al. ............... 607/118 |
| 2004/0102828 A1 | 5/2004 | Lowry et al. |
| 2004/0122335 A1 | 6/2004 | Sackellares et al. |
| 2004/0133390 A1 | 7/2004 | Osorio et al. |
| 2004/0138517 A1 | 7/2004 | Osorio et al. |
| 2004/0138536 A1 | 7/2004 | Frei et al. |
| 2004/0138720 A1 | 7/2004 | Naisberg et al. |
| 2004/0138722 A1 | 7/2004 | Carroll et al. |
| 2004/0152958 A1 | 8/2004 | Frei et al. |
| 2004/0172089 A1 | 9/2004 | Whitehurst et al. |
| 2004/0193021 A1 | 9/2004 | Zdeblick et al. |
| 2004/0215288 A1 | 10/2004 | Lee et al. |
| 2004/0220637 A1 | 11/2004 | Zdeblick et al. |
| 2004/0225335 A1 | 11/2004 | Whitehurst et al. |
| 2004/0243011 A1 | 12/2004 | Plaza |
| 2004/0249417 A1 | 12/2004 | Ransbury et al. |
| 2004/0254483 A1 | 12/2004 | Zdeblick et al. |
| 2005/0004627 A1 | 1/2005 | Gibson et al. |
| 2005/0008660 A1 | 1/2005 | Kipke et al. |
| 2005/0010261 A1 | 1/2005 | Luders et al. |
| 2005/0021103 A1 * | 1/2005 | DiLorenzo ...................... 607/45 |
| 2005/0027284 A1 | 2/2005 | Lozano et al. |
| 2005/0033136 A1 | 2/2005 | Govari et al. |
| 2005/0038489 A1 * | 2/2005 | Grill ............................. 607/116 |
| 2005/0049655 A1 | 3/2005 | Boveja et al. |
| 2005/0070971 A1 | 3/2005 | Fowler et al. |
| 2005/0075681 A1 | 4/2005 | Rezai et al. |
| 2005/0113882 A1 | 5/2005 | Cameron et al. |
| 2005/0137647 A1 | 6/2005 | Wallace et al. |
| 2005/0143790 A1 | 6/2005 | Kipke et al. |
| 2005/0154425 A1 | 7/2005 | Boveja et al. |
| 2005/0171558 A1 | 8/2005 | Abovitz et al. |
| 2005/0182455 A1 | 8/2005 | Thrope et al. |
| 2005/0209511 A1 | 9/2005 | Heruth et al. |
| 2005/0209513 A1 | 9/2005 | Heruth et al. |
| 2005/0209643 A1 | 9/2005 | Heruth et al. |
| 2005/0222642 A1 * | 10/2005 | Przybyszewski et al. ...... 607/48 |
| 2005/0240242 A1 | 10/2005 | DiLorenzo |
| 2005/0245988 A1 | 11/2005 | Miesel |
| 2006/0004422 A1 | 1/2006 | De Ridder |
| 2006/0030897 A1 | 2/2006 | Gilmer et al. |
| 2006/0041295 A1 * | 2/2006 | Osypka ........................ 607/117 |
| 2006/0049957 A1 | 3/2006 | Surgenor et al. |
| 2006/0058588 A1 | 3/2006 | Zdeblick |
| 2006/0058727 A1 | 3/2006 | Bernabei |
| 2006/0058855 A1 * | 3/2006 | Gill ............................... 607/45 |
| 2006/0095105 A1 * | 5/2006 | Jog ....................... A61N 1/0551 607/116 |
| 2006/0116581 A1 | 6/2006 | Zdeblick et al. |
| 2006/0129203 A1 * | 6/2006 | Garabedian .......... A61N 1/0531 607/45 |
| 2006/0135877 A1 | 6/2006 | Giftakis et al. |
| 2006/0149336 A1 * | 7/2006 | Meadows ....................... 607/45 |
| 2006/0149337 A1 | 7/2006 | John |
| 2006/0167497 A1 | 7/2006 | Armstrong et al. |
| 2006/0173263 A1 * | 8/2006 | He ..................... A61B 5/04001 600/378 |
| 2006/0173510 A1 | 8/2006 | Besio et al. |
| 2006/0178709 A1 | 8/2006 | Foster et al. |
| 2006/0195154 A1 | 8/2006 | Jaax et al. |
| 2006/0200206 A1 | 9/2006 | Firlik et al. |
| 2006/0212090 A1 | 9/2006 | Lozano et al. |
| 2006/0241717 A1 | 10/2006 | Whitehurst et al. |
| 2006/0258951 A1 | 11/2006 | Bleich et al. |
| 2006/0264777 A1 | 11/2006 | Drew |
| 2006/0276866 A1 | 12/2006 | McCreery |
| 2006/0282014 A1 | 12/2006 | Kipke et al. |

(56) References Cited

U.S. PATENT DOCUMENTS

| | | |
|---|---|---|
| 2006/0293720 A1 | 12/2006 | DiLorenzo |
| 2006/0293721 A1 | 12/2006 | Tarver et al. |
| 2007/0027498 A1 | 2/2007 | Maschino et al. |
| 2007/0027500 A1 | 2/2007 | Maschino et al. |
| 2007/0027514 A1 | 2/2007 | Gerber |
| 2007/0043268 A1 | 2/2007 | Russell |
| 2007/0060974 A1 | 3/2007 | Lozano |
| 2007/0067002 A1 | 3/2007 | Lozano |
| 2007/0067003 A1 | 3/2007 | Sanchez et al. |
| 2007/0088403 A1 | 4/2007 | Wyler et al. |
| 2007/0088404 A1 | 4/2007 | Wyler et al. |
| 2007/0093870 A1 | 4/2007 | Maschino |
| 2007/0100389 A1 | 5/2007 | Jaax et al. |
| 2007/0100392 A1 | 5/2007 | Maschino et al. |
| 2007/0100393 A1 | 5/2007 | Whitehurst et al. |
| 2007/0100398 A1 | 5/2007 | Sloan |
| 2007/0106143 A1 | 5/2007 | Flaherty |
| 2007/0123765 A1 | 5/2007 | Hetke et al. |
| 2007/0123944 A1 | 5/2007 | Zdeblick |
| 2007/0135721 A1 | 6/2007 | Zdeblick |
| 2007/0142872 A1 | 6/2007 | Mickle et al. |
| 2007/0150024 A1 | 6/2007 | Leyde et al. |
| 2007/0173890 A1 | 7/2007 | Armstrong |
| 2007/0173896 A1 | 7/2007 | Zdeblick |
| 2007/0173897 A1 | 7/2007 | Zdeblick |
| 2007/0173901 A1 | 7/2007 | Reeve |
| 2007/0173908 A1 | 7/2007 | Begnaud |
| 2007/0179558 A1 | 8/2007 | Gliner et al. |
| 2007/0179569 A1 | 8/2007 | Zdeblick |
| 2007/0185537 A1 | 8/2007 | Zdeblick |
| 2007/0185544 A1 | 8/2007 | Dawant et al. |
| 2007/0185548 A1 | 8/2007 | Zdeblick |
| 2007/0185549 A1 | 8/2007 | Zdeblick |
| 2007/0197892 A1 | 8/2007 | Shen et al. |
| 2007/0203537 A1 | 8/2007 | Goetz et al. |
| 2007/0203546 A1 | 8/2007 | Stone et al. |
| 2007/0208394 A1 | 9/2007 | King et al. |
| 2007/0213784 A1 | 9/2007 | Pless |
| 2007/0213785 A1 | 9/2007 | Osorio et al. |
| 2007/0213786 A1 | 9/2007 | Sackellares et al. |
| 2007/0219591 A1 | 9/2007 | Zdeblick et al. |
| 2007/0225674 A1 | 9/2007 | Molnar et al. |
| 2007/0225773 A1 | 9/2007 | Shen et al. |
| 2007/0225774 A1 | 9/2007 | Eskandar et al. |
| 2007/0233192 A1 | 10/2007 | Craig |
| 2007/0249953 A1 | 10/2007 | Frei et al. |
| 2007/0249954 A1 | 10/2007 | Virag et al. |
| 2007/0250133 A1 | 10/2007 | Carlson et al. |
| 2007/0255323 A1 | 11/2007 | Werder et al. |
| 2007/0255338 A1 | 11/2007 | Wahlstrand |
| 2007/0255374 A1 | 11/2007 | Kolafa et al. |
| 2007/0255531 A1 | 11/2007 | Drew |
| 2007/0265683 A1 | 11/2007 | Ehrlich |
| 2007/0282389 A1 | 12/2007 | Moxon et al. |
| 2007/0293908 A1 | 12/2007 | Cowan et al. |
| 2008/0021514 A1 | 1/2008 | Pless |
| 2008/0021517 A1 | 1/2008 | Dietrich |
| 2008/0027289 A1 | 1/2008 | Zdeblick |
| 2008/0027487 A1 | 1/2008 | Patel et al. |
| 2008/0027503 A1 | 1/2008 | Marrosu et al. |
| 2008/0027504 A1* | 1/2008 | Bedenbaugh .................... 607/45 |
| 2008/0027540 A1* | 1/2008 | Cumming .................... 623/6.37 |
| 2008/0039895 A1 | 2/2008 | Fowler et al. |
| 2008/0046012 A1 | 2/2008 | Covalin et al. |
| 2008/0046013 A1 | 2/2008 | Lozano |
| 2008/0058630 A1 | 3/2008 | Robertson |
| 2008/0077186 A1 | 3/2008 | Thompson et al. |
| 2008/0077191 A1 | 3/2008 | Morrell |
| 2008/0103547 A1 | 5/2008 | Okun et al. |
| 2008/0103548 A1 | 5/2008 | Fowler et al. |
| 2008/0103578 A1* | 5/2008 | Gerber .................... 607/149 |
| 2008/0114417 A1 | 5/2008 | Leyde |
| 2008/0119900 A1 | 5/2008 | DiLorenzo |
| 2008/0139870 A1 | 6/2008 | Gliner et al. |
| 2008/0140152 A1* | 6/2008 | Imran et al. .................... 607/46 |
| 2008/0154328 A1 | 6/2008 | Thompson et al. |
| 2008/0154331 A1 | 6/2008 | John et al. |
| 2008/0161881 A1* | 7/2008 | Firlik et al. .................... 607/45 |
| 2008/0161896 A1 | 7/2008 | Sauter-Starace et al. |
| 2008/0172103 A1 | 7/2008 | Kao et al. |
| 2008/0177196 A1* | 7/2008 | Burdick et al. ............... 600/544 |
| 2008/0188905 A1 | 8/2008 | Swartz |
| 2008/0195166 A1 | 8/2008 | Sun et al. |
| 2008/0195227 A1 | 8/2008 | Boling et al. |
| 2008/0208283 A1* | 8/2008 | Vetter et al. .................... 607/45 |
| 2008/0208287 A1 | 8/2008 | Palermo et al. |
| 2008/0215125 A1 | 9/2008 | Farah et al. |
| 2008/0221642 A1 | 9/2008 | Humayun et al. |
| 2008/0242976 A1 | 10/2008 | Robertson et al. |
| 2008/0255439 A1* | 10/2008 | Tang et al. .................... 600/373 |
| 2008/0255629 A1 | 10/2008 | Jenson et al. |
| 2008/0255647 A1 | 10/2008 | Jensen et al. |
| 2008/0269835 A1 | 10/2008 | Carlson et al. |
| 2008/0269842 A1 | 10/2008 | Giftakis et al. |
| 2008/0275526 A1* | 11/2008 | Lozano .................... 607/45 |
| 2008/0284599 A1 | 11/2008 | Zdeblick et al. |
| 2008/0294218 A1 | 11/2008 | Savage et al. |
| 2008/0300652 A1 | 12/2008 | Lim et al. |
| 2008/0306394 A1 | 12/2008 | Zdeblick et al. |
| 2008/0312726 A1 | 12/2008 | Frank et al. |
| 2008/0316020 A1 | 12/2008 | Robertson et al. |
| 2009/0027504 A1 | 1/2009 | Lim et al. |
| 2009/0062879 A1 | 3/2009 | Li et al. |
| 2009/0082645 A1 | 3/2009 | Hafezi et al. |
| 2009/0105784 A1 | 4/2009 | Massoud-Ansari et al. |
| 2009/0118806 A1 | 5/2009 | Vetter et al. |
| 2009/0132042 A1 | 5/2009 | Hetke et al. |
| 2009/0171416 A1 | 7/2009 | Firlik et al. |
| 2009/0177144 A1* | 7/2009 | Masmanidis et al. .......... 604/66 |
| 2009/0187196 A1 | 7/2009 | Vetter |
| 2009/0204183 A1 | 8/2009 | Kreidler et al. |
| 2009/0240314 A1 | 9/2009 | Kong et al. |
| 2009/0253977 A1 | 10/2009 | Kipke et al. |
| 2009/0256702 A1 | 10/2009 | Robertson et al. |
| 2009/0292325 A1* | 11/2009 | Cederna et al. .................... 607/2 |
| 2009/0299174 A1 | 12/2009 | Wright et al. |
| 2009/0306728 A1* | 12/2009 | Wright et al. .................... 607/3 |
| 2009/0306729 A1 | 12/2009 | Doerr |
| 2009/0312770 A1 | 12/2009 | Kozai et al. |
| 2009/0318824 A1 | 12/2009 | Nishida et al. |
| 2009/0325424 A1 | 12/2009 | Aarts et al. |
| 2010/0014541 A1 | 1/2010 | Harriman |
| 2010/0015274 A1 | 1/2010 | Fill |
| 2010/0030298 A1 | 2/2010 | Martens et al. |
| 2010/0036468 A1 | 2/2010 | Decre et al. |
| 2010/0069717 A1 | 3/2010 | Hafezi et al. |
| 2010/0076536 A1 | 3/2010 | Merz et al. |
| 2010/0087853 A1 | 4/2010 | Kipke et al. |
| 2010/0100152 A1 | 4/2010 | Martens et al. |
| 2010/0106178 A1* | 4/2010 | Obermiller ........ A61B 17/0057 606/194 |
| 2010/0114193 A1 | 5/2010 | Lozano et al. |
| 2010/0114234 A1 | 5/2010 | Zdeblick |
| 2010/0114250 A1 | 5/2010 | Zdeblick |
| 2010/0130844 A1 | 5/2010 | Williams et al. |
| 2010/0145216 A1 | 6/2010 | He et al. |
| 2010/0145414 A1 | 6/2010 | Decre et al. |
| 2010/0152747 A1 | 6/2010 | Padiy et al. |
| 2010/0198315 A1 | 8/2010 | Martens et al. |
| 2010/0249883 A1 | 9/2010 | Zdeblick |
| 2010/0274305 A1 | 10/2010 | Gliner et al. |
| 2010/0292602 A1 | 11/2010 | Worrell et al. |
| 2010/0298908 A1 | 11/2010 | Vardiman |
| 2010/0298917 A1 | 11/2010 | Vardiman |
| 2010/0298918 A1 | 11/2010 | Vardiman |
| 2010/0312188 A1 | 12/2010 | Robertson et al. |
| 2010/0312228 A1 | 12/2010 | Zdeblick et al. |
| 2010/0318163 A1 | 12/2010 | Zdeblick |
| 2010/0331807 A1 | 12/2010 | Whitehurst et al. |
| 2011/0001488 A1 | 1/2011 | Behzadi et al. |
| 2011/0022124 A1 | 1/2011 | Zdeblick et al. |
| 2011/0034964 A1 | 2/2011 | Bi et al. |
| 2011/0034970 A1 | 2/2011 | Barker |
| 2011/0040203 A1 | 2/2011 | Savage et al. |

(56) References Cited

U.S. PATENT DOCUMENTS

| | | |
|---|---|---|
| 2011/0071766 A1 | 3/2011 | Dolan et al. |
| 2011/0130809 A1 | 6/2011 | Zdeblick |
| 2011/0152988 A1 | 6/2011 | Whitehurst et al. |
| 2011/0154655 A1 | 6/2011 | Hetke et al. |
| 2011/0184495 A1 | 7/2011 | Wang et al. |
| 2011/0190860 A1 | 8/2011 | Harberts et al. |
| 2011/0196454 A1 | 8/2011 | Strand et al. |
| 2011/0208225 A1 | 8/2011 | Martens et al. |
| 2011/0213382 A1 | 9/2011 | Decre et al. |
| 2011/0218417 A1 | 9/2011 | Boogaard et al. |
| 2011/0224757 A1 | 9/2011 | Zdeblick et al. |
| 2011/0224765 A1 | 9/2011 | Harberts et al. |
| 2011/0224766 A1 | 9/2011 | Tol et al. |
| 2011/0282179 A1 | 11/2011 | Zdeblick |
| 2012/0004520 A1 | 1/2012 | Whitworth et al. |
| 2012/0004527 A1 | 1/2012 | Thompson et al. |
| 2012/0004716 A1 | 1/2012 | Langhammer et al. |
| 2012/0007734 A1 | 1/2012 | Berkman et al. |
| 2012/0022341 A1 | 1/2012 | Zdeblick |
| 2012/0035684 A1 | 2/2012 | Thompson et al. |
| 2012/0053344 A1 | 3/2012 | Lagos Gonzalez |
| 2012/0059444 A1 | 3/2012 | Pardoel et al. |
| 2012/0062379 A1 | 3/2012 | Hafezi et al. |
| 2012/0095355 A1 | 4/2012 | Zdeblick |
| 2012/0109262 A1 | 5/2012 | Martens |
| 2012/0109599 A1 | 5/2012 | Martens |
| 2012/0116188 A1 | 5/2012 | Frank et al. |
| 2012/0136420 A1 | 5/2012 | Pardoel et al. |
| 2012/0150256 A1 | 6/2012 | Martens |
| 2012/0184837 A1 | 7/2012 | Martens et al. |
| 2012/0253442 A1 | 10/2012 | Gliner et al. |
| 2012/0277821 A1 | 11/2012 | Martens et al. |
| 2012/0296444 A1 | 11/2012 | Greenberg et al. |
| 2012/0303088 A1 | 11/2012 | Van Kaam et al. |
| 2012/0303089 A1 | 11/2012 | Martens et al. |
| 2012/0303107 A1 | 11/2012 | Decre et al. |
| 2012/0316630 A1* | 12/2012 | Firlik et al. ............ 607/116 |
| 2013/0009691 A1 | 1/2013 | Blanken et al. |
| 2013/0030366 A1 | 1/2013 | Robertson et al. |
| 2013/0046356 A1 | 2/2013 | Jensen et al. |
| 2013/0060102 A1 | 3/2013 | Zdeblick |
| 2013/0085361 A1 | 4/2013 | Mercanzini et al. |
| 2013/0131754 A1 | 5/2013 | Sarvazyan |
| 2013/0144132 A1 | 6/2013 | Hafezi et al. |
| 2013/0172716 A1 | 7/2013 | Lozano et al. |
| 2013/0193950 A1 | 8/2013 | Hafezi et al. |
| 2013/0204318 A1 | 8/2013 | Young |
| 2013/0223028 A1 | 8/2013 | Arne et al. |
| 2013/0231188 A1 | 9/2013 | Berberich et al. |
| 2013/0282090 A1 | 10/2013 | Decre et al. |
| 2013/0345789 A1 | 12/2013 | Havel et al. |
| 2014/0039578 A1 | 2/2014 | Whitehurst et al. |

FOREIGN PATENT DOCUMENTS

| | | |
|---|---|---|
| EP | 0 892 654 | 1/1999 |
| EP | 0 895 483 | 2/1999 |
| EP | 0 959 942 | 12/1999 |
| EP | 1 048 319 | 11/2000 |
| EP | 1 062 973 | 12/2000 |
| EP | 1 102 607 | 5/2001 |
| EP | 1 257 320 | 11/2002 |
| EP | 1 446 189 | 8/2004 |
| EP | 1 514 576 | 3/2005 |
| EP | 1 750 798 | 2/2007 |
| EP | 1 890 764 | 2/2008 |
| EP | 1 931 419 | 6/2008 |
| EP | 1 985 579 | 10/2008 |
| EP | 1 993 665 | 11/2008 |
| EP | 2 046 441 | 4/2009 |
| EP | 2 066 396 B1 | 6/2009 |
| EP | 2 069 003 | 6/2009 |
| EP | 2 131 916 | 12/2009 |
| EP | 2 167 188 | 3/2010 |
| EP | 2 320 221 | 5/2011 |
| EP | 2 341 979 | 7/2011 |
| EP | 2 456 513 A1 | 5/2012 |
| EP | 2 542 303 A1 | 1/2013 |
| EP | 2 559 454 A1 | 2/2013 |
| EP | 2 604 313 | 6/2013 |
| EP | 2 620 179 A1 | 7/2013 |
| EP | 2 623 154 A1 | 8/2013 |
| EP | 2 626 108 A1 | 8/2013 |
| EP | 2 626 109 A1 | 8/2013 |
| EP | 2 626 110 A1 | 8/2013 |
| EP | 2 626 111 A1 | 8/2013 |
| EP | 2 656 875 A1 | 10/2013 |
| EP | 2 656 876 A1 | 10/2013 |
| EP | 2 674 193 A1 | 12/2013 |
| WO | WO-98/10010 | 3/1998 |
| WO | WO-03/022354 | 3/2003 |
| WO | WO-03/028521 | 4/2003 |
| WO | WO-03/066152 | 8/2003 |
| WO | WO-03/066153 A2 | 8/2003 |
| WO | WO-03/066157 | 8/2003 |
| WO | WO-2004/045707 | 6/2004 |
| WO | WO-2005/002467 | 1/2005 |
| WO | WO-2005/067792 | 7/2005 |
| WO | WO-2005/112216 | 11/2005 |
| WO | WO-2006/104432 | 10/2006 |
| WO | WO-2007/002144 | 1/2007 |
| WO | WO-2007/009070 | 1/2007 |
| WO | WO-2007/011611 | 1/2007 |
| WO | WO-2007/025356 | 3/2007 |
| WO | WO-2007/028003 A2 | 3/2007 |
| WO | WO-2007/042999 | 4/2007 |
| WO | WO-2007/092330 | 8/2007 |
| WO | WO-2007/100428 | 9/2007 |
| WO | WO-2007/108718 | 9/2007 |
| WO | WO-2008/003318 | 1/2008 |
| WO | WO-2008/005478 | 1/2008 |
| WO | WO-2008/016881 | 2/2008 |
| WO | WO-2008/035285 | 3/2008 |
| WO | WO-2008/035344 | 3/2008 |
| WO | WO-2008/051463 | 5/2008 |
| WO | WO-2008/064269 A2 | 5/2008 |
| WO | WO-2008/068759 | 6/2008 |
| WO | WO-2008/075294 | 6/2008 |
| WO | WO-2008/077440 | 7/2008 |
| WO | WO-2008/089726 | 7/2008 |
| WO | WO-2008/107822 | 9/2008 |
| WO | WO-2008/109298 | 9/2008 |
| WO | WO-2008/133616 | 11/2008 |
| WO | WO-2008/133683 | 11/2008 |
| WO | WO-2008/138305 | 11/2008 |
| WO | WO-2010/014686 | 2/2010 |
| WO | WO-2010/055421 | 5/2010 |
| WO | WO-2011/115999 | 9/2011 |
| WO | WO-2013/014206 | 1/2013 |

OTHER PUBLICATIONS

Decision of Rejection and Decision for Dismissal of Amendment in JP Patent Application No. 2011-543841 dated May 15, 2014.

Examination Report from European Patent Office in 09 795 810.2 dated May 8, 2014.

US Notice of Allowance in U.S. Appl. No. 13/128,821 dated Dec. 24, 2013.

US Notice of Allowance in U.S. Appl. No. 13/128,821 dated Mar. 25, 2014.

US Office Action in U.S. Appl. No. 13/128,821 dated Nov. 14, 2013.

U.S. Appl. No. 07/151,961, filed Feb. 3, 1988, Masahiko Okunuki et al.

Australian Patent Examination Report No. 1 dated Jan. 30, 2014 in corresponding Australian Application No. 2010326613, 2 pages.

Benabid, et al. "Combined (Thalamotomy and Stimulation) Stereotactic Surgery of the VIM Thalamic Nucleus for Bilateral Parkinson Disease", Proceedings of the Meeting of the American Society for Stereotactic and Functional Neurosurgery, Montreal 1987 Appl. Neurophysiol. 50: 344-346.

Canadian Office Action for Application No. 2,743,575 dated Sep. 25, 2014, 3 pages.

(56) References Cited

OTHER PUBLICATIONS

Cogan, Stuart F., et al. "Plasma-enhanced chemical vapor deposited silicon carbide as an implantable dielectric coating." Journal of Biomedical Materials Research Part A 67.3 (2003): 856-867.
EIC Biomedical, "Thin-film Encapsulation for Neural Recording and Stimulation Electrodes", Silicon carbide and oxycarbide, Apr. 2008: pp. 1-2.
European Search Report for Appl. Ser. No. 09803534.8 dated Jul. 21, 2011.
European Search Report for Appl. Ser. No. 13169272.5 dated Aug. 30, 2013.
European Search Report for application No. EP 14172592 dated Aug. 28, 2014, 8 pages.
Examination Report in AU Patent Application No. 2009276603 dated Mar. 3, 2014.
Examination report in AU Patent Application No. 2011234422 dated Feb. 11, 2014.
Examination Report in EP Patent Application No. 11 711 884.4 dated Mar. 28, 2014.
Fierce Medical Devices, "Medtronic Announces First U.S. Implant of World's Smallest, Minimally Invasive Cardiac Pacemaker", Feb. 20, 2014, pp. 1-3.
Gibney, "St. Jude places its Nanostim leadless pacemaker in a U.K. patient", Fierce Medical Devices, Jan. 27, 2014, pp. 1-3.
International Preliminary Report on Patentability for PCT/EP2010/068658 dated Jun. 5, 2012.
International Preliminary Report on Patentability for PCT/US2009/052077 dated Feb. 1, 2011.
International Search Report and Written Opinion for PCT/EP2010/068658 dated Mar. 21, 2011.
International Search Report and Written Opinion in Application No. PCT/EP2011/055045 dated Jul. 18, 2011.
International Search Report and Written Opinion in PCT/US09/52077 dated Sep. 25, 2009.
Notice of Allowance for U.S. Appl. No. 14/287,917 dated Apr. 15, 2015.
Notice of Reasons for Rejection in JP Patent Application No. 2011-521276 dated Mar. 3, 2014.
Notice of Reasons for Rejection in JP Patent Application No. 2011-521276 dated May 30, 2013.
Notice of Reasons for Rejections for Japanese Patent Appl. Ser. No. 2012-541491 dated Aug. 28, 2014, 8 pages.
Office Action for Canadian Appl. Ser. No. 2743575 dated Jan. 21, 2015 (4 pages).
Office Action for Canadian Appl. Ser. No. 2743575 dated Jun. 11, 2015.
Office Action for EPO Appl. Ser. No. 10787404.2 dated May 6, 2015.
Office Action for European Application No. 10787404.2 dated Mar. 26, 2013.
Office Action for Japanese Appl. Ser. No. 2013-501857 dated Jun. 1, 2015.
Office Action for Japanese Appl. Ser. No. 2013-501857 dated Sep. 17, 2014.
Pollak, et al. "Effets de la Stimulation du Noyau Sous-Thalamique Dans La Maladie De Parkinson", Rev. Neurol (Paris),149, 3, 175-176. Mason, Paris, 1993.
Second Notice of Reasons for Rejection for Japanese Application No. 2012-541491 mailed Apr. 8, 2015.
US Notice of Allowance for U.S. Appl. No. 14/316,154 dated Apr. 20, 2015.
US Notice of Allowance for U.S. Appl. No. 13/512,936 dated Feb. 20, 2014.
US Notice of Allowance for U.S. Appl. No. 13/512,936 dated Nov. 25, 2013.
US Notice of Allowance for U.S. Appl. No. 13/056,261 dated May 8, 2014.
US Office Action for U.S. Appl. No. 13/638,435 dated Jun. 30, 2015.
US Office Action for U.S. Appl. No. 13/638,435 dated Mar. 12, 2015.
US Office Action for U.S. Appl. No. 14/316,154 dated Dec. 18, 2014.
US Office Action for U.S. Appl. No. 13/512,936 dated Aug. 14, 2013.
US Office Action for U.S. Appl. No. 13/056,261 dated Jan. 9, 2014.
US Office Action in U.S. Appl. No. 13/056,261 dated Aug. 7, 2013.
US Office Action on U.S. Appl. No. 14/287,917 dated Sep. 26, 2014.
Written Opinion for PCT/EP2010/068658 dated Jun. 1, 2012.
Australian Patent Examination Report No. 1 dated Jan. 31, 2014 in corresponding Australian Application No. 2009315316, 3 pages.
English translation of Notice of Reasons for Rejection in JP application No. 2011-543841 dated Oct. 21, 2013.
European Communication and Search Report for Application No. 09795810.2 dated Sep. 25, 2013.
European Communication mailed May 22, 2013 including search report for EP application No. 12198290.4-1652.
Examination Report for EP09795810.2 dated Jun. 22, 2012.
International Preliminary Report on Patentability for PCT/IB2009/007715 dated May 17, 2011.
International Search Report for PCT/IB2009/007715 dated Apr. 22, 2010.
Notice of Reasons for Rejection for Japanese Patent Application No. 2011-543841 dated May 30, 2013.
Rousche, et al., "Flexible polyimide-based intracortical electrode arrays with bioactive capability," IEEE Transactions on Biomedical Engineering 48(3): 361-371 (Mar. 2001).
Sepulveda et al., "Finite Element Analysis of Current Pathways with Implanted Electrodes", J. Biomed. Eng. 1983, vol. 5, pp. 41-48.
US Office Action on U.S. Appl. No. 13/128,821 DTD Dec. 14, 2012.
US Office Action on U.S. Appl. No. 13/128,821 DTD Apr. 24, 2012.
Written Opinion for Singapore Application No. 201103393-3 dated May 2, 2012.
Written Opinion of the International Search Authority for PCT/IB2009/07715 dated May 12, 2011.
US Office Action for U.S. Appl. No. 14/470,423 dated Jan. 21, 2016.
Decision of Rejection for Japanese Appl. Ser. No. 2012-541491 dated Oct. 26, 2015.
International Search Report and Written Opinion for PCT Appl. Ser. No. PCT/IB2015/053610 dated Jul. 20, 2015.
International Search Report and Written Opinion for PCT Appl. Ser. No. PCT/IB2015/056437 dated Nov. 5, 2015.
International Search Report and Written Opinion for PCT Appl. Ser. No. PCT/IB2015/056438 dated Nov. 5, 2015.
Office Action for Canadian Appl. Ser. No. 2732309 dated Dec. 7, 2015.
Office Action for Canadian Appl. Ser. No. 2743575 dated Sep. 14, 2015.
Office Action for EPO Appl. Ser. No. 14172592.9 dated Aug. 20, 2015.
US Notice of Allowance for U.S. Appl. No. 14/287,917 dated Jul. 20, 2015.
US 8,388,533, 03/2013, Hafezi et al. (withdrawn)
US 8,469,885, 06/2013, Hafezi et al. (withdrawn)

* cited by examiner

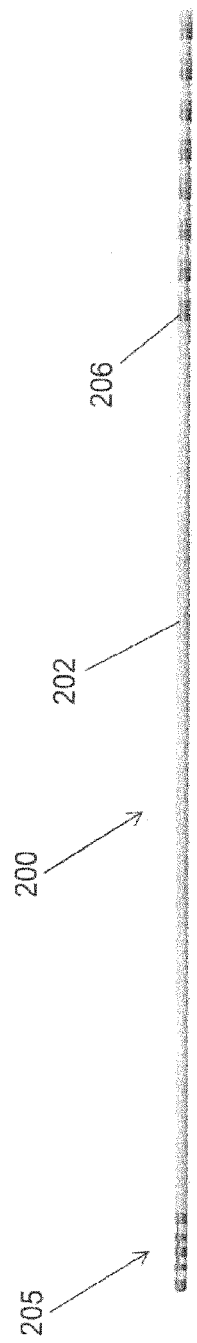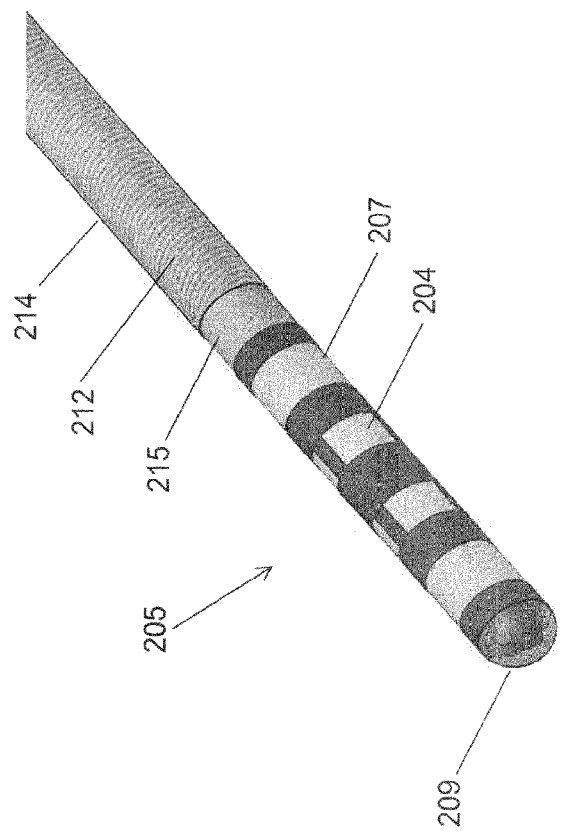

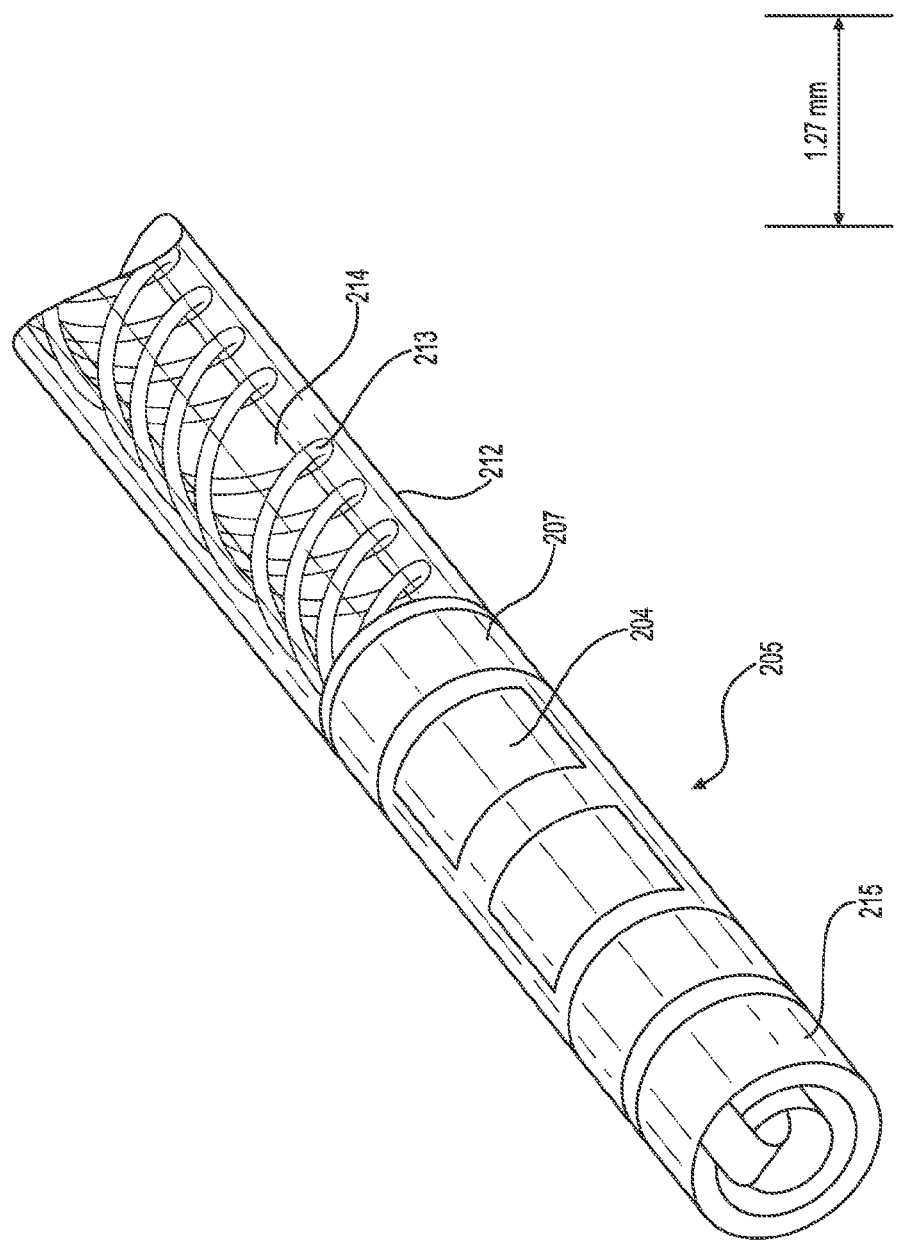

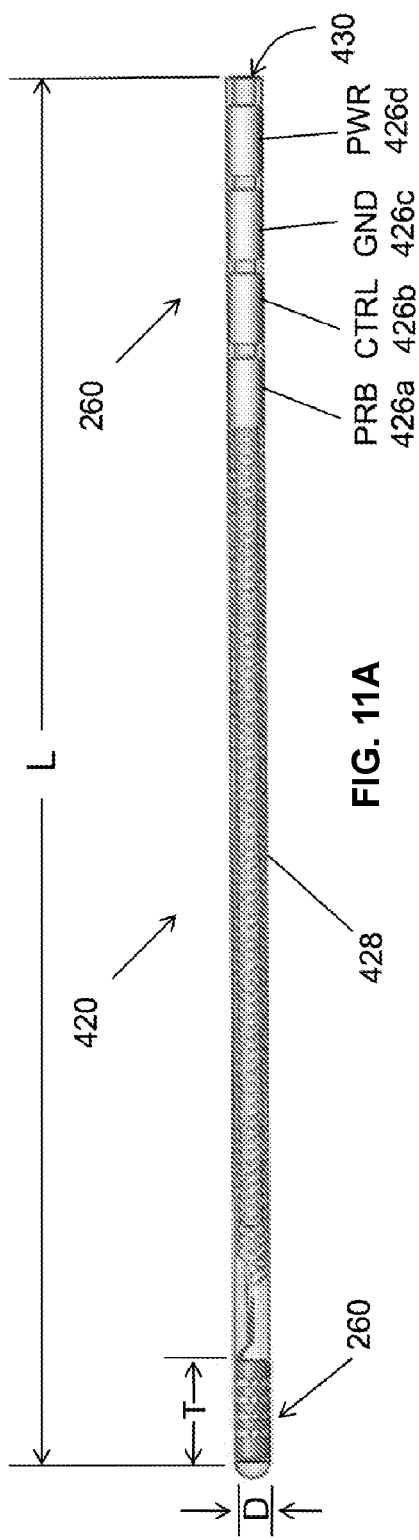
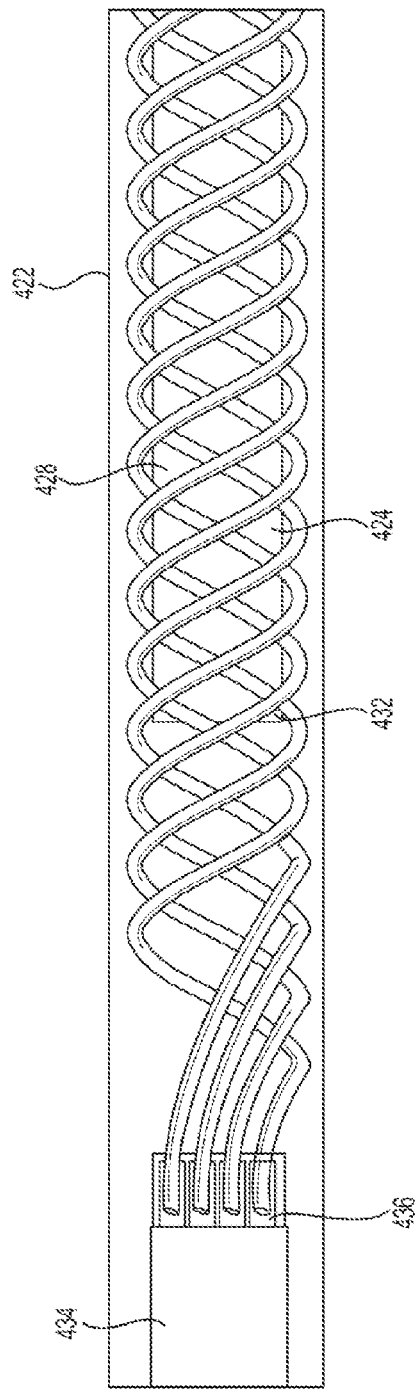

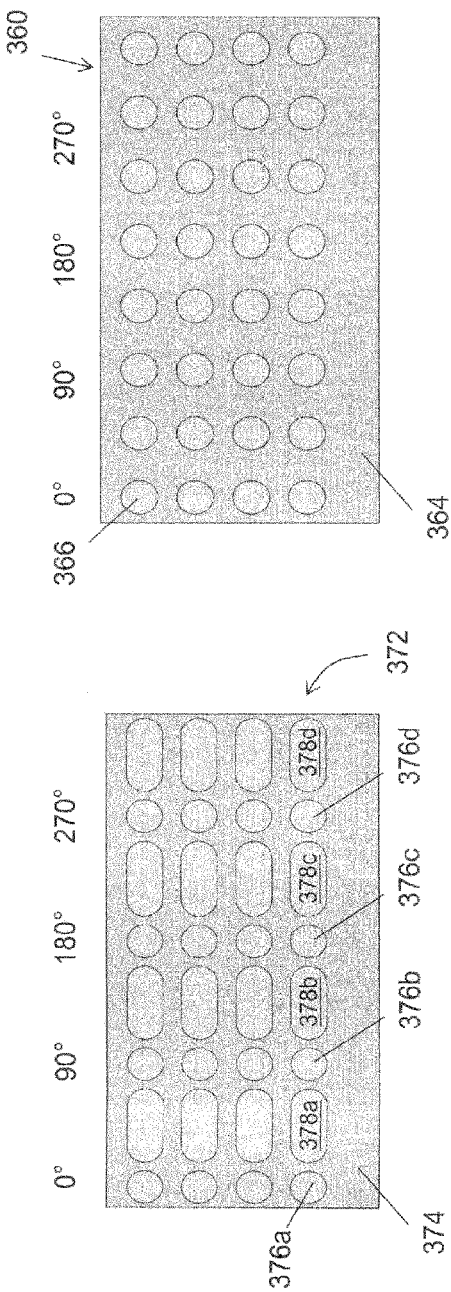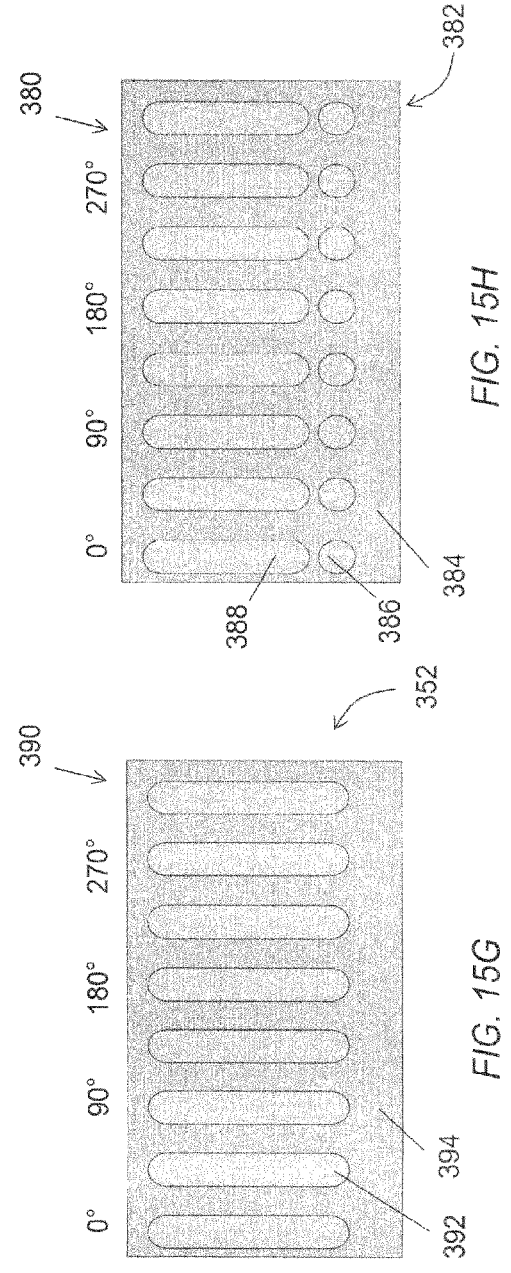

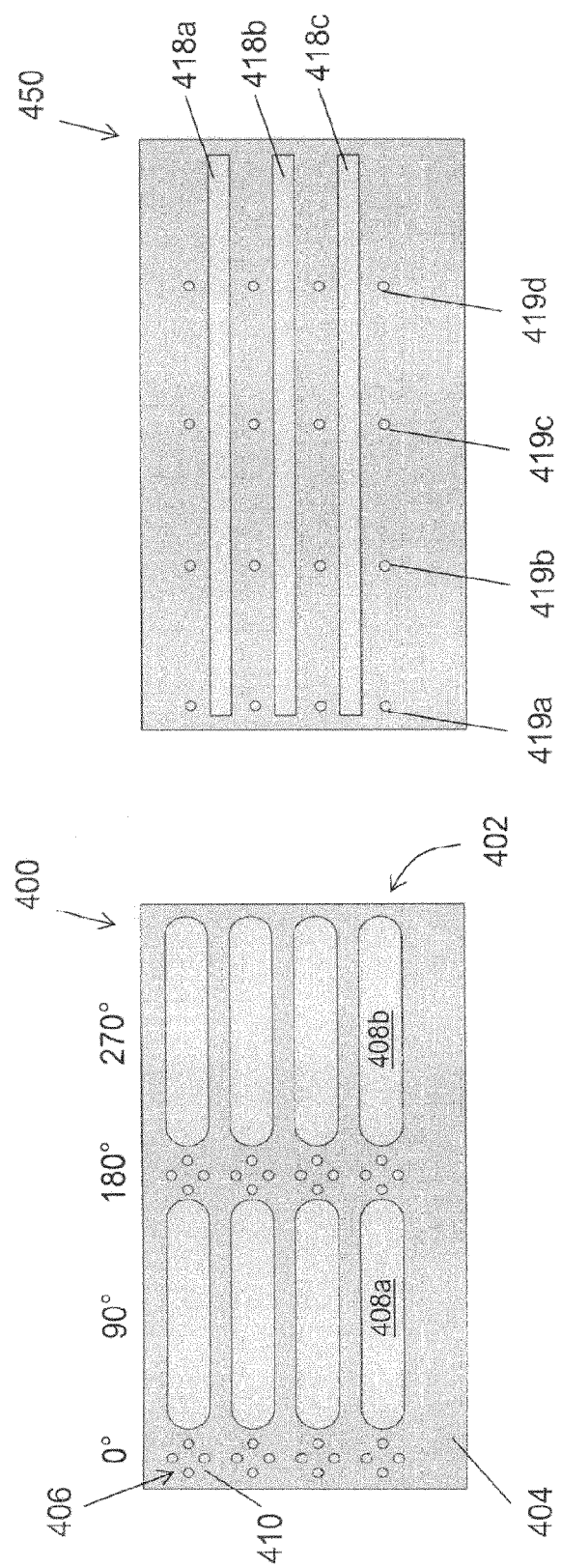

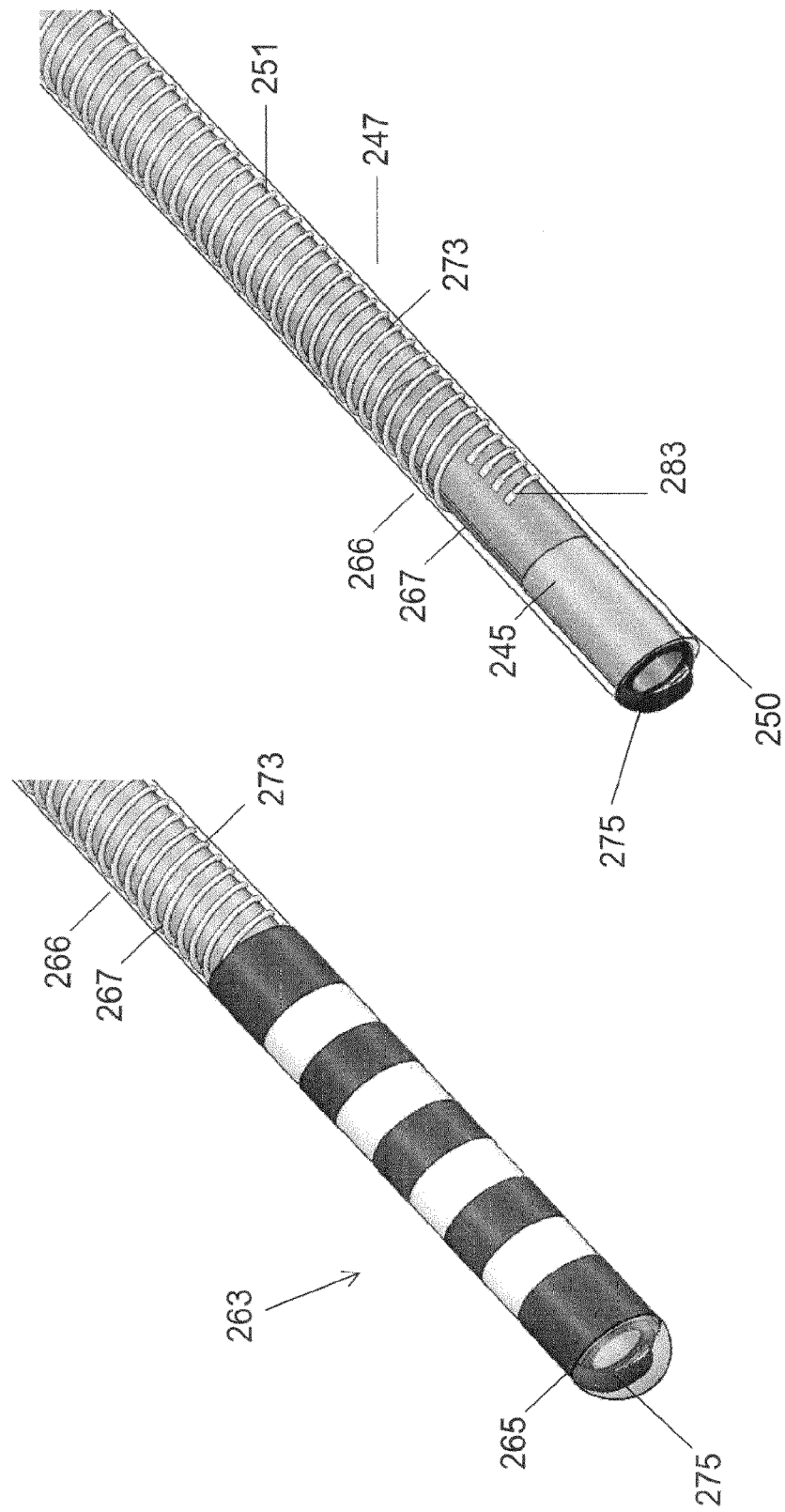

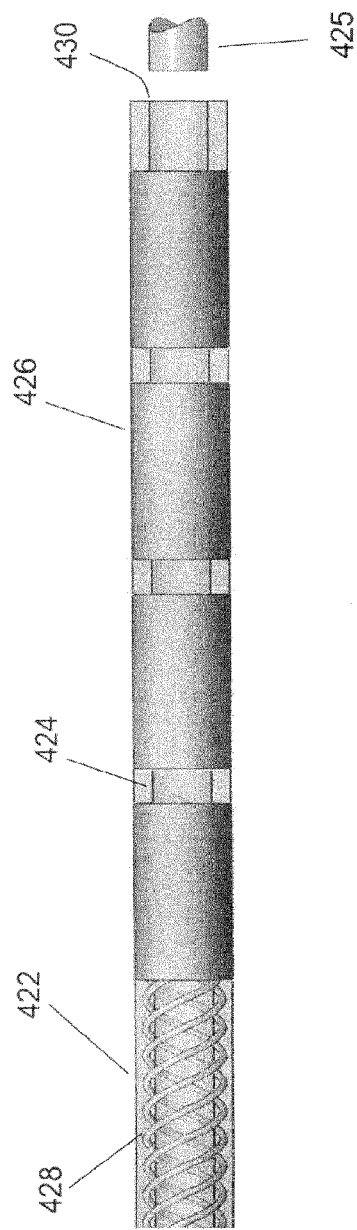
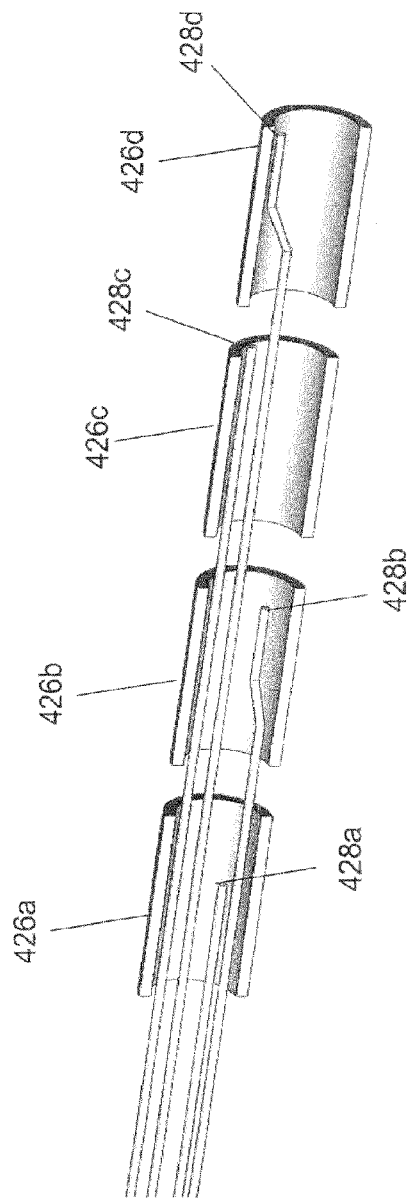
FIG. 18A
FIG. 18B

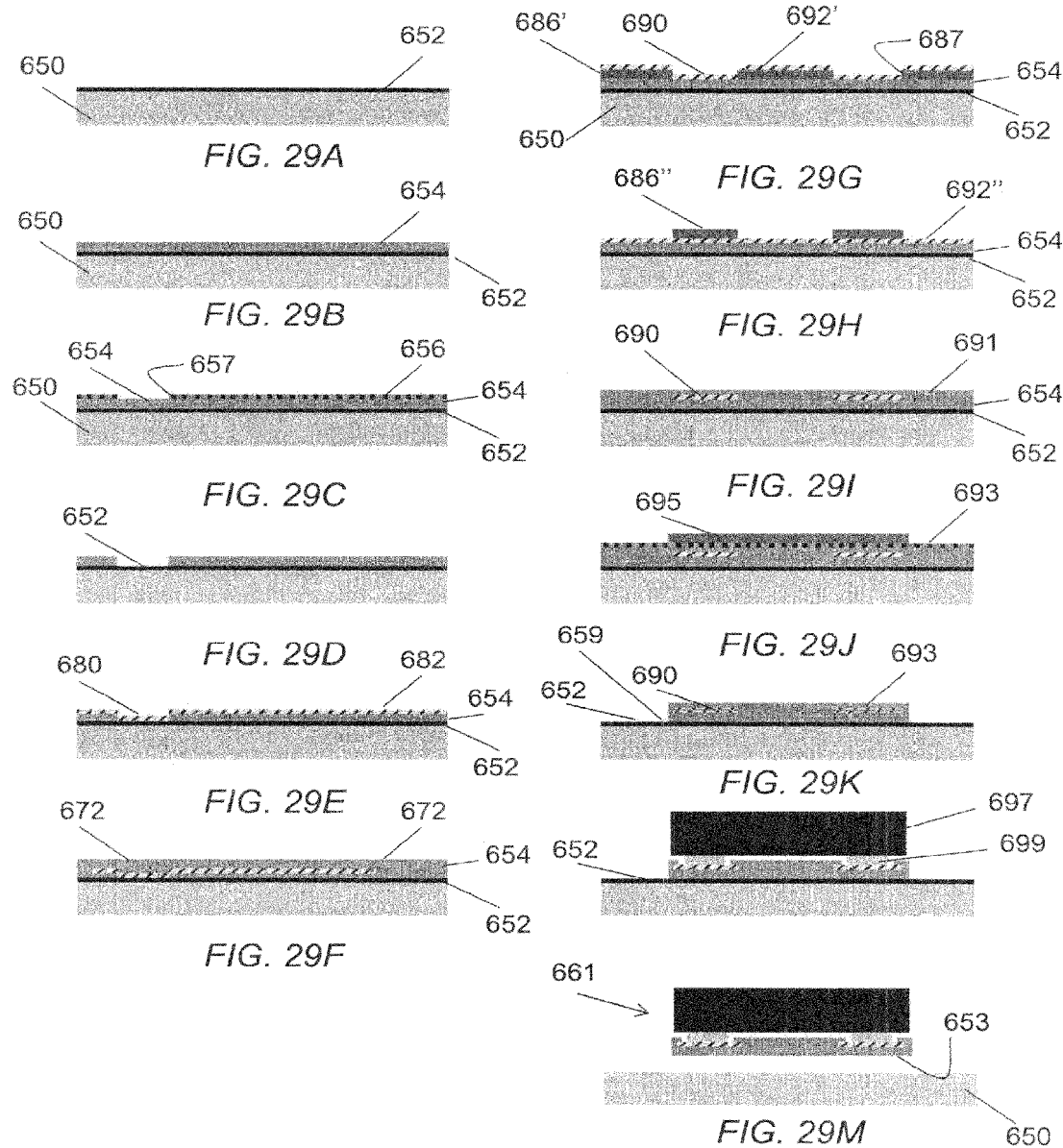

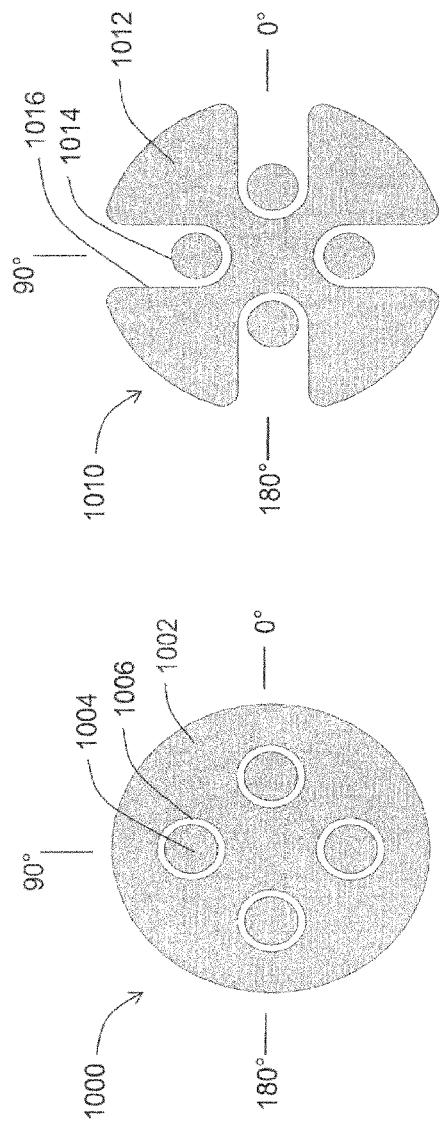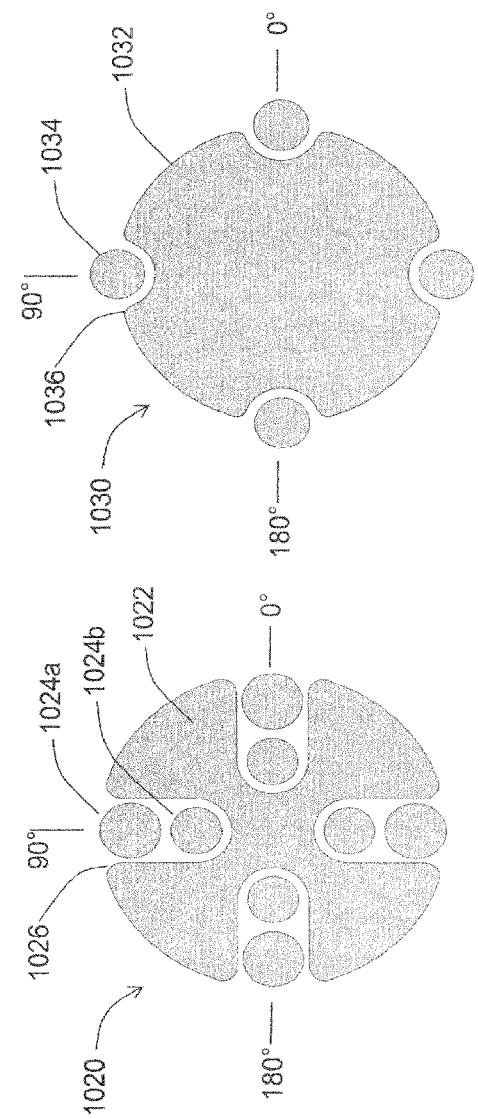

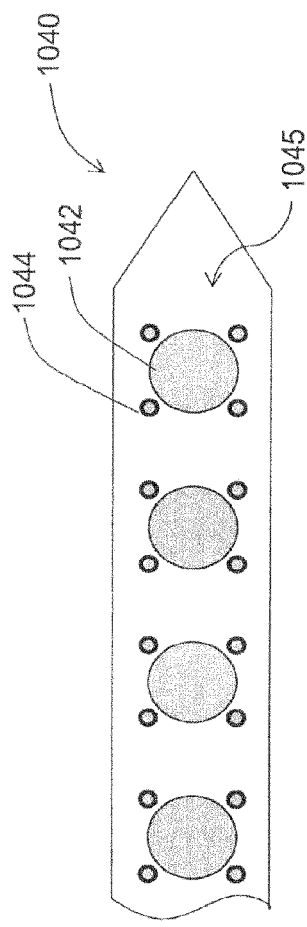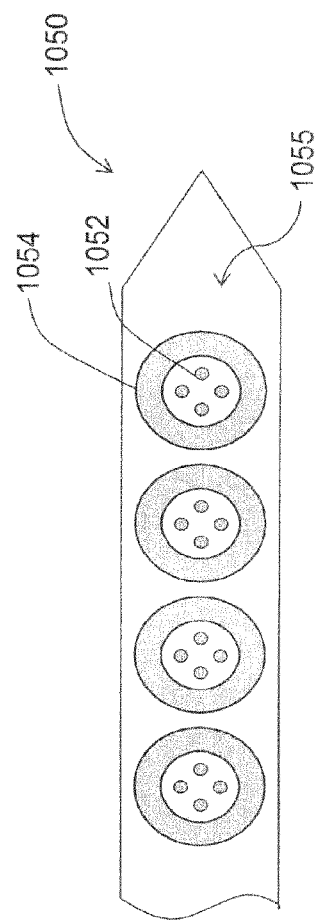
FIG. 39A
FIG. 39B

MICROFABRICATED NEUROSTIMULATION DEVICE

RELATED APPLICATIONS

This is a continuing patent application, which claims priority to U.S. patent application Ser. No. 13/128,821, filed Aug. 1, 2011, which is the U.S. National Stage of PCT International Application Number PCT/IB2009/007715, filed Nov. 12, 2009, which claims priority to U.S. Provisional Application No. 61/113,912, filed Nov. 12, 2008. The contents of the foregoing applications are incorporated herein by reference in their entireties.

FIELD

The present invention relates generally to the field of interacting with biological tissue through the use of electrical probes, and more particularly to interacting with a neurological target through the use of microelectrode probes.

BACKGROUND

Neurostimulation is a category of medical devices that are used to transfer electric charge or electrical fields to tissue and result in a physiological change which benefits the patient, or performs a physiological measurement. Neurostimulation is used today in the cochlea, the retina, the peripheral nerve system, the spine, the brain and other parts of the body.

In a particular application of Neurostimulation, conductive electrodes are placed in contact with certain deep brain structures in order to treat certain neurological conditions. In the case of stimulating the Subthalamic Nucleus, for example, as described in U.S. Pat. No. 5,716,377, or the Globus Pallidus, for example, as described in U.S. Pat. No. 5,683,422, the therapy can treat the symptoms of Movement Disorders such as Parkinson's disease, Essential Tremor or Dystonia. In the case of stimulating the cerebellum, Hippocampus and other brain structures, the therapy can treat the symptoms of Epilepsy [Theodore, W. H., Fisher, R. S., "Brain stimulation for epilepsy", *Lancet Neurology*, 3 (2), pp. 111-118, (2004).].

An implantable pulse generator supplies the electrical signal to the electrode lead in contact with the brain structure. All components are placed surgically.

In most prior art the electrode placed in contact with the brain tissue has been metallic, cylindrical, and relatively large in size (e.g., 1.5 mm in length). In many cases, the electrodes are as large as the brain structures themselves. The large size of electrodes prevents specific and precise stimulation of small brain targets such as the pedunculopontine nucleus. The resulting large electric fields and associated current paths stimulate other structures of the brain, and do not concentrate on the intended target. Furthermore, these large electrodes cannot be used to identify the targets of the brain by neural-recording because the area they cover is very large.

Current techniques that determine placement of such relatively large electrodes are accomplished cutaneously by first inserting a relatively small (e.g., 600 µm diameter probe). The relatively small probe can be inserted along an approach near the target. Recordings of neural activity can be made as the probe is advanced along the approach until the intended target is located. The depth of the probe from a reference is recorded and the relatively large electrodes are inserted along the same trajectory, being placed at the recorded depth. This process is complex, requiring a highly skilled surgeon to place both the probe and later the electrode. Repositioning and removal of the probe and reinsertion of the electrode subject the patient to heightened risk as the risk of tissue damage and bleeding is increased.

Attempts have been made at developing microfabricated devices specifically designed to incorporate an array of microelectrodes which can stimulate small volumes of tissue in the deep brain, for example, as described in U.S. Pat. App. Pub. 2007/0118197, or "Multisite Microelectrodes for Use in Human Deep Brain Stimulation" by Hofmann et al., Microtechnologies in Medicine and Biology, 2006 International Conference on (2006) Pgs. 284-287. The prior devices however do not have a clear path to clinical use because they are too unfamiliar to the neurosurgeon performing the implantation procedure.

An important requirement for a successful outcome of deep brain stimulation (DBS) treatment, is the accurate placement of the stimulation electrodes within the stimulation target area. Mislocation may result in unwanted side-effects, including sensory motor effects and mood changes. Prior art procedures approximately localize the target by pre-surgical imaging and planning to identify a trajectory to minimize risk of damage. It may be impossible to locate the exact functional anatomy within a target region of the brain. The targets themselves may be only a few mm or less, and not detectable through standard imaging techniques alone. Also, position changes of the brain may occur when surgically opening the skull to implant the electrodes and when inserting the electrodes. Current procedures insert test electrodes used to perform electrophysiological exploration of the target area. Once the precise target area is located, the chronic stimulation electrodes can be implanted at the precise location.

Disadvantages to the current technology include extension of operation time by several hours, which can be an increased burden for the patient, who is typically awake during such procedures, and extended cost associated with lengthier procedures. Increased risk of surgical complications from bleeding or tissue damage caused by repeated insertion and extraction of test and chronic leads. Possibility that chronic leads are not precisely located at identified target for any number of reasons, including further brain movement. An increased chance of infection due to an open craniotomy for several hours.

SUMMARY

For efficient stimulation of small brain structures, small electrodes are required. After placement of the electrode lead, the surgeon should be able to identify the area of the brain that requires stimulation by recording from the electrode. Subsequently the surgeon should stimulate the identified structure.

For efficient stimulation of large brain structures, electrodes that contain a higher number of edges are provided.

The invention describes a system which places many microelectrode structures in the brain, and allows the surgeon to apply a signal to each microelectrode separately, or in parallel. Furthermore, using electronics to record neural activity from the system, the surgeon can develop a localized map of neural activity in the region which the electrode is implanted.

In one aspect, the invention relates to an implantable neurological probe. The neurological probe includes an elongated probe shaft and an arrangement of multiple microelectrode elements disposed at a distal end of the elongated probe shaft. At least one electrical contact is arranged proximally along the probe shaft. The neurological probe also includes at least one electrical conductor in electrical communication between at least one of the plurality of microelectrode elements and the at least one electrical contact.

In another aspect, the invention relates to a process for stimulating a neurological target. The process includes implanting a neurological probe within a vicinity of a neurological target site. The neurological probe itself comprising an elongated probe shaft, multiple microelectrode elements arranged at a distal end of the elongated probe shaft, at least one electrical contact arranged proximally along the probe shaft, and at least one electrical conductor in electrical communication between at least one of the multiple microelectrode elements and the at least one electrical contact. The at least one electrical contact is connected to a neurological stimulation source supplying an electrical signal. One or more of the microelectrode elements is energized by the supplied electrical signal. The one or more energized microelectrode elements produce an electric field adapted to stimulate the neurological target site.

In yet another aspect, the invention relates to an implantable neurological probe kit. The kit includes a neurological probe. The neurological probe includes an elongated flexible probe shaft having a central lumen accessible at a proximal end of the neurological probe. The device includes multiple microelectrode elements arranged at a distal end of the elongated probe shaft. At least one electrical contact arranged proximally along the probe shaft. At least one electrical conductor in electrical communication between at least one of the plurality of microelectrode elements and the at least one electrical contact. The neurological probe kit also includes a trocar, or stylet, configured for removable insertion into the central lumen of the elongated flexible probe shaft, to keep the elongated flexible probe shaft substantially rigid during insertion into biological tissue.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 7A is a planar view of an alternative embodiment of a microelectrode assembly.

FIG. 7B is a perspective view of a distal portion of a microelectrode array of FIG. 7A.

FIG. 7E is an image of an assembled distal portion of the microelectrode array of FIG. 7A.

FIG. 11A is a planar view of another embodiment of an elongated microelectrode assembly.

FIG. 11B is a more detailed view of a portion of the elongated microelectrode assembly illustrated in FIG. 11A.

FIG. 15A through FIG. 15J illustrate various alternative embodiments of a pre-installed microelectrode assembly.

FIG. 17A through 17B are cutaway views demonstrating alternative assembly methods of a distal portion of an embodiment of a microelectrode array.

FIG. 18A is a more detailed view of a distal portion of an elongated microelectrode assembly.

FIG. 18B is a more detailed cross-sectional view of the distal portion of the elongated microelectrode assembly illustrated in FIG. 18A.

FIG. 29A through FIG. 29M illustrate cross sections of an exemplary microelectrode device at various different stages of construction according to an exemplary fabrication procedure.

FIG. 38A through FIG. 38D are a schematic views of various alternative embodiments of a microelectrode array.

FIG. 39A through FIG. 39B are a schematic views of various alternative embodiments of a microelectrode array.

DETAILED DESCRIPTION OF THE PREFERRED EMBODIMENTS

Figure 1:
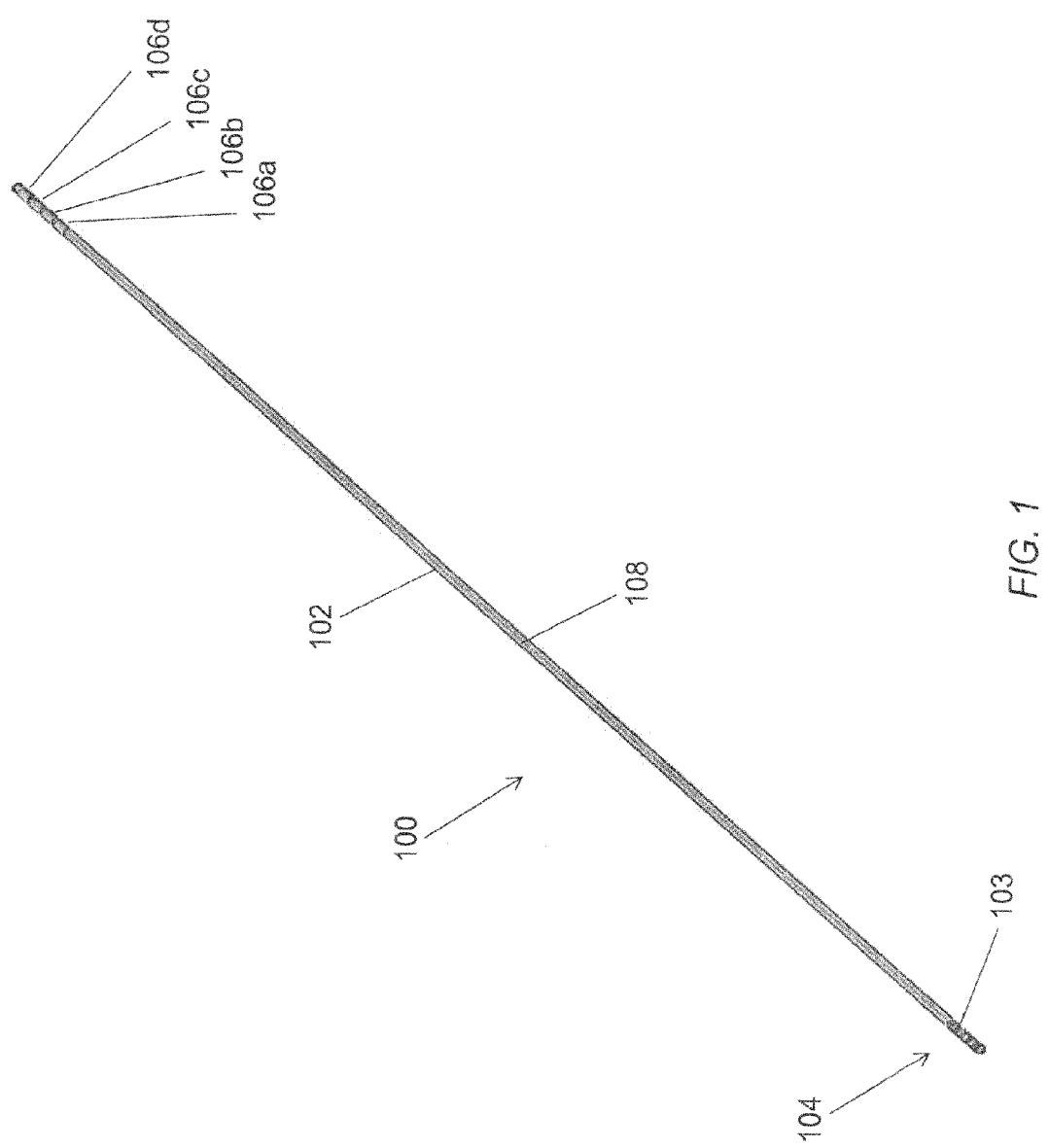
FIG. 1 is a perspective view of one embodiment of an elongated microelectrode assembly.

Described herein are microelectrode array devices, and methods of fabrication and use of the same, to provide highly localized and efficient electrical stimulation of a neurological target, such as individual neurons, groups of neurons, and neural tissue as may be located in an animal nervous system, such as deep within a human brain. In larger brain targets such as the Globus Pallidus, or in targets that requires high levels of neural stimulation, such as Brodmann Area 25, more electrodes are required within the target itself. A higher number of electrodes, and more specifically a higher number of electrode edges, will increase the number of neurons that are captured by the electric field for either stimulation or inhibition.

The stimulation can be highly localized, because the microelectrode elements can be as small as only 2 μm or large as 2 mm in either of diameter or width. The relative spacing between such microelectrode elements can also be as small as only 2 μm or as large as 2 mm. Although 2 μm are indicated as lower limits to either dimension or spacing, other embodiments are possible having dimensions and/or inter-element spacing of less than 2 μm, as may be practically limited by fabrication techniques. Generally, microelectrodes of about 500 μm in diameter or width, with about a 500 μm spacing are particularly efficient in stimulating neural tissue. An array of such microelectrode elements may consist of one or more such elements (e.g., sixteen elements), each disposed at a respective position, or site. This is in contrast to currently available stimulation leads, such as the Model 3387 or Model 3389 DBS leads commercially available from Medtronic, Inc. of Minneapolis, Minn. Such commercially available devices include relatively large, cylindrical electrodes measuring about 1.5 mm in height, and having a maximum of only four electrodes in use today for deep brain stimulation.

Smaller microelectrode elements can be used to provide neurological stimulation that is highly localized and efficient because an array of such microelectrodes can also be used to identify the stimulation region of interest. For example, one or more microelectrode elements of such an array of microelectrode elements can be used to detect and, in some instances, record neuronal activity in the vicinity of the detecting/recording microelectrode elements. Such refinement offered by the relatively small size and/or spacing of the microelectrode elements can be used to obtain a highly localized map of neuronal activity in the region surrounding the implant. A suitably dimensioned microelectrode array having multiple microelectrode elements positioned in a general vicinity of a neurological target, can be used to locate a precise neurological target without further repositioning, by identifying those one or more microelectrode elements located in a very specific region of the neurological target. The microelectrode array can be programmed to stimulate in a very specific region, for example, using only a certain number of the microelectrode elements to actively stimulate the surrounding neurons and/or neuronal tissue, while other electrode elements of the array remain inactive.

In some embodiments, an elongated device including such a microelectrode array having elements with relatively small size and/or spacing can be used to obtain a highly localized map of neuronal activity in the region surrounding the implant. For example, such a device configured with a linear array of microelectrodes positioned along a length of a distal end of the device can be placed into a patient's brain. Preferably, the elements of the microelectrode array span a region including the neurological target. Neurological activity can then be independently detected by one or more of the microelectrode elements. The detected activity may be captured in a recorder or display device, allowing a clinician to identify which one or more of the microelectrode elements is positioned closest to the intended target. Knowing a respective location of each of the microelectrode elements along the device, and determining the distance to a reference, such as the patient's skull, a precise location of the target can be determined as the distance along a trajectory of the device, measured from the reference to the particular microelectrode element. Beneficially, location of the target can be determined without any repositioning of the elongated device, thereby simplifying the medical procedure and reducing patient risk.

In some embodiments, the device is cutaneous, being removed after the target has been located, being replaced with a chronic probe, positioned at the determined target location. Alternatively or in addition, the device itself can be left in place as a chronic device, the same microelectrodes, or different ones, being used to record and/or stimulate the neurological target over an extended period.

One embodiment of a microelectrode device illustrated in FIG. 1 includes an elongated microelectrode probe assembly 100 sometimes referred to as an electrode lead. The microelectrode probe assembly 100 includes an elongated cylindrical member, or body 102 including a microelectrode array 104 located relative to a distal end and one or more electrical contacts located relative to a proximal end. The exemplary microelectrode probe assembly 100 includes a microelectrode array 104 adjacent to its distal tip. The microelectrode array 104 has four electrically conductive, cylindrical microelectrode elements 103 disposed along an exterior surface of a cylindrical substrate. The microelectrode elements 103 are microfabricated and wrapped around the cylindrical member 102. The microelectrode probe assembly 100 also includes four electrically conductive, cylindrical contacts, or contact rings 106a, 106b, 106c, 106d (generally 106) distributed along a longitudinal axis of the proximal end of the assembly 100. In the exemplary embodiment, each of the microelectrode elements 103 is in electrical communication with a respective one of the proximal contacts 106 via a respective electrical conductor 108. In the exemplary embodiment, all of the electrical conductors 108 are disposed within an interior region of the elongated cylindrical member 102. There are no electronics on this device 100. In use, signals are directed from an implantable pulse generator to the microarray. The length of the cylinder can vary.

The microelectrode probe assembly 100 is preferably sized and shaped for its intended neurological application. For example, the microelectrode probe assembly 100 may be at least partially placed within the central nervous system. Alternatively or in addition, the microelectrode probe assembly 100 may be at least partially placed within other parts of the body, such as the retina, the cochlea, the epidural space of the spine, and other locations within the peripheral nervous system. Thus the diameter and length of the microelectrode probe assembly 100 may vary depending on the particular anatomical target. Additionally, the configuration of the microelectrode array 104 is also sized and shaped for an intended neurological target. The number, shape, orientation, size, and spacing of the microelectrode elements 103 of the array 104 can be defined in response to the intended neurological target.

In at least some embodiments one or more of the microelectrode elements 103 are sized and or spaced to record from and/or stimulate a single neuron. The microelectrode probe assembly 100 can be used to detect and/or record neuronal activity at the neurological target. Neuronal activity naturally occurring within the neurological target gives rise to local electromagnetic fields that can be detected by one or more of the microelectrode elements 103 of the microelectrode array 104. For example, electric fields produced by neurons will polarize one or more of the microelectrode elements 103. Such polarization gives rise to an electrical potential with respect to a reference, such as electrical ground, or another one of the microelectrode elements 103. Such electric activity can be further conducted to one or more of the cylindrical contacts 106 through the internal electrical conductors 108. One or more of the cylindrical contacts 106, in turn, can be connected to one or more additional medical devices for further processing of the detected electrical activity. For example, the cylindrical contacts 106 can be coupled to a display device or recording device for displaying and/or recording electrical activity from the neurological target.

Alternatively or in addition, one or more of the microelectrode elements 103 can be used to electrically stimulate the neurological target. For example, one or more externally generated electrical signals can be applied to one or more of the cylindrical contacts 106. These electrical signals can be conducted through the internal electrical conductors 108 to one or more of the microelectrode elements 103 of the microelectrode array 104. Depending on the amplitude and polarity of the electrical signals, an electrical field will be induced by the polarized microelectrode elements 103. Electrical fields induced by such polarization can interact with one or more neurons at the neurological target.

Microfabricated Components

A microfabrication procedure can be used to implement electrically conductive traces within an insulative substrate to form any of the microelectrode array devices described herein, whether the array devices are rigid or flexible. The microfabricated components include portions of the microelectrode array assembly. The microelectrode array can be implemented in a polymeric material such as polyimide or parylene and includes thin film or plated layers of a metal or metal oxide with high charge transfer capability such as platinum, platinum-iridium, iridium, iridium oxide or titanium. In some embodiments, other metals, metal alloys, and electrically conductive materials, such as doped semiconductors, conductive polymers, and conductive ceramics may be used. In some embodiments, the polymeric and metallic layers are deposited sequentially and formed using established principles of microfabrication such as spin coating, DC/RF sputtering, photolithography, plasma etching, and etching with a mask consisting of a secondary or sacrificial material such as silicon dioxide or photosensitive resist.

The metallic layer is formed to create one or more of the microelectrode array elements and electrically conductive traces that connect the array elements to one or more of the electronics, when included, internal electrical conductors of the elongated cylindrical member, and housing. In some embodiments, the microelectrode array includes multiple layers. For example, the polymeric layers serve to isolate the traces from each other, while also providing the structure of the implant's stimulating/recording tip. There are several fabrication methods which can be described to build such a microfabricated component.

The insulative substrate can be a polymer, such as a polyimide or parylene but can also be polyurethane or polysiloxane (silicone), or any other suitable insulator. For substantially non-flexible, or rigid embodiments, a rigid or semi-rigid substrate can be included. In some embodiments, the microelectrode array device is formed on at least one surface of a rigid substrate, such as a planar ceramic member. Alternatively or in addition, one or more rigid or semi-rigid supporting members can be attached during fabrication to provide a desired amount of rigidity. Generally, the microfabricated component can be fabricated, for example, using a series of additive and subtractive processes that produce a stack of materials.

Mechanical components of the implantable neurological probe assembly 100 include the elongated cylindrical member 102, which can be a simple polymeric cylinder. In some embodiments the cylindrical member may be composed of two concentric tubes with wire traces wrapped around the inner tube, in the space between the concentric tubes. The elongated cylindrical member 102 can vary in length and diameter but is generally at least about 28 cm long, and around 1.27 mm in diameter. In some embodiments, the microfabricated component is wrapped around an external surface of the cylindrical member 102. In some embodiments, the microfabricated component is wrapped around an additional tube at the distal end of the cylindrical member 102. Alternatively or in addition, the microfabricated components can be attached to the cylindrical member 102 to protrude at the distal tip, from the cylindrical member's interior. The cylindrical member 102 also contains electrical wires 108 within that connect at one end to the microfabricated component, at another end to the cylindrical contacts 106 for interconnection to an implantable pulse generator. In some embodiments, one or more of the microfabricated components and the elongated cylindrical member 102 include one or more electrical components.

The electrical components can be discrete or microelectronic parts. Their purpose is to filter, route, generate, or process signals to and from the microelectrodes. They can be attached to the microfabricated part during production, or bonded afterwards. They will generally be contained within the mechanical component.

The neurological probe 100 can be implanted near a neurological target, such as a target brain structure, using common neurosurgical techniques such as stereotaxy or endoscopy. The neurological probe 100 can be inserted without support, or within a supporting cannula having an inner dimension slightly larger than the outer dimension of the device. The cannula, when used, would be retracted once the neurological probe 100 has been suitably positioned. In some embodiments a lumen along the axis of the cylindrical member 102 permits the insertion of a rigid stylet which renders the neurological probe 100 rigid during surgical implantation. This is particularly helpful during insertion, positioning and repositioning of flexible embodiments of the neurological probe 100. The stylet is removed after implantation leaving the probe in its surgical target.

A clinician can connect one or more of the microelectrode elements to a display unit or a recording unit through the cylindrical contacts 126. The recording unit, not shown, allows a clinician to identify certain regions of the brain according to their electrical activity. In some embodiments, such recording information can be processed automatically, through the use of a suitably programmed computer processor. The electrodes used to record from the brain can be the same electrodes as those used to stimulate tissue. The recording electrodes can also be separate from those used to stimulate the brain. This situation might be preferred because electrodes destined for recording may be different in size and design than those for stimulation.

The operator can connect the electrodes to an external stimulation source or an implantable source. In either instance, the source can include a pulse generator for applying signals to the electrode sites. The signals from such a pulse generator can be connected directly to the electrodes, or they can be preprocessed using electronics embedded in the device. The electronics can filter certain parts of the original signal. If there are more electrodes than signals, the electronics can route or otherwise interconnect the stimulation source as necessary.

Figure 2:
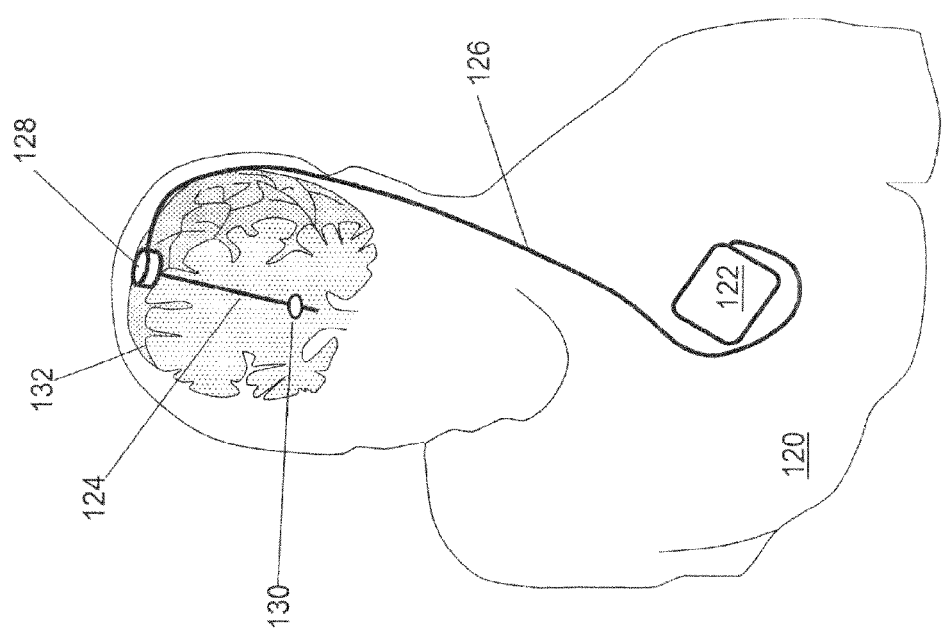
FIG. 2 is a perspective view of a portion of a human anatomy illustrating an exemplary elongated microelectrode assembly implanted therein.

A perspective view of the portion of a human anatomy is illustrated in FIG. 2, showing implantation of an exemplary elongated microelectrode probe assembly 124 position for interaction with a neurological target located deep within the brain. A distal portion of the microelectrode probe assembly 124 is positioned at the neurological target 130, in this instance located within the human brain 132. In some embodiments the proximal end of the microelectrode probe assembly 124 is connected to a first medical device 128. For example, the first medical device 128 may include an electronic assembly implanted external to the brain 132 to minimize invasion into the brain and flesh or to facilitate wireless access to the electronic assembly 128. Alternatively or in addition, a second medical device, which again may include an electronic assembly such as a pulse generator 122 can be implanted at a remote portion of the subject body. As shown, a second electronic assembly 122 is implanted within a chest cavity 120. When one or more medical devices, such as the exemplary pulse generator 122 are located remotely in this manner, a cable 126 may also be implanted within the subject's body to interconnect the pulse generator 122 to the electronic assembly 128, when present or directly to cylindrical contacts located at the proximal end of the microelectrode probe assembly 124.

Figure 3:
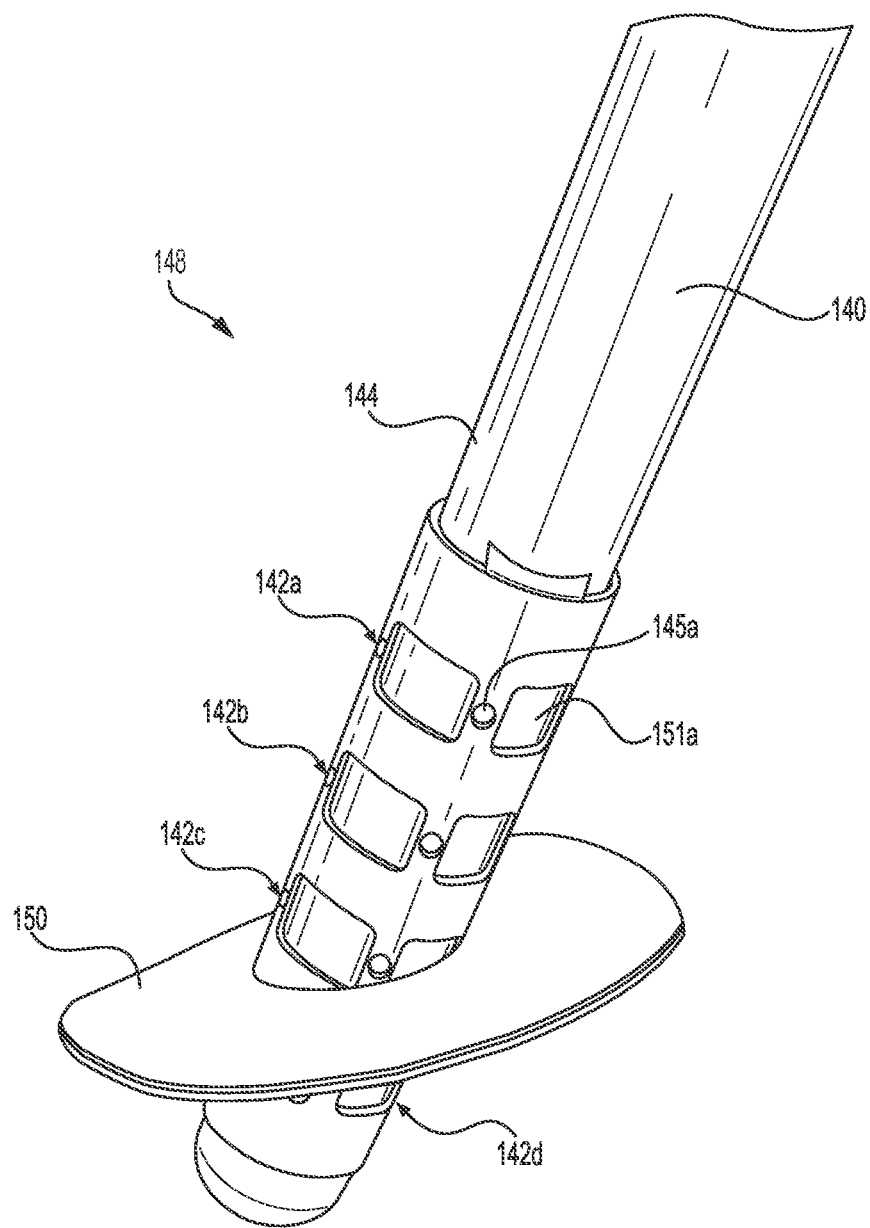
FIG. 3 is a perspective view of a portion of a human anatomy illustrating an exemplary microelectrode structure positioned at a neurological target.

Referring now to FIG. 3, a cross-sectional view of a portion of an anatomy 148 is shown, illustrating an exemplary microelectrode probe assembly 140 positioned at a neurological target 150 (e.g., subthalamic nucleus, shown). The microelectrode probe assembly 140 includes an array of microelectrode elements 142a, 142b, 142c, 142d (generally 142) distributed along an elongated, cylindrical supporting structure 144. Preferably, the microelectrode probe assembly 140 is shaped and sized to allow one or more of the microelectrode elements 142 to be positioned at the neurological target 150. To this end, materials used in construction of microelectrode probe assembly, as well as one or more of its construction features, size, shape, and orientation can be selected for biocompatibility.

As illustrated, one or more of the microelectrode elements 142c of the microelectrode probe assembly 140 are positioned in intimate contact with the neurological target 150. In more detail, each microelectrode element is configured here as an annular array of sub-elements 145, 151. The sub-elements 145, 151 can be distributed about a circumference of the probe assembly 140, at a common axial displacement from the distal end. It is understood that some sub-elements of such an annular array 142c can be in contact with the neurological target, while other sub-elements of the same annular array 142c are not (as shown). One or more additional microelectrode elements 142 of the probe assembly 140 may reside at locations not in the immediate vicinity of the neurological target 150. In at least some embodiments, one or more of the microelectrode elements 142 are remotely accessible from a proximal end of the probe assembly 140 via one or more electrically conductive leads (not shown).

In at least some embodiments, selectable sub-elements 145, 151 can be activated to record and or stimulate the target 150. For example, recordings of neurological activity from sub-elements 145 in contact with the target 150 can be used to identify the location of the target 150 relative to the probe assembly 140. As determined from the recordings, only those sub-elements 151 in contact with the target may be activated to stimulate the target. Depending upon the location of the target, this may result in an annular array 142 stimulating a selectable angular region about the probe assembly 140.

Any of the supporting structures described herein, such as the supporting structure 144 illustrated here can be a ridged, or semi ridged structure, such as a polymeric cylinder. Alternatively or in addition, the structure can be a flexible structure, such as one or more flexible substantially non conducting substrate (i.e., a bi-electric ribbon) onto which the microelectrode elements 142 are formed as electrically conductive film layers. The one or more microelectrode elements 142 are in communication with electronic circuitry (not shown) through one or more electrical leads (not shown) that can be routed through an internal lumen of a supporting structure 144 and/or formed using elongated film layers along a flexible, ribbon like supporting structure 144.

In some embodiments, the microelectrode elements 142 can be placed into the brain generally for recording and/or stimulation of the cortex and for deep brain stimulation and/or recording of neurological targets including the subthalamic nucleus and the globus pallidus. The microelectrode elements 142 can also be placed in other parts of the body, such as the retina, the spine, the peripheral nervous system for neural recording and/or neural stimulation of such portions of an animal anatomy. Although microelectrodes are discussed generally throughout the various embodiments, there is no intention to limit the upper or lower size of the microelectrodes. The devices and methods described herein are generally scalable, with a microelectrode size determined according to the intended application. For at least some of the neurological applications, microelectrodes are dimensioned sub-millimeter. In some embodiments, microelectrodes are dimensioned sub-micron. In some embodiments, the microelectrodes are formed as planar structures having a diameter of about 50 μm that are arranged in a linear array with center to center spacing of about 100 μm. The planar structure of the microelectrodes can have regular shapes, such as circles, ellipses, polygons, irregular shapes, or a combination of such regular and/or irregular shapes.

This probe assembly 140 is implantable near a neurological target, such as a target brain structure, using common neurosurgical techniques such as stereotaxy or endoscopy. The device might be inserted without support or within a cannula which may have an inner dimension slightly larger than the outer dimension of the device. Alternatively, or in addition to, the device may have a rigid stylet miming along its central axis with an outer diameter that is smaller than the inner diameter of an axial lumen in the device. When used, such a cannula, or a stylet, is generally retracted once the device is in position.

The operator can connect the probe assembly 140 to a recorder unit configured to identify certain regions of the neurological target (e.g., the brain) according to the electrical activity detected by the probe assembly 140. In some embodiments, the microelectrode elements 142 used to record from the neurological target 150 can be the same microelectrodes as those used to stimulate the target in applications in which both recording and stimulation are accomplished. Alternatively or in addition, the microelectrode elements 142 used to record from the neurological target 150 can be separate microelectrode elements 142 from those used to stimulate the target 150. This is demonstrated in this embodiment, in which each microelectrode assembly includes one or more recording electrodes 145 and one or more stimulating electrodes 151. As shown, the dedicated recording electrode 145 is smaller than dedicated stimulation electrode 151. In some embodiments, microelectrodes destined for recording (e.g., 145) may differ in one or more of size, shape, number, and arrangement from those microelectrodes destined for stimulation, e.g., using different microelectrodes.

The microelectrode elements 142 configured for stimulation can be connected to a stimulation source through one or more interconnecting leads. In some embodiment, at least a portion of the stimulation source can be extracorporeal. Alternatively or in addition, the stimulation source can be in vivo. Any implanted elements of the stimulation source are preferably fabricated and/or contained with a hermetically sealed, bio-compatible envelope. Such bio-compatible packaging of signal sources is well known, for example, in the area of artificial pacemakers. The stimulation source, when provided, may be a controllable signal generator producing a desired signal according to a prescribed input. For example, the signal generator may receive an input indicative of a desired output stimulation signal frequency. Such output stimulation signals can have a variety of wave forms, such as pulses, charged balanced pulses, sinusoidal, square wave, triangle wave, and combinations of such basic wave forms.

In some embodiments, the stimulation source includes a pulse generator for applying signals to the microelectrodes site. The signals from the pulse generator can be connected directly to the microelectrodes, or they can be preprocessed using electronics. In some embodiments, such preprocessing electronics are embedded within the implantable device. The preprocessing electronics can filter certain parts of an original signal, such as a cardiac pacemaker signal, in order to select preferred frequency components of the original signal that are at or near a peak resistance frequency of the microelectrodes. For embodiments in which there are more microelectrodes than signals, electronics can route the stimulation signals to preferred one or more of the microelectrodes.

Figure 4:
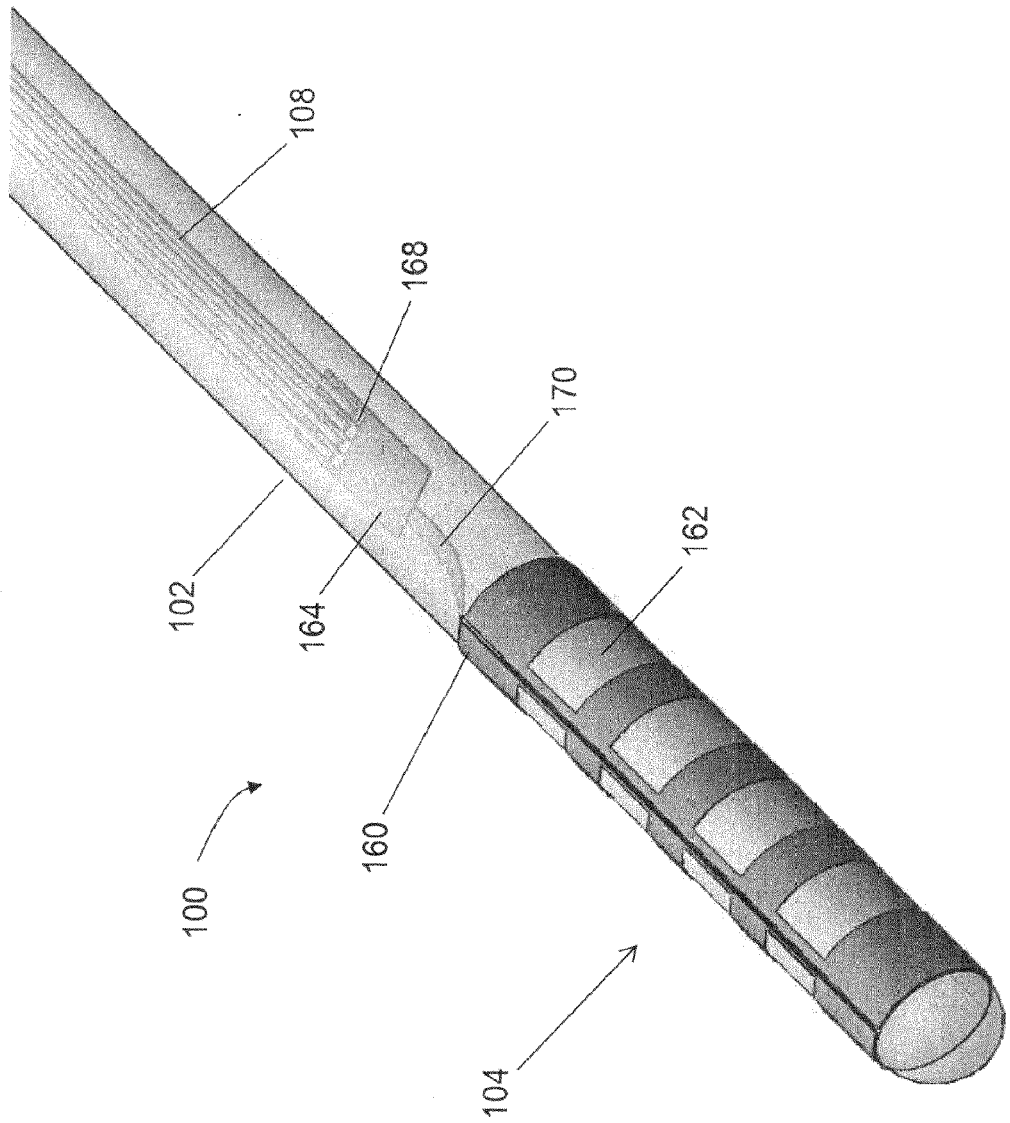
FIG. 4 is a perspective view of a distal portion of the elongated microelectrode assembly of FIG. 1.

Referring now to FIG. 4 a more detailed view of a distal end of the microelectrode probe assembly 100 as shown. The microelectrode array 104 includes a formable planar substrate 160. One or more electronically conducting regions 162 are disposed along portions of the formable planar substrate 160. The microelectrode probe assembly 100 can be formed using a polyimide structure (e.g., 160) containing multiple microelectrode elements wrapped and molded in place around an elongated, cylindrical polyurethane body. In the illustrative embodiment, the electronically conducting regions 162, or microelectrode elements, are thin-film conducting bands extending around a substantial circumference of an external surface of the elongated cylindrical member 102. As shown, there are four such electrically conducting bands 162 spaced apart, each located at a different respective distance measured from a distal tip of the elongated microelectrode assembly 102. The four conducting bands 162 can be electrically coupled to an implantable pulse generator. In some embodiments, one or more of the conducting bands are coupled to the implantable pulse generator through an impedance match circuit (not shown). The electrically conductive electrode width in this example is about 700 μm (the particular width is selectable and, for example, can range from 2 μm or less to 2 mm or more), there are four such microelectrode rings which encircle the body. The electrically conductive microelectrode elements 162 can be formed using metals, suitably doped semiconductors, conductive polymers, conductive ceramics, and combinations thereof.

In at least some embodiments the formable planar substrate 160 includes a longitudinal extension 164. This longitudinal extension 164 may include one or more electrical circuit elements such as one or more electrically conductive wire-lead contacts 168 as shown. One or more of the electrically conductive circuit elements, such as the wire-lead contacts 168 may be in electrical communication with one or more of the electrically conducting bands 162 through interconnecting traces 166 extending between the wire-lead contacts 168 and the electrically conducting bands 162. As illustrated, at least a portion of the microelectrode array 104 is located along an external surface of the elongated microelectrode probe assembly 100. Other portions such as the longitudinal extension 164 maybe located within an interior portion of the elongated cylindrical member 102. Four internal electrical conductors, or leads 108, are illustrated extending along an interior portion of the elongated cylindrical member 102. Distal tips of each of the internal electrical conductors 108 are in electrical communication with a respective one of the wire-lead contact 168 as illustrated.

Figure 5:
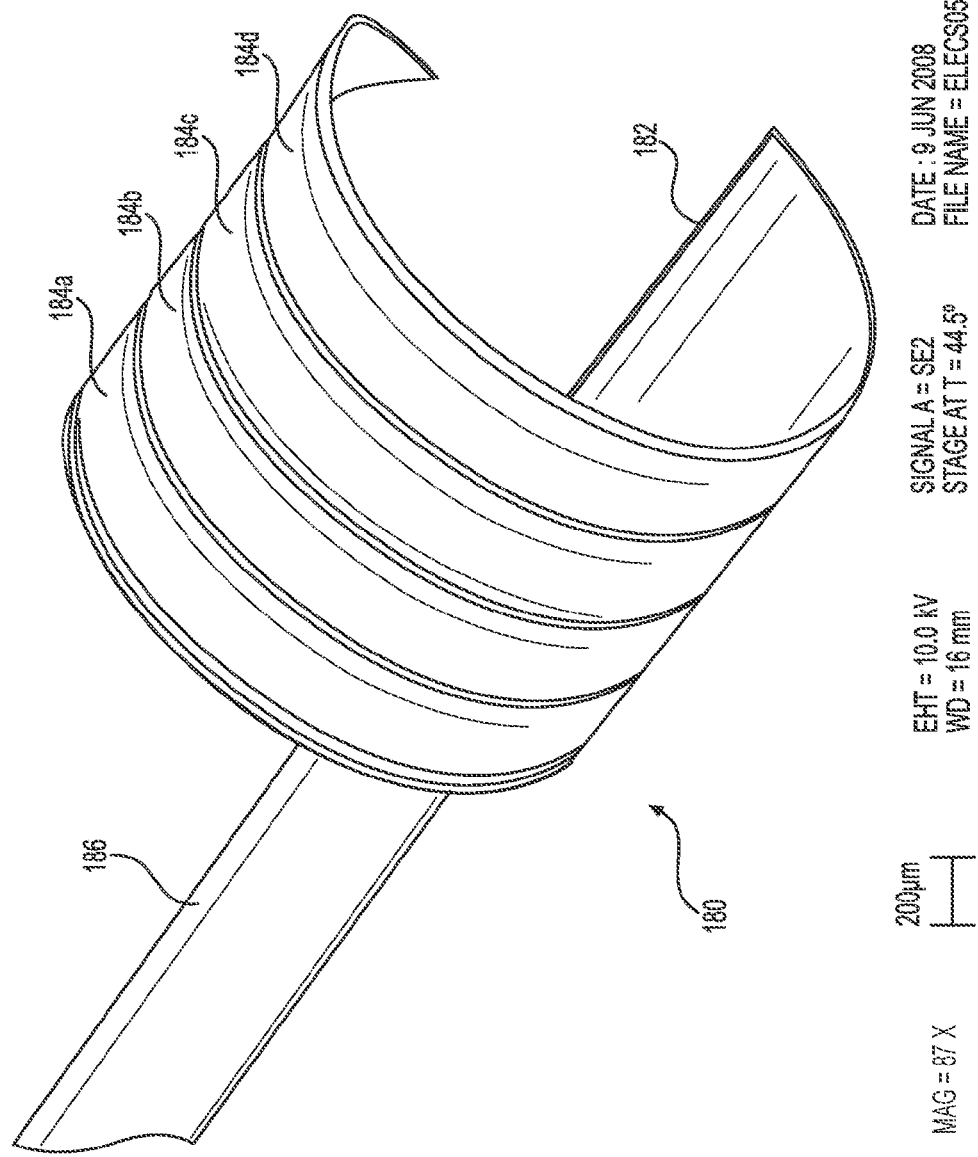
FIG. 5 is an image of an embodiment of a microelectrode array microelectromechanical system (MEMS).

An exemplary embodiment of a microelectrode array 180 is illustrated in FIG. 5. The microelectrode array 180 can be prepared as a micro-electromechanical system (MEMS). Such a MEMS film device 180 can be prepared from a substantially electrically insulative planar substrate 182 onto which the electrically conductive elements are formed. For example, a dielectric planar substrate 182 is prepared to include electrically conductive surfaces corresponding to the multiple elements of the microelectrode array. As shown, a four element microelectrode array of electrically conducting elements 184a, 184b, 184c, 184d (generally 184) is formed on a polyimide substrate. In some embodiments, the formable planar substrate 182 includes a longitudinal extension 186. One or more of the microelectrode array elements 184 can be connected to one or more other circuit elements such as lead wire traces 186 provided on the longitudinal extension 185. Such a device can be prepared using standard MEMS techniques by which the substrate and conductive elements are prepared in a planar configuration and later formed into a non-planar shape. For example, the four-element microelectrode array 184 can be formed into a substantially cylindrical shape to accommodate an outer surface of an elongated cylindrical member of a microelectrode probe assembly.

Figure 6:
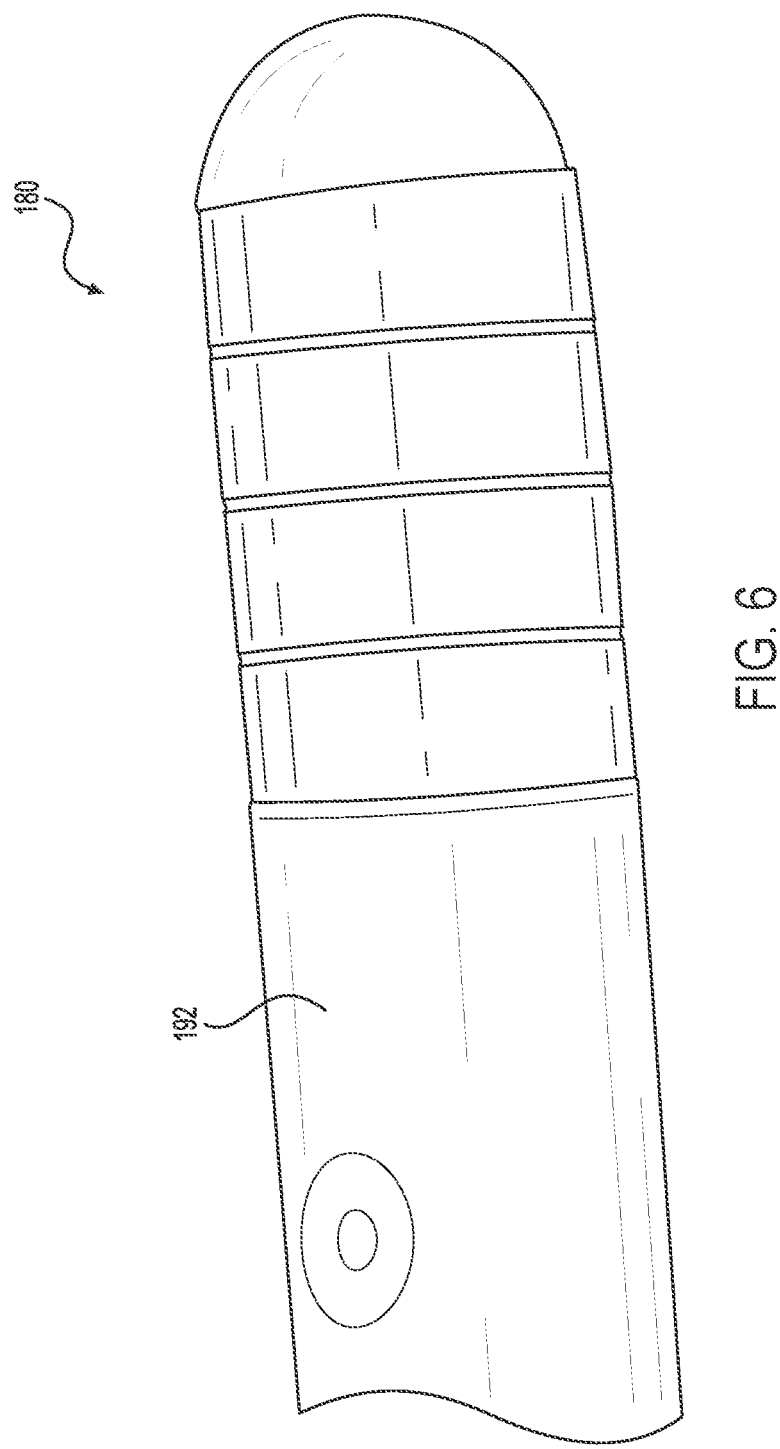
FIG. 6 is an image of one embodiment of a microelectrode array integrally attached to a distal portion of an elongated cylindrical structure.

Referring next to FIG. 6, the MEMS device 180 is shown attached at a distal tip of an elongated cylindrical member 192. The electrically conductive surface of the four-element microelectrode array 184 remains exposed about the outer surface of the elongated cylindrical member 192. Thus, the microelectrode array 184 is positioned for intimate contact and interaction with any neurological target into which the elongated cylindrical member may be placed.

An alternative embodiment of a neurological probe 200 is shown in FIG. 7A. This neurological probe 200 also includes a formable film substrate 205 shown placed at a distal end of an elongated cylindrical body 202. In the illustrated embodiment, the cylindrical body 202 is formed by two coaxial cylindrical members. At a proximal end are eight cylindrical contacts 206, which electrically connect the proximal end to the film substrate 205 at the distal end through lead wires within the coaxial cylindrical members 202.

Referring next to FIG. 7B, a more detailed view of the distal end is shown. Formed along an outer surface of the formed cylindrical substrate 205 are multiple circumferential segmented microelectrode elements 204 and 207 spaced apart along both longitudinal and circumferential axes. In this exemplary embodiment eight such conductive microelectrode elements are included. Microelectrode elements 204 are segmented such that three microelectrodes at a common axial location are disposed about a circumference of the neurological probe 200, referred to herein as segmented elements. Such segmented elements that are independently addressable allow for stimulation a selectable angular region about the probe assembly 140. For example, only those sub-elements on one side of the probe 200 can be activated to selectively treat a target along the same side of the probe. More than one sub-element can be activated to selectively treat a desired angular region disposed about the probe, including a region tending 360 deg. or less. In this regard, the probe can be said to focus energy toward a desired region.

Microelectrode elements 207 are not segmented, therefore one electrode covers the entire circumference of the neurological probe 200. The assembly can include an end cap 209, which covers the end of the cylindrical tubing. The assembly can also include a support tube 215 onto which the microelectrode film can be attached, e.g., by gluing or heating. In this embodiment, each contact of the eight cylindrical contacts 206 is electrically coupled to a respective one of the microelectrodes 204, 207.

Figure 7C:
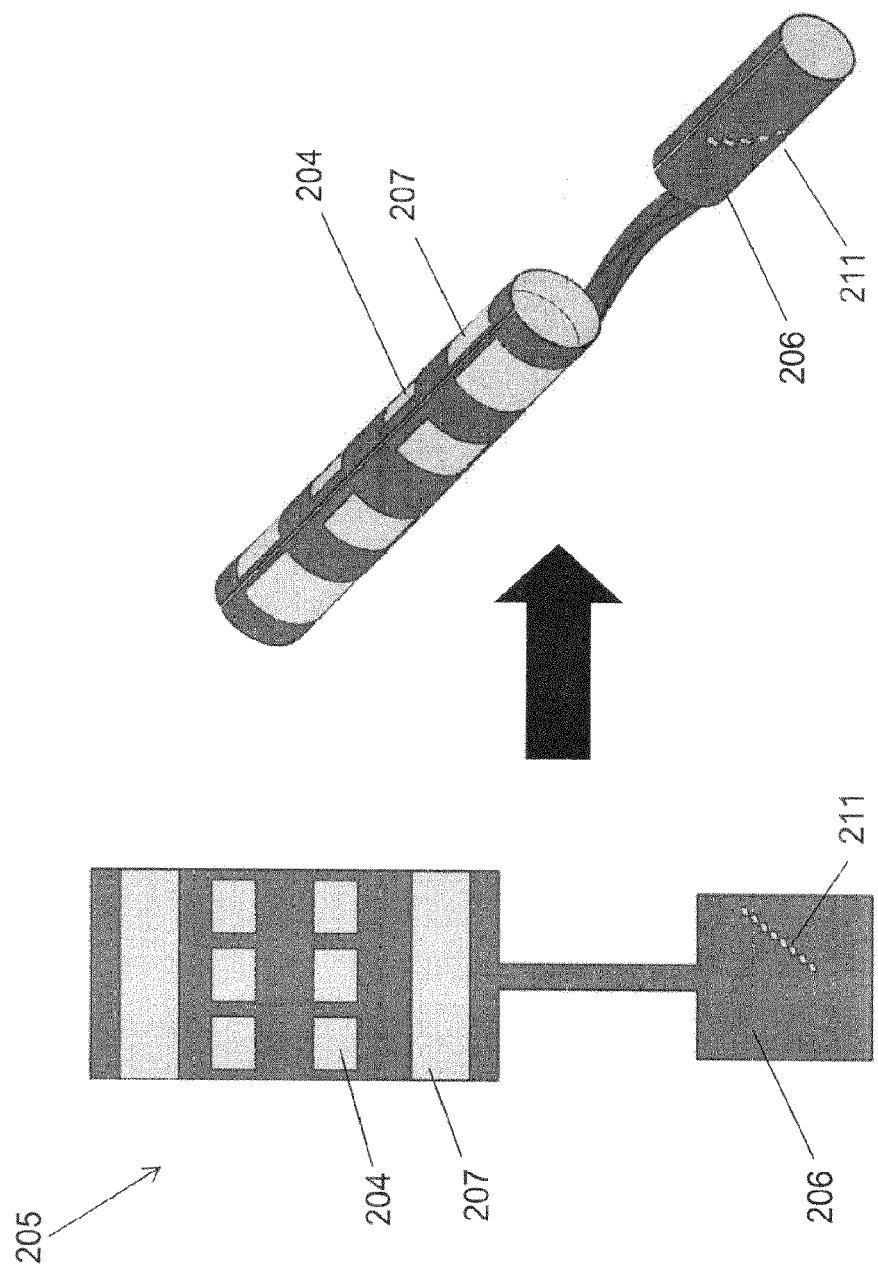
FIG. 7C is an image of a microelectrode array film that forms the distal portion of the microelectrode assembly of FIG. 7A.

FIG. 7C demonstrates the shaping required for the microelectrode film 205 in order to be assembled. The microelectrode film 205 also includes a longitudinal extension 206. The extension 206 incorporates contact pads 211, each pad 211 in electrical communication with a respective one of the microelectrode element 204, 207, for example, through electrical traces. Both the distal and proximal ends of the microelectrode film 205 are reshaped, for example using heating, into a cylindrical shape as shown. Other shapes are possible, depending on the cross-sectional profile of the support tube 218 (e.g., triangular, oval, rectangular).

Figure 7D:
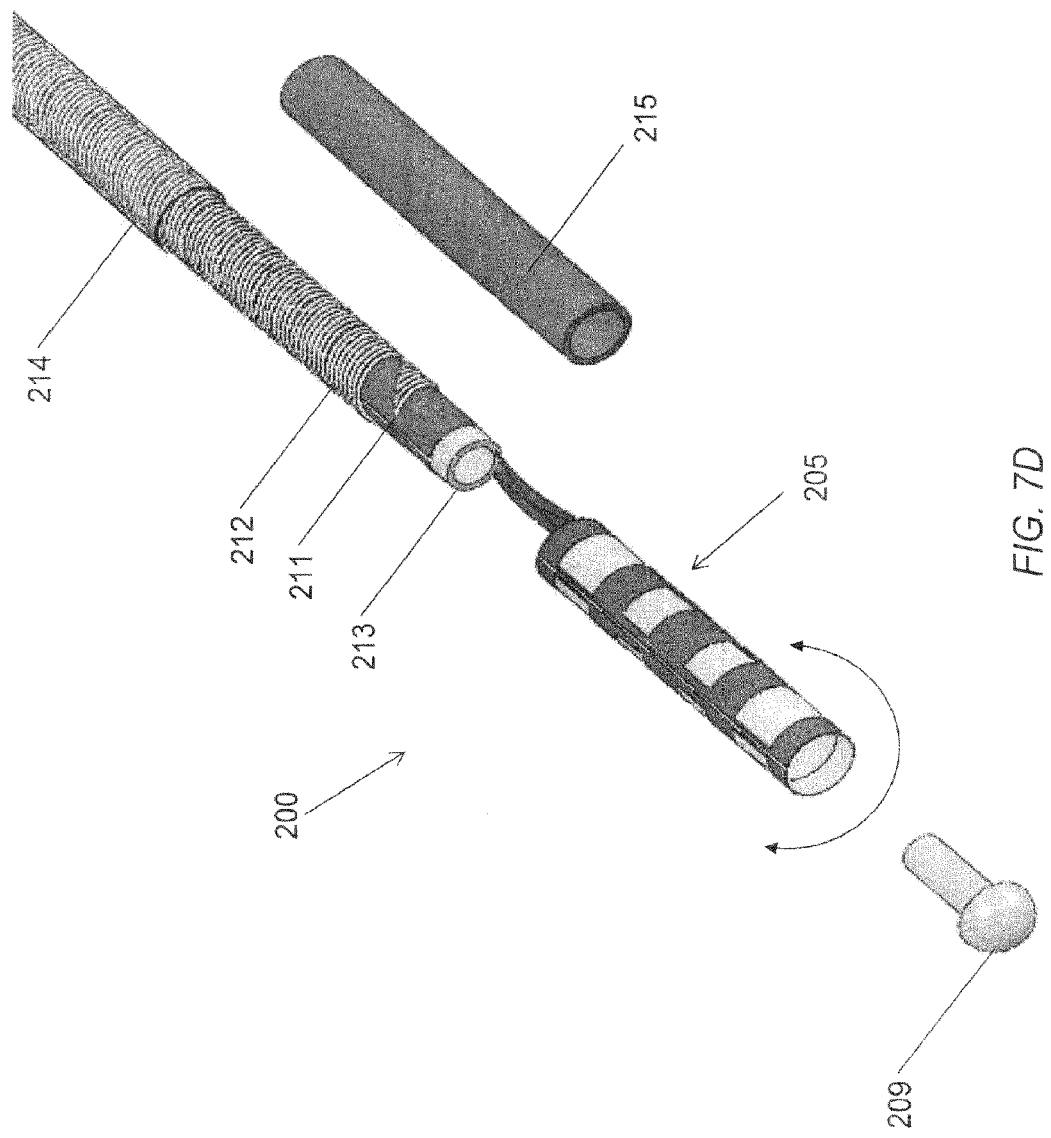
FIG. 7D is an image demonstrating an assembly procedure of the various components that form the microelectrode array of FIG. 7A.

FIG. 7D illustrates the assembly of the neurological probe 200 in more detail. The assembly constitutes two overlapping, concentric cylindrical members 213 and 214. Inner cylindrical member 213 defines a lumen with a typical diameter of 400 μm. The outer diameter can be 1 mm, but must be less than the inner diameter of outer cylindrical member 214. Both cylindrical members 213 and 214 can be composed of a polymeric, rigid or non-rigid (e.g., semi-rigid or flexible) material such as polyurethane or silicone. The assembly also constitutes eight lead wires 212 extending longitudinally in a space defined between the cylinders 213, 216. In some embodiments, the lead wires 212 are helically wrapped around inner cylindrical member 213. Lead wires 212 generally have a diameter of 50-125 μm. The assembly may optionally include a rigid or semi-rigid support tube 215 at its distal end. The tube 215 is used as a support structure onto which the microelectrode film 205 can be attached. The microelectrode film 205 is attached via its contact pads 211 to electrical lead wires 212, each lead wire 212 contacting a respective one of the contact pads 211. The tube 215 can cover these connections adding strength to their structure. The microelectrode film 205 is then wrapped in the direction of the arrow. Finally, end cap 209 covers and seals the cylindrical members 213 and 214. The end cap can be shaped, for example, having a blunt profile, as shown.

FIG. 7E demonstrates an image of an assembled neurological probe 200. The different components described in FIG. 7A through FIG. 7D are visible including the microelectrode array film 205, the inner tubing 213 and the outer tubing 214. In this embodiment the distal support tube 215 has been implemented as a laser cut stainless steel tube.

Figure 8A:
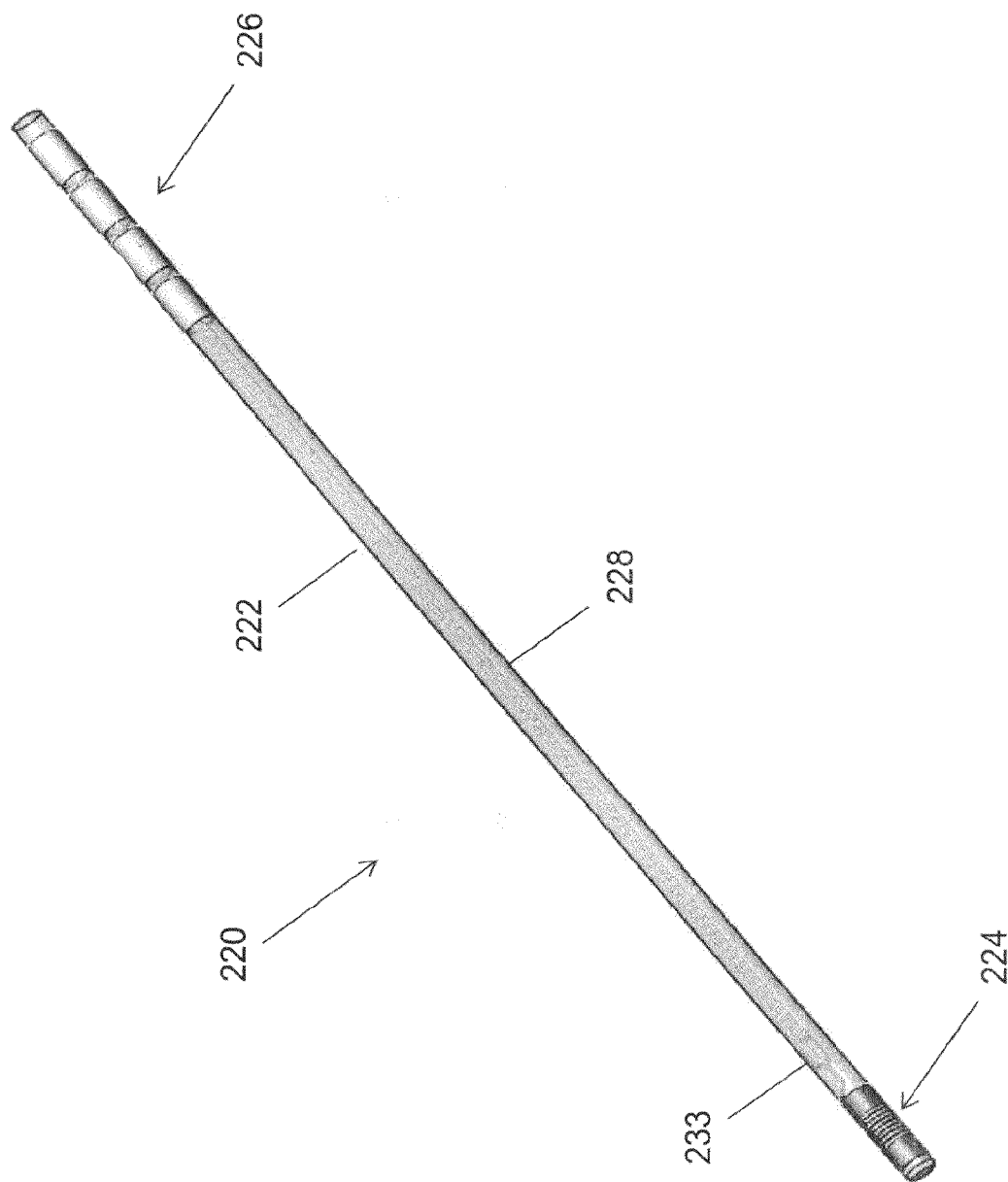
FIG. 8A is an alternative embodiment of an elongated microelectrode assembly.
Figure 8B:
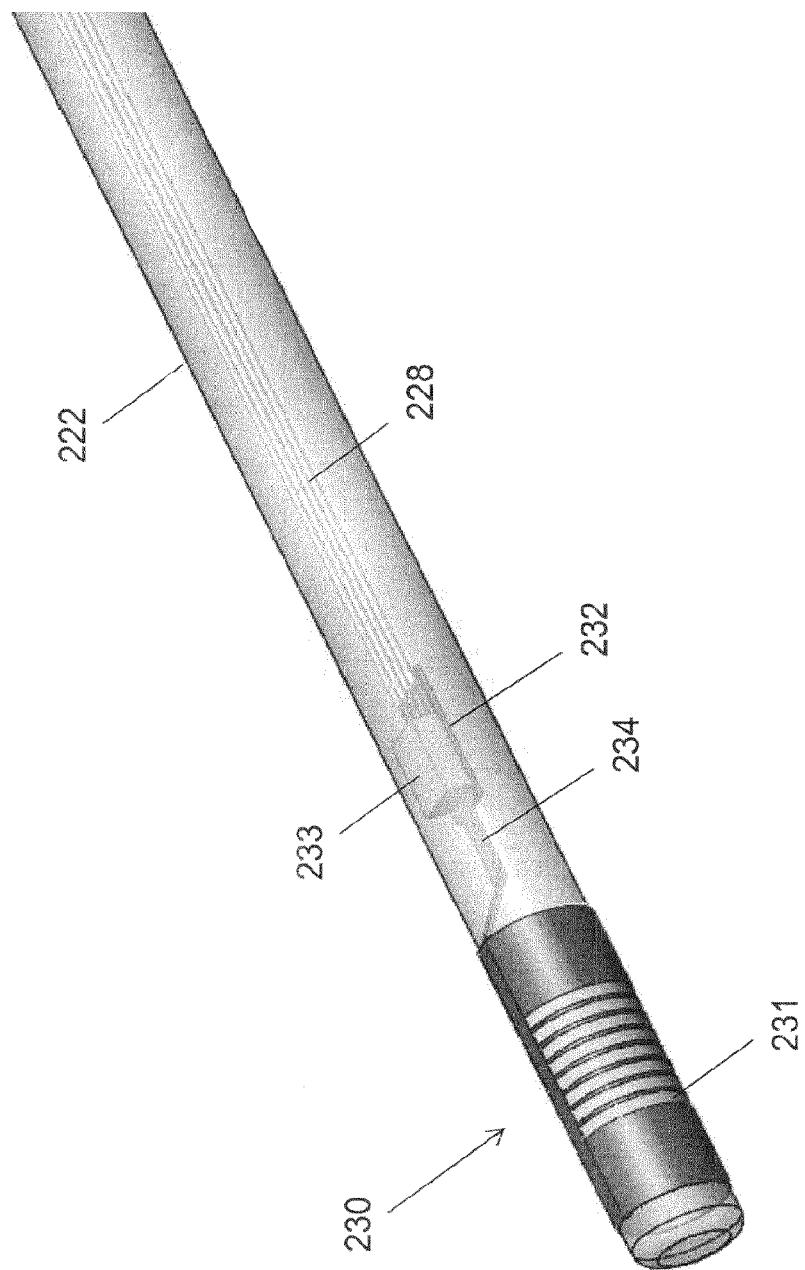
FIG. 8B is a perspective view of a distal portion of the elongated microelectrode assembly of FIG. 8A.

Another embodiment of an elongated microelectrode probe assembly 220 is illustrated in FIG. 8A and FIG. 8B, including a microelectrode array assembly 224. The microelectrode array assembly 224 is positioned at a distal end of an elongated cylindrical member 222. Once again, one or more electrically conductive, cylindrical contacts are positioned at a proximal end of the elongated cylindrical member. As shown, there are four such cylindrical contacts 226. In other embodiments, there may be more or fewer contacts. The microelectrode array assembly 224 also includes a microelectronics assembly 233 positioned along an offset longitudinal extension 232 of the assembly. The longitudinal extension 232 is offset such that the microelectronics assembly 233 is contained within an interior region of the elongated cylindrical member 222, thereby protecting the microelectronics assembly 233 from interaction with the surrounding biological environment. One or more internal electrical conductors 228 extend from the longitudinal extension 232 to one or more of the cylindrical contacts 226.

In more detail, referring to FIG. 8B, the longitudinal extension 232 is also in electrical communication with the conductive electrodes of the microelectrode array 230 through one or more lead traces 234. Also shown are the connections between the internal electrical conductors 228 and a proximal end of the longitudinal extension 232. Thus, in a recording mode, electrical activity from a neurological target can be detected by one or more of the microelectrode contacts 231 of the microelectrode array 230. The electrical signals are then routed through the lead traces 234 to the microelectronics assembly 233. The microelectronics assembly 233 may process the detected electrical signals, for example, through pre-amplification and routing. Ultimately the processed electrical signals detected from the neurological target are routed through the internal electrical conductors 228 to the cylindrical contacts 226. One or more external medical devices such as a recorder may be connected to the elongated microelectrode assembly 220 through the cylindrical contacts 226 for display and or recording of the detected electrical activity.

One or more of the cylindrical contacts 226 can be used to communicate with the microelectronics assembly 233 through one or more of the internal electric conductors 228 in order to remotely or externally control operation of the microelectronics assembly 233. For example, an external signal may be used to select which one or more of the microelectrode contacts of the microelectrode array 230 are selected for recording. In some embodiments recording can be accomplished for all of the microelectrode contacts of the microelectrode array 230.

Alternatively or in addition, the microelectronics assembly 233 may include a multiplexer for combining the signals from more than one of the microelectrode elements 231 onto one of the cylindrical contacts 226. Alternatively or in addition, such multiplexing techniques can be used to combine one or more of the cylindrical contacts 226 to one of the microelectrode elements 231. For example, two contacts 231 can be coupled to one of the distal contacts 226, such that four contacts 226 are sufficient for accessing all eight microelectrode elements simultaneously. Such multiplexing may include any suitable form, such as time division multiplexing, frequency division multiplexing, code division multiplexing, and combinations of one or more of these techniques.

In some embodiments the microelectronics assembly 233 perform at least some level of processing of the detected neurological activity. In some embodiments the microelectronics assembly 233 may be a purely routing device connecting one or more selected microelectrode elements 231 to one or more of the cylindrical contacts 226. Such a microelectronics assembly 233 may be a simple switch or router device. Such routing may include electromechanical switches, reed switches, and electronic switches, such as transistor (e.g., field effect transistor) switches. The switches can be configured in a matrix fashion to allow one or more of the microelectrode elements 231 to be in communication with one or more of the microelectronics assembly 233 and the internal electrical conductors 228 based on a control input signal as may be received from an external source through one or more of the contacts.

In some embodiments, the microelectronic device may include signal conditioning circuitry such as one or more of amplification, filtering, and attenuation. For example, in detection or recording mode, one or more low noise preamplifiers may be included for boosting detected signal level to improve their detectability and recording quality at the cylindrical contacts 226. Such signal conditioning may include one or more of electronic filtering to tailor a frequency spectrum of the detected signal and attenuation. Such electronic filtering can be accomplished with any suitable filter known to those familiar with electronic signal processing. Such filters may include low pass, high pass, band pass and combinations of one or more of these. The filters may be implemented with standard circuit elements, such as inductors, capacitors, and resistors. Alternatively or in addition, at least some of the filters may be implemented using digital signal processing techniques.

Additional processing can be performed to assess the recorded signals and to determine the location of a preferred neurological target. Through careful configuration of the microelectronic contacts in their size, location and configuration, it is possible to locate a target neurological site. For embodiments in which the microelectrode contacts are dimensioned on the order of target neurons it may be possible to record activity of individual neurons independently. The microelectronics assembly 233 may include one or more of an Application-Specific Integrated Circuit (ASIC), commonly available electronics modules, such as microprocessors, electronic memory elements, communications devices, combinational logic, power conditioning, and the like.

Figure 9:
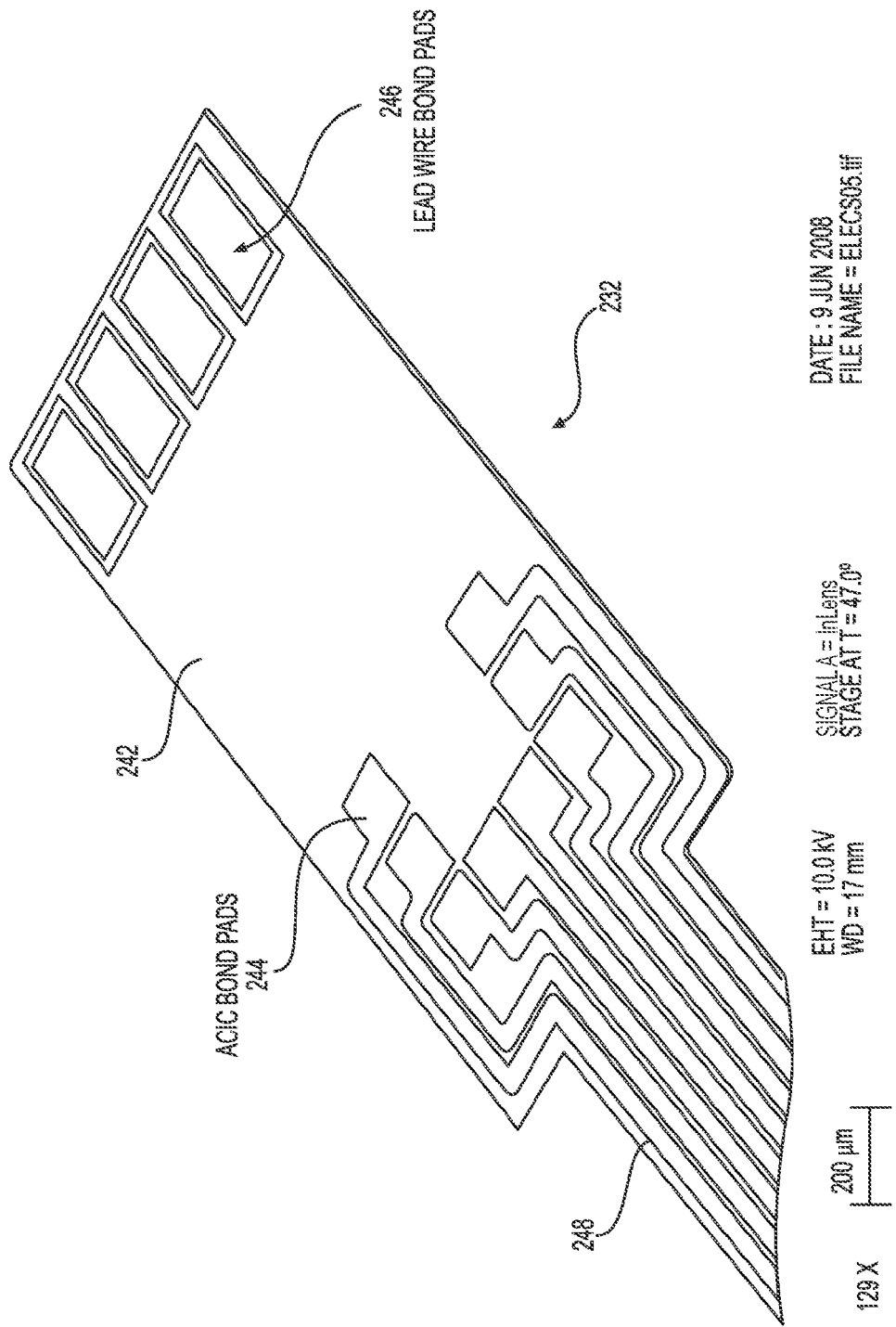
FIG. 9 is a detailed perspective view of a distal portion of an embodiment of a microelectrode array micro-electromechanical system (MEMS).
Figure 10:
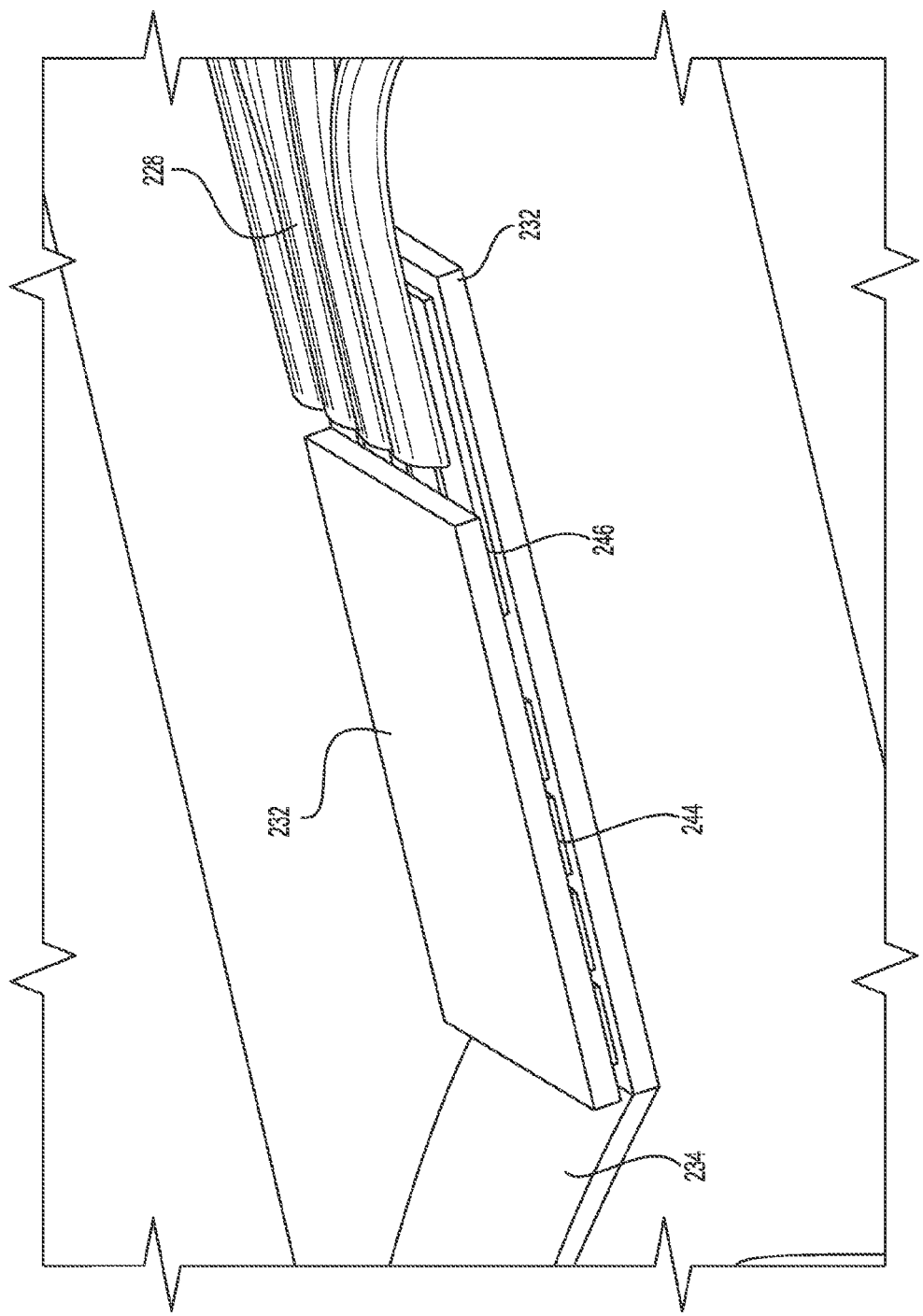
FIG. 10 is a perspective view of the distal portion of an assembly including the microelectrode array of FIG. 9.

An exemplary longitudinal extension of a MEMS film device is illustrated in FIG. 9. The longitudinal extension 232 includes a planar film substrate 242. The substrate 242 includes a first group of one or more electrical contacts in the form of bonding pads 244, sized and positioned to accommodate one or more devices of the electronics assembly 230 (FIGS. 8A, 8B). The substrate 242 also includes a second group of one or more additional electrical contacts in the form of wire bonding pads 246, sized and positioned to accommodate interconnection to one or more of the interconnecting lead wires 228. At least some of the bonding pads 244 of the first group are coupled to respective lead wire traces 248 interconnecting the bond pads 244 to respective ones of the microelectrode contacts 231. As illustrated in FIG. 10, the longitudinal extension 232 includes the microelectronics assembly 233 housed thereon and the interconnecting lead wires 228 coupled to the second group of bonding pads 246.

Another embodiment of an elongated microelectrode probe assembly 420 is illustrated in FIG. 11A and FIG. 11B. The assembly 420 includes a microelectrode array assembly 260 at a distal tip of the probe assembly 420 as shown. This microelectrode array assembly 260 can be any microelectrode array including any of the microelectrode arrays described herein. The assembly 420 also includes one or more cylindrical contacts 426a, 426b, 426c, 426d (generally 426) at a proximal end, as shown. The microelectrode array assembly 260 and cylindrical contacts 426 are disposed along a flexible elongated cylindrical member 422. The cylindrical member 422 includes an elongated open-ended lumen 424, accessible from an open end 430 located at a proximal end of the probe assembly 420.

One or more internal electrical conductors 428 extend from the microelectrode array assembly 260 to the one or more cylindrical contacts 426. The internal electrical conductors are configured so as not to interfere with interior volume of the open ended lumen 424 or with flexibility of the elongated cylindrical member 422. In the illustrated embodiment, four such electrical conductors 428 are shown extending helically along the length of the elongated cylindrical member, between the microelectrode array assembly 260 and the cylindrical contacts 426. These helically wound internal electrical conductors 428 reside within the material of the flexible elongated cylinder 422 between an exterior surface and an interior wall of the open ended lumen 424.

Beneficially, an elongated rigid guide member, such as a stylet, or trocar (not shown) can be inserted into an open end 430 of the open ended lumen 424 extending along a substantial length of the elongated flexible cylindrical member 422 to provide temporary rigidity as may be necessary during insertion and/or removal procedures of the elongated electrical probe assembly 420. When employed during an insertion procedure, such a stylet provides rigidity as the elongated electrical probe assembly 420 is inserted into a neurological target site. Once inserted at the target site, the stylet can be removed from the proximal open end 430. The remaining elongated electrical probe assembly 420 remains positioned at the target site, while also providing substantial flexibility along its extended length. Such flexibility offers advantages for patient comfort and response to any movement of the local anatomy to promote prolonged placement of the microelectrode array assembly 260 at the neurological target site. The stylet may be configured as a straight element. In some embodiments, at least a portion of the stylet may include a non-linear region, such as a curve, as may be beneficial to facilitate insertion and/or removal of the elongated electrical probe assembly 420.

As shown, the microelectrode array assembly 260 extends for a length 'T' along longitudinal axis. The elongated flexible cylindrical member 422 has a diameter 'D'. Four cylindrical contacts 426 at the proximal end can provide access to power 426a, electrical ground 426b, control 426c, and signal or data 426d.

A more detailed view of a distal portion of the elongated electrical probe assembly 420 shown in FIG. 11B illustrates distal ends of each of the helically wound internal electrical conductors 428, connected to respective lead wire bonding pads 436 as may be provided on a longitudinal extension 434 of the microelectrode array assembly 260. Also visible is the distal portion of the open ended lumen 424, having a distal end 432 located relatively close to a proximal end of the longitudinal extension 434. Thus, the open ended lumen 434 extends along nearly the entire length of the elongated flexible cylindrical member 422. When the stylet is inserted within the open ended lumen 424 and extends toward the distal end 432, the elongated flexible cylindrical member 422 has temporary rigidity along substantially its entire length.

Figure 11C:
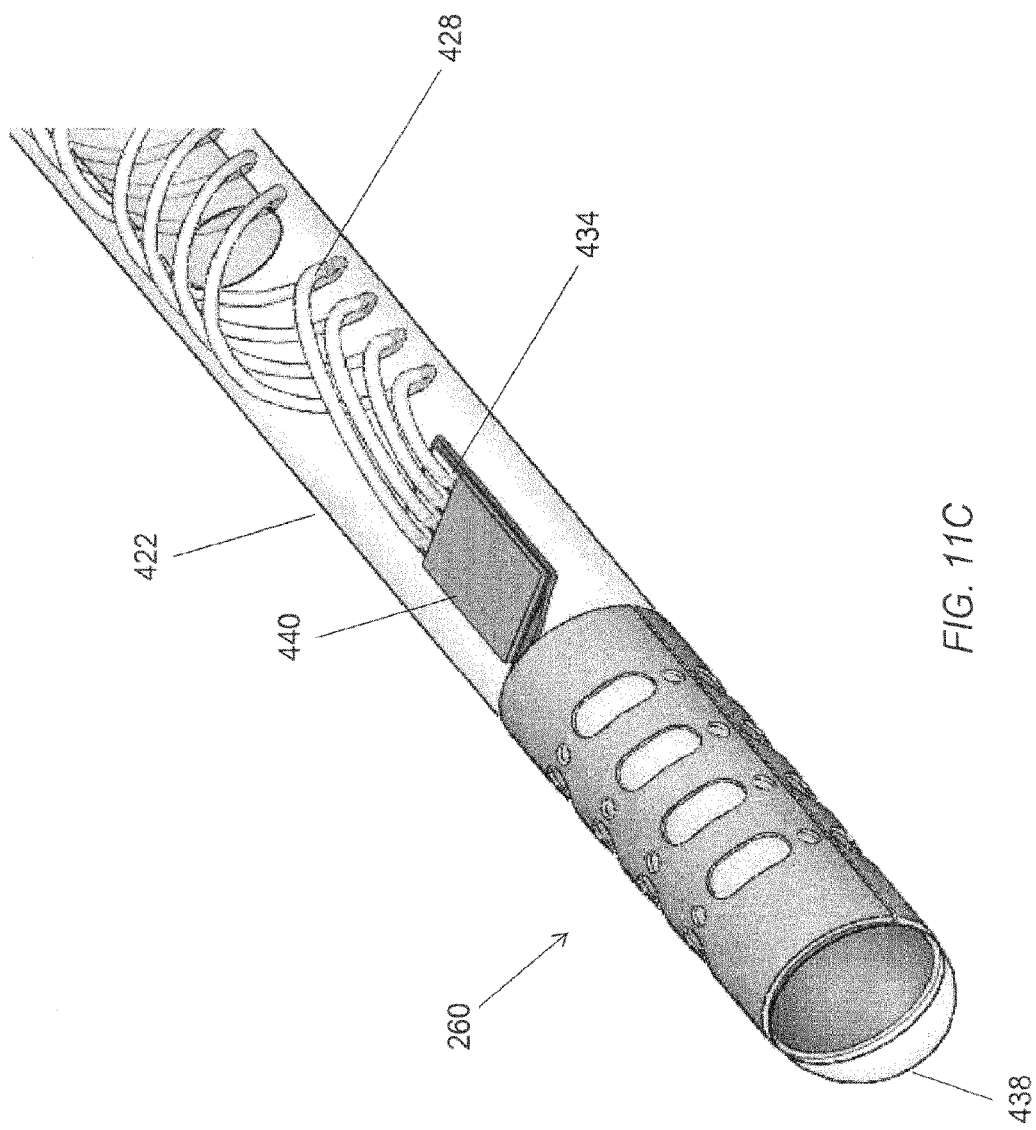
FIG. 11C is a more detailed view of a distal portion of the elongated microelectrode assembly illustrated in FIG. 11A.

A more detailed illustration of an embodiment of the distal end of the elongated probe assembly 420 is shown in FIG. 11C. The device includes a microelectrode array 260, located adjacent to the distal tip 438. The microelectrode array assembly 260 includes a longitudinal extension 434 housing one or more microelectronic devices 440 and including electrical contacts, each in respective communication with one of the internally electrical conductors 428.

Figure 11D:
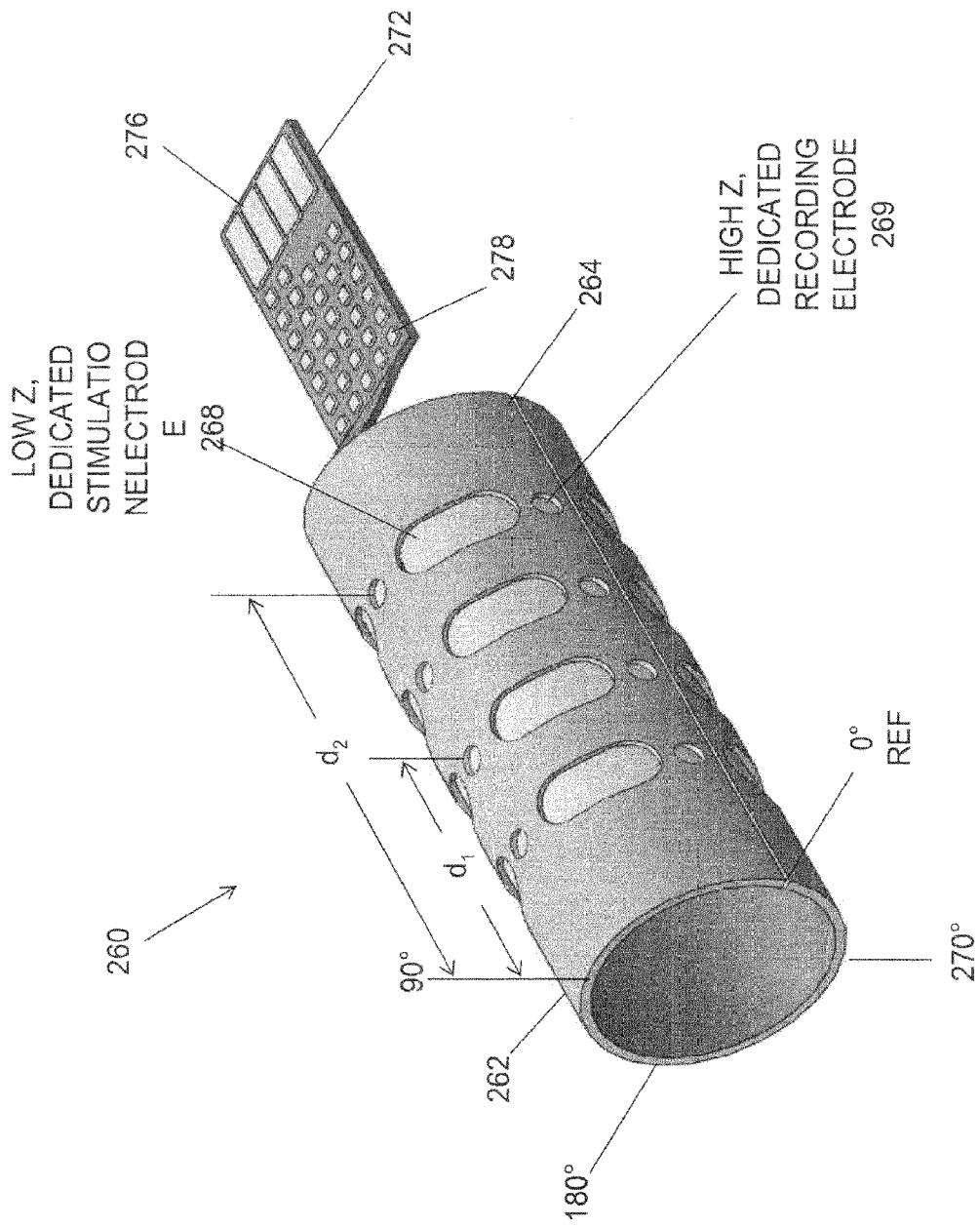
FIG. 11D is a perspective view of the microelectrode array of FIG. 11A.

A more detailed illustration of the assembled microelectrode film 260 is illustrated in FIG. 11D. The assembly 260 includes a hollow cylindrical substrate 262. The exemplary embodiment includes sixteen semi-annular microelectrodes 268 arranged in annular sub-arrays positioned at respective distances along a longitudinal axis of the cylindrical substrate 262 for example being measured from a distal end. In the exemplary embodiment, each annular sub-array includes four stimulation electrodes 268 and four recording electrodes 269. Other numbers of sub-array elements are possible, and it is not necessary that the number of stimulation electrodes 268 be equivalent to the number of recording electrodes 269 for any given sub-array. In some embodiments, each sub-array is identical, while in other embodiments, they differ.

In some embodiments, each stimulation electrode element 268 extends along an arc length greater than 10° but less than 180°. Each recording electrode 269 extends along an arc length substantially less than 90° such that the combination of stimulation electrode elements 268 and recording electrode elements 269 are disposed about 360° of the cylindrical substrate 262 with suitable spacing provided between each of the adjacent elements 268, 269. As illustrated, the stimulation electrode elements 268 appear as stripes located about their respective distances along the central axis; whereas, the recording electrodes appear as small circles, or dots.

The particular shape of the recording electrode elements 269 can be circular, elliptical, polygonal, such as squares, triangles, diamonds, hexagons, and the like. The shape of the stripe ends of the stimulation electrode elements 268 adjacent to the recording electrode 269 may be angular (e.g., square) or curved. As shown in the figure, a reference angle is measured with respect to a seam at 0° extending around the circumference. The recording electrodes 269 are located adjacent to the seam 264 at approximately 0°. A second recording electrode located opposite to the first resides at approximately 90°. Likewise, the stimulation electrode element 268 is centered at approximately 45°, between approximately 15° and 75°. A second stimulation electrode 268 is located centered at 135° and also extending between approximately 105° and 165°. A third recording electrode 269 is located at approximately 180°. A third stimulation electrode 268 is located centered at 225°, extending between approximately 195° and 255°. A fourth recording electrode 269 is located at approximately 270°. A fourth stimulation electrode 268 is located centered at 315° extending between approximately 285° and 345°.

Also shown is a longitudinal extension to the substrate 272 including in this example thirty two electronic device contacts 274, each one in electrical communication with a respective one of the dedicated recording or dedicated stimulating electrodes via interconnecting lead traces. Also disposed on the longitudinal extension 272 are one or more wire lead contacts 276. In the illustrative example, four such wire lead contacts 276 are provided.

Figure 12:
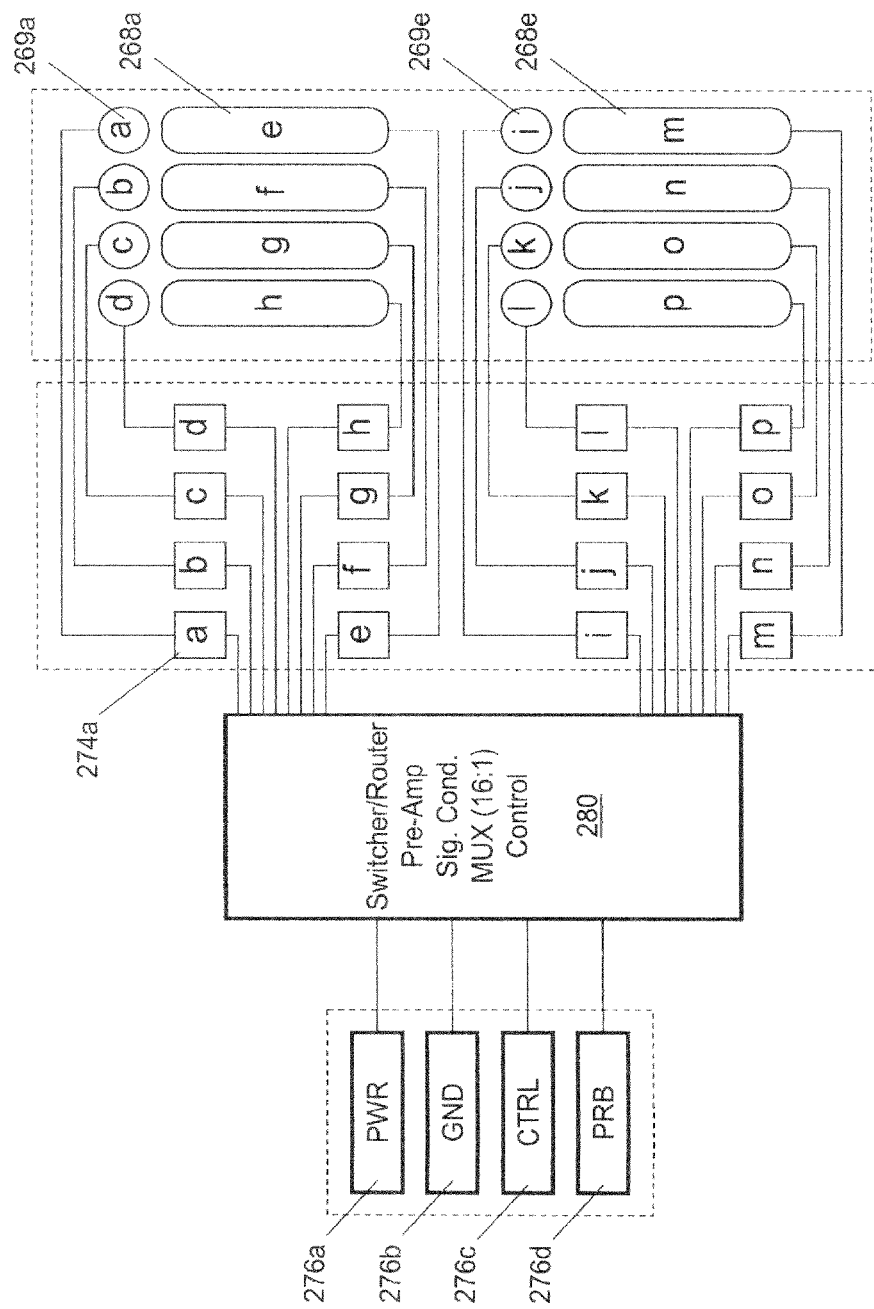
FIG. 12 is a schematic diagram of an exemplary microelectrode array circuit.

Illustrated in FIG. 12 is an electronic circuit schematic diagram for half of the microelectrode array assembly 260 shown in FIG. 11D. Shown along the right hand portion of the schematic diagram are the eight of the sixteen stimulation electrode elements 268a through 268h (generally 268). Each one of these elements 268 is in electrical communication with a respective electronic device contact 274a through 274d and 274m through 274p (generally 274). Also illustrated along the right hand portion of the schematic diagram are eight of the sixteen recording electrode elements 269a through 269h (generally 269). Similarly, each of the recording electrode elements 270 is in electrical communication with a respective electronic device contact 274e through 274h and 274j through 274l. For illustrative purposes, the schematic diagram includes a representative electronic device 280. For brevity, the schematic diagram includes only eight recording and eight stimulation contacts but a full schematic diagram for all thirty-two contacts is similar. In this electronic device may include one or more of a switch or router, a preamplifier, a signal conditioner, a multiplexer, and a controller. The electronic device 280 is in electrical communication with all sixteen of the electronic device contact elements 274a through 274p.

The electronic device 280 is in further communication with each of the four wire lead contacts 276a through 276d (generally 276). In the illustrative example, the first wire lead contact 276a is used for supplying electrical power to the microelectronic device and/or one or more of the stimulation electrode elements 268. The second wire lead contact 276b is used to provide an electrical ground contact. This ground contact 276b may include earth ground, another electrical ground within the system, such as a chassis ground of a medical device connected to the electronic device 280, or simply a signal return line. A third wire lead contact 276c corresponds to a control signal that may be used to provide control inputs from an operator or other medical device, to control configuration and/or operation of the electronic device 280. Alternatively or in addition, the control signal contact 276c may be used for control signals from the electronic device 280 to another medical device. A fourth wire lead contact 276d corresponds to a signal contact as may be used for directing electrical activity detected by one or more of the recording electrode elements 269 to a recording or display device. Alternatively or in addition, the signal contact 276d may be used for directing electrical stimulation signals from another medical device to one or more of the stimulation electrode elements 268.

Referring again to FIG. 11D, the stimulation electrodes 268 are configured to have a relatively low electrical impedance; whereas, the recording electrodes 269 are configured to have a relatively high electrical impedance. A relatively low impedance stimulation electrodes 268 are therefore well suited for transfer of electrical charge transfer to surrounding tissue at a neurological target site. Also, the relative high impedance recording electrodes 269 allow for detection of electrical activity from a neurological target site.

Figures 13A, 13B:
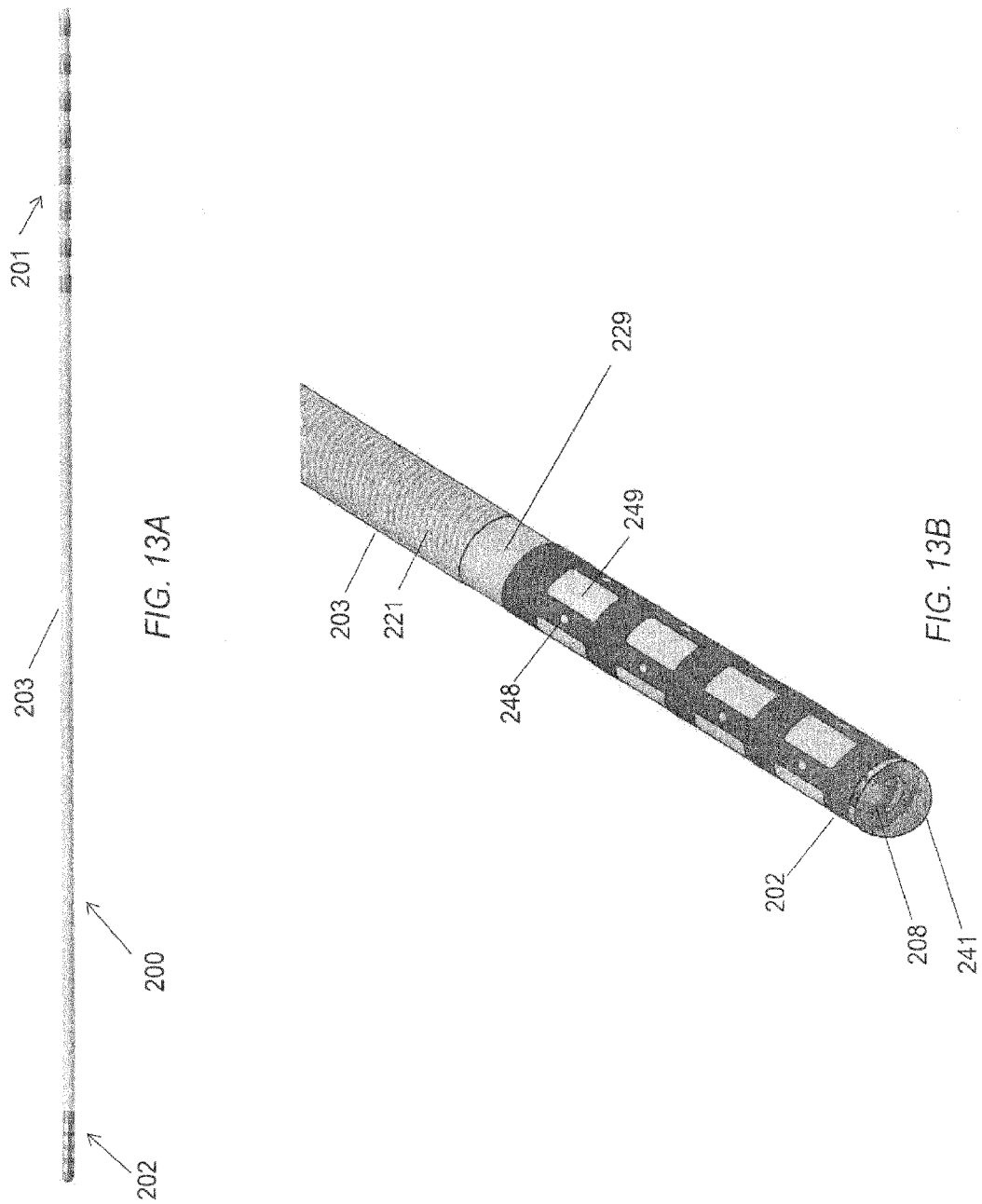
FIG. 13A is a planar view of an elongated microelectrode assembly.
FIG. 13B is a perspective view of a distal portion of the elongated microelectrode assembly in FIG. 13A.

FIG. 13A displays an additional embodiment of a neurological probe 200, incorporating embedded microelectronics. The neurological probe 200 incorporates a microelectrode film 202, and cylindrical member 203 composed of two concentric cylindrical tubes, and eight electrical contacts 201 that permit electrical connection from the distal end to the proximal end through eight lead wires wrapped around the inner cylindrical member.

FIG. 13B provides a more detailed view of an embodiment of the distal end of the neurological probe 200. The metallic stimulation electrode 248 has dimensions in this example of about 1000 µm in length, and 600 µm in width. In some embodiments, the length measured along the longitudinal axis can range from 2 µm to 2 mm. In some embodiments, the width may cover the entire circumference, and can range from 2 µm to 4 mm. The metallic recording electrode 249 has dimensions in this example of 150 µm in diameter. It is generally smaller than the stimulation electrode 248.

The distal end incorporates a support tube 229, that serves as a support structure for the microelectrode film 202 and as a protective enclosure for the microelectronic circuit and connections within. In this example the tube 229 has a length of 8 mm, an inner diameter of 1.05 mm, and an outer diameter of 1.25 mm. It may be implemented in a rigid, or semi-rigid material such as stainless steel, or a biocompatible polymer such as PEEK (polyetheretherketone).

The embodiment also demonstrates the outer cylindrical member 203 which is implemented with an outer diameter of 1.27 mm, and an inner diameter of 1.05 mm. It is generally implemented in polyurethane or silicone. Along its lumen are wrapped the lead wires 221 that electrically connect the proximal and distal ends of the neurological probes. The outer cylindrical member 203 can be connected to the support tube 229 by form fitting or gluing.

The embodiment also demonstrates an end-cap 241 which can be implemented as a plug to seal the ends of the two concentric tube structures. The microelectrode film 202 is connected to the inner volume by an extension 208 that leads to the embedded microelectronic element and lead wires 221.

Figure 13C:
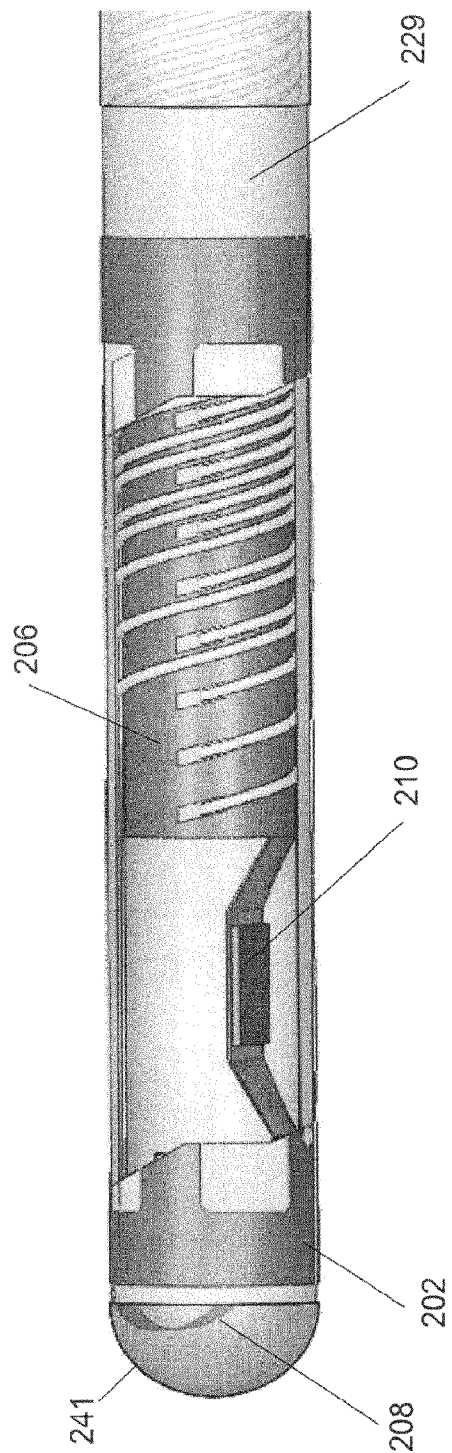
FIG. 13C is a cutaway view of the distal portion of the elongated microelectrode assembly in FIG. 13A illustrating the interior components.

Referring now to FIG. 13C, a cutaway view of the distal end of the neurological probe 200 is provided in order to identify the microelectrode element at its interior. The longitudinal extension is offset from an external surface of the cylindrically formed substrate 202 such that the longitudinal extension 206 and any microelectronic devices 210 mounted thereon would be containable within an interior region of the elongated cylindrical member housing the formable film substrate 202. In the illustrative embodiment, the formable film substrate 202 including the conductive electrodes is wrapped around a cylindrical body 229 located at the distal end of the neurological probe. For applications including multiple electrode rings, a selection circuit, such as a switch or router, can be included to selectably route stimulation or recording signals to/from one or more of the microelectrode rings thereby stimulating or recording from a selectable location within the neurological target depending upon which microelectrode ring(s) is in use. Such stimulation signals may be routed from the implantable pulse generator 122 (FIG. 2) and applied to a chosen microelectrode ring.

Figure 13D:
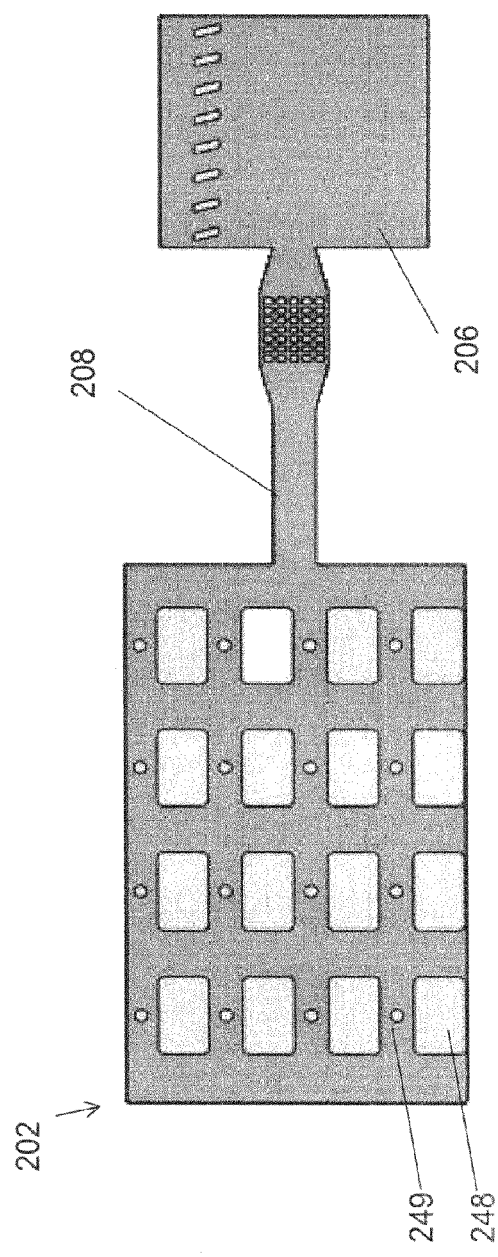
FIG. 13D is a planar view of an embodiment of a microelectrode film assembly for use with the neurological probe of FIG. 13A.

As shown in FIG. 13D, the microelectrode film can be initially formed as a flat element onto which a microelectronic circuit element is mounted before, or after, it is assembled into two concentric cylinders. The longitudinal extension 206 can be configured to accommodate one or more microelectronic devices 210. One or more of any such microelectronic devices 210 included thereon can be in electrical communication with one or more of the microelectrode elements 248 and 249 through one or more interconnecting conductive electrical traces 208.

Figure 14A:
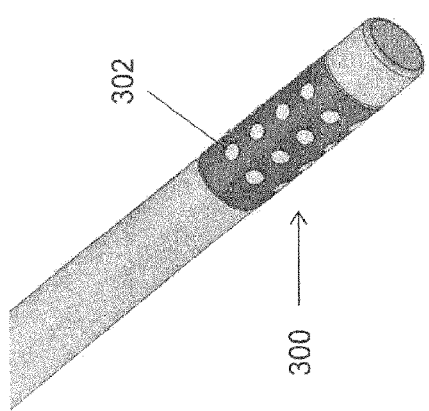
FIG. 14A is a perspective view of a distal portion of another embodiment of an elongated microelectrode assembly.

Various configurations of the microelectrode elements are illustrated in FIG. 14 through FIG. 15. Referring first to FIG. 14A, a microelectrode array 300 is illustrated placing many relatively small microelectrodes 302 around a central cylinder. In the exemplary embodiment, eight such elements 302 are located at respective positions around 360° circumference of the cylinder, forming an annular microelectrode pattern 303. In some embodiments, the angular displacement between adjacent elements may be uniform as shown (e.g., eight elements spaced apart from each other by 45°). Alternatively or in addition, the angular displacement between at least some of the adjacent elements 302 of the annular microelectrode pattern 303 may be non-uniform. Additional annular patterns of elements can be positioned along the cylinder. For example, the same pattern can be repeated at different distances along the cylinder as measured with respect to an end of the array 300. The distance between adjacent annular patterns 303 may be uniform. Alternatively or in addition, the distance between adjacent annular patterns 303 of the microelectrode array 300 may be non-uniform. In the exemplary embodiment, there the array 300 includes four identical annular patterns 303 uniformly spaced apart along the central cylinder.

In the exemplary embodiment, the annular microelectrode pattern 303 includes eight microelectrode 302 discs, each having a diameter of about 300 µm, uniformly distributed and wrapped around a 1.27 mm diameter cylinder. The microelectrodes 302 could be other shapes, such as ellipses, polygons, such as squares, triangles, diamonds, hexagons, and the like. One or more of the shapes and sizes of the microelectrodes 302 may vary within the annular microelectrode pattern 303. For example, sizes may range from 2 µm or less, to 1 mm or larger. The electronics required to apply electrical signals to the microelectrode sites, or to record neural activity from the sites, are embedded within the central cylinder.

Figure 14B:
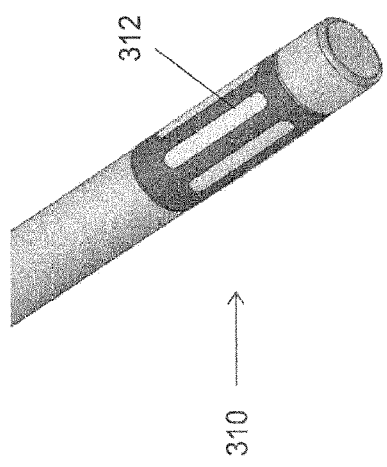
FIG. 14B is a perspective view of a distal portion of yet another embodiment of an elongated microelectrode assembly.

An alternative embodiment of the invention illustrated in FIG. 14B shows several microelectrode elements 312 configured lengthwise, extending along a longitudinal axis of the cylinder and disposed at respective angles measured about a circumference of the cylinder. In the exemplary embodiment, each microelectrode element 312 is a strip having a diameter of about 300 µm and length of approximately 1.88 mm, extending along the length of the cylinder. Eight such elongated strip microelectrode elements 312 are uniformly distributed and wrapped around a 1.27 mm diameter cylinder. The ends of the microelectrodes may be angular (e.g., square) or rounded as shown. The dimensions of the elongated strip microelectrode elements 312 may range in width from 2 µm or less, to 1 mm or larger. They may range in length from 2 µm or less, to 3 mm or longer.

FIG. 15A through FIG. 15J represent various embodiments of microelectrode arrays. Each of the microelectrode arrays is illustrated in a planar representation. For cylindrical applications, these planar representations would be folded about the cylindrical structure having a longitudinal axis extending vertically with respect to the planar representation, such that the left and right sides of the planar structure meet along a seam. Also illustrated along the top of each figure are reference angular positions varying from 0° to 360°. A first microelectrode array 320 illustrated in FIG. 15A includes a formable planar substrate 324 including multiple horizontal electrically conductive stripes 322a through 322d (generally 322). When formed in a cylindrical fashion, these horizontal stripes represent cylindrical microelectrode elements 322. As illustrated, each of the electrically conductive stripes 322 is located at a respective distance '$d_{1a}$' measured from one of the ends of the formable planar substrate 324 along the longitudinal (vertical) axis. Each of the electrically conductive stripes 322 has a respective width '$w_1$' and center to center spacing with respect to neighboring conductive stripe 322 of '$s_1$'.

Figure 15A:
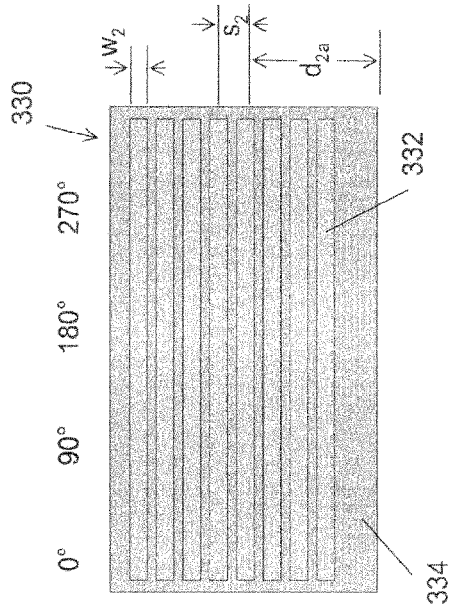
Figure 15B:
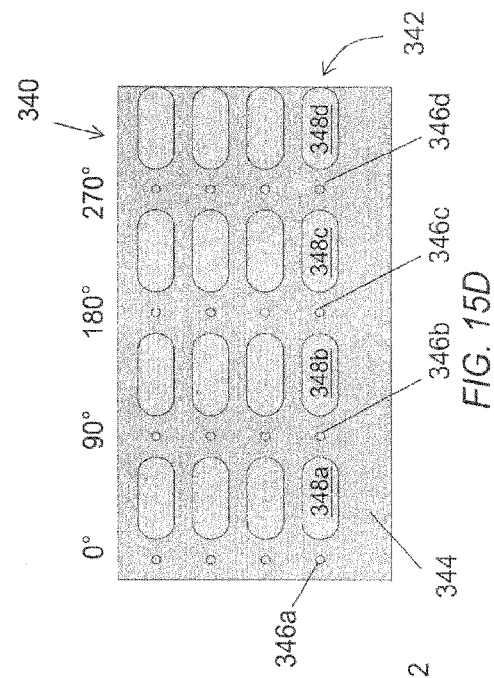

Another embodiment of a microelectrode array 330 is illustrated in FIG. 15B. This microelectrode array 330 also includes a number of horizontal electrically conducting stripes 332. With respect to the stripes 322 of FIG. 15A, these stripes 332 have a narrower width $w_2$, a closer center to center spacing $s_2$, and are larger in number. In some embodiments it would be possible to include electrically conducting stripes having one or more of various different widths and different spacing. In some embodiments the eight microelectrode strips 332 are connected to eight respective bond pads (not shown). In yet additional embodiments, the eight microelectrode strips 332 are connected to four bond pads (not shown), resulting in two adjacent strips being in electrical contact.

It is advantageous in at least some instances to treat a target region with a probe having a greater number of edges. Edges offer certain advantages in controlling charge and/or current distributions. To this end, a microelectrode of a given surface area, can be configured to increase its perimeter. This can be accomplished, for example, by controlling shapes of the microelectrodes. Thus, rather than a simple rectangular arrangement, a microelectrode can have a folded shape (e.g., a "U" or and "S" or even a comb-like shape). In at least some embodiments, more than one microelectrode are energized by a common source (e.g., through a common bonding pad). For example, two or more of the microelectrode strips 332 can be connected to the same respective bond pad. Thus, the eight strips 332 can be controlled through only four bonding pads.

Figure 15C:
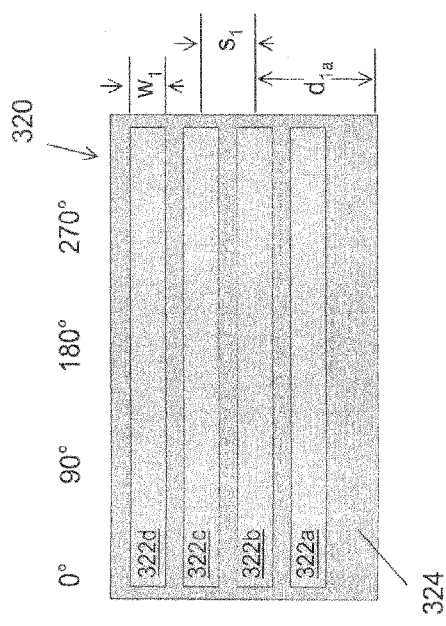

FIG. 15C illustrates the microelectrode array 350. In the illustrative example, the microelectrode array 350 includes four horizontal annular patterns 356a through 356d (generally 356). Each horizontal annular pattern 356 includes a first high-impedance element 356a, located at approximately 0° and a second high-impedance element 356b, located at approximately 180°. A first low-impedance microelectrode element 358a is located between the two high-impedance microelectrodes 356a, 356b. A second low-impedance microelectrode element 358b is located to the right of high-impedance microelectrode element 358b. When formed into a cylinder, the two high-impedance microelectrodes 356a, 356b oppose each other, as do the two low-impedance electrodes 358a, 358b. In the exemplary embodiment, the annular pattern 352 is repeated at three other different distances measured with respect to the bottom edge of the formable planar substrate 354. Other embodiments having more or less annular patterns can be included. Such a configuration is useful for increasing microelectrode edges in contract with each bonding pad.

Figure 15D:
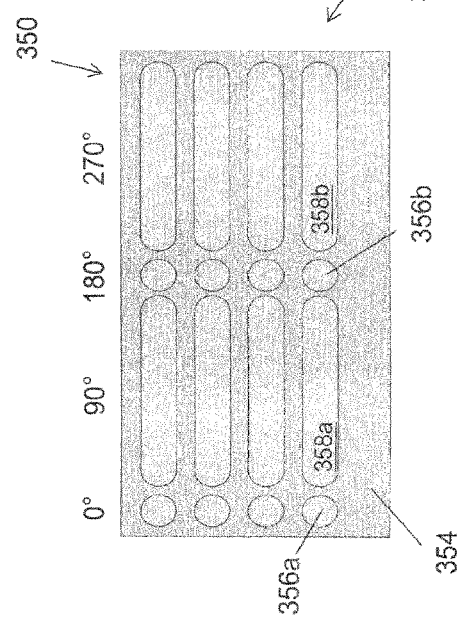

Another embodiment of a microelectrode array 340 is illustrated in FIG. 15D, similar to that shown in the microelectrode array assembly 260 of FIG. 11D. This microelectrode array 340 is similar to the microelectrode array 350 illustrated in FIG. 15C, except that each of the low-impedance microelectrode elements have been split into two low-impedance microelectrode sub-elements 348a, 348b and 348c, 348d. In some embodiments the microelectrode sub-elements 348 are electrically isolated from each other, requiring separate bond pads for each element. In some embodiments, one or more microelectrode stimulation elements 348 are electrically connected, requiring only one bond pad to transmit a signal to several elements. Additionally, there are in total sixteen microelectrode recording elements 346. In yet another embodiment of a microelectrode array illustrated in FIG. 15E, each annular pattern 372 includes four high-impedance microelectrode elements 376a through 376d (generally 376) respectively located at approximately 0°, 90°, 180°, and 270°. Each of four relatively low-impedance microelectrode elements 378a through 378d (generally 378) is located between adjacent pairs of high-impedance microelectrode elements 376. In this embodiment the microelectrode recording elements 376 are larger and will therefore have different electrical recording characteristics than those demonstrated in FIG. 15D. A planar representation of the microelectrode array illustrated in FIG. 14A is shown in FIG. 15F. The microelectrode array 360 includes four horizontal annular patterns, each including eight circular microelectrode 366 elements arranged on a formable planar substrate 364.

FIG. 15G illustrates a planar version of the microelectrode array 310 shown in FIG. 14B. This microelectrode array 390 includes eight elongated, vertically conducting microelectrode stripes 392 arranged at uniform spacing between 0° and 360° along the formable planar substrate 394. FIG. 15H illustrates yet another microelectrode array 380 including combinations of the elongated, vertically conducting microelectrode stripes 386 and circular microelectrode elements 384 arranged at respective longitudinal distances along the formable planar substrate 384.

Another microelectrode structure is illustrated in FIG. 15I, having an arrangement similar to that shown in FIG. 15C, in that it includes two opposing elongated horizontal electrically conducting microelectrode elements 408a, 408b. However, each of the high-impedance contacts 356 of FIG. 15C has been replaced by a respective tetrode 406. Each tetrode 406 includes an arrangement of four microelectrode elements 410.

Another microelectrode structure is illustrated in FIG. 15J, having an arrangement similar to that shown in FIG. 15A, in that it includes elongated horizontal electrically conducting microelectrode stimulation elements 418a, 418b, 418c. However, between each microelectrode strip 418, and above the superior strip 418a, and below the inferior strip 418c, is an array of microelectrode recording elements 419a, 419b, 419c, and 419d, or generally 419. These microelectrode recording elements 419 permit recording at different depths in the brain, with respect to the microelectrode stimulation element 418. In some embodiments, the microelectrode stimulation element 418 is segmented into three, or four parts, as demonstrated in FIG. 15D and FIG. 15E. In some embodiments the microelectrode stimulation elements 418 are electrically isolated from each other, requiring separate bond pads for each element. In some embodiments, one or more microelectrode stimulation elements 418 are electrically connected, requiring only one bond pad to transmit a signal to several elements.

FIG. 16A through FIG. 16D and FIGS. 17A and 17B illustrate cutaway views of alternative assembly methods for attaching microelectrode films to the distal ends of neurological probes. These assembly methods can be used for microelectrode films that incorporate microelectronics, or that do not incorporate microelectronics. The neurological probes described herein can be assembled using any one of, or a combination of, the techniques described in FIG. 16A through FIG. 16D, and FIGS. 17A and 17B.

Figure 16B:
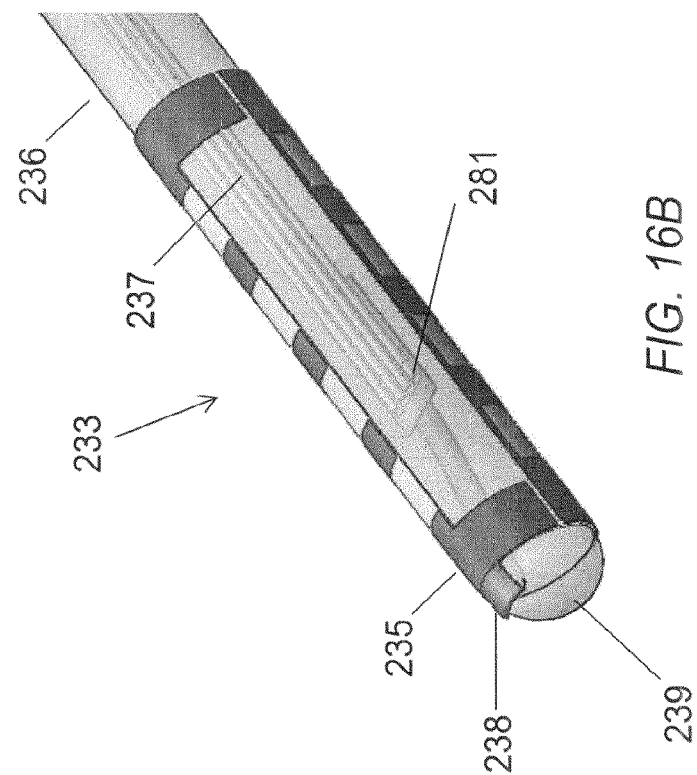
FIG. 16A through 16D are cutaway views demonstrating alternative assembly methods of a distal portion of an embodiment of a microelectrode array.
Figure 16A:
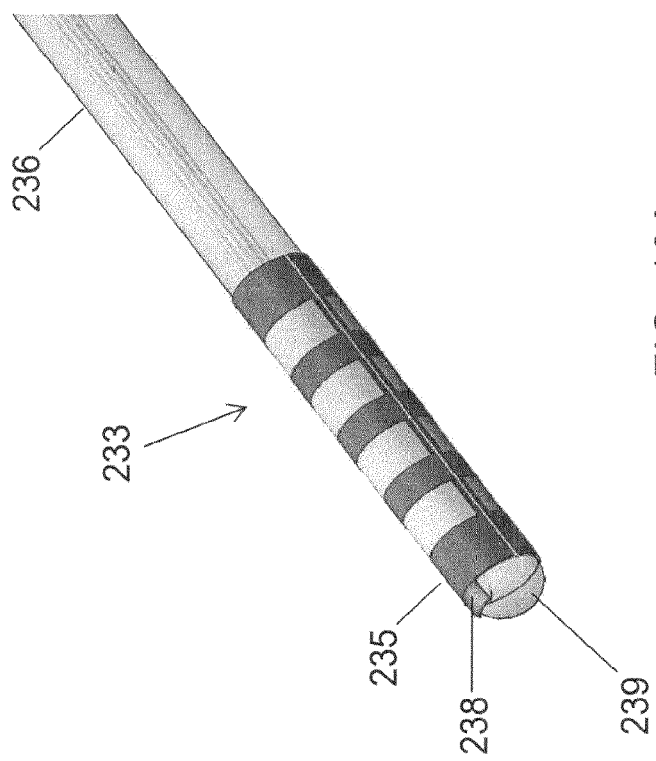

Referring to FIG. 16A, the distal portion of a neurological probe 233, similar to that illustrated in FIG. 4, is shown. The cutaway image is shown in FIG. 16B with part of the microelectrode film 235 removed. In this embodiment a cylindrical member 236 contains one or more conductive lead wires 237 along an inner lumen, or alternatively, the lead wires have been molded in place when the cylindrical member 236 was formed. In this embodiment the extension 238 connecting the cylindrically formed outer surface of the microelectrode film 235 is wrapped along the most distal portion of the cylindrical member 236. It remains within the inner cylindrical volume formed by the microelectrode film 235. The distal portion is covered and sealed using end cap 239 which may be implemented in a semi-rigid material such as silicone, or a rigid polymeric or metallic material such as stainless steel. If it is conductive it can also be electrically attached (not shown) to the lead wires 237. Alternatively, end cap 239 can be molded in place, as a glob-top of a polymerizable material such as epoxy or silicone. The lead wires 237 are attached to contact pads 281 thereby electrically connecting the proximal portion of the neurological probe to the distal portion.

Figure 16D:
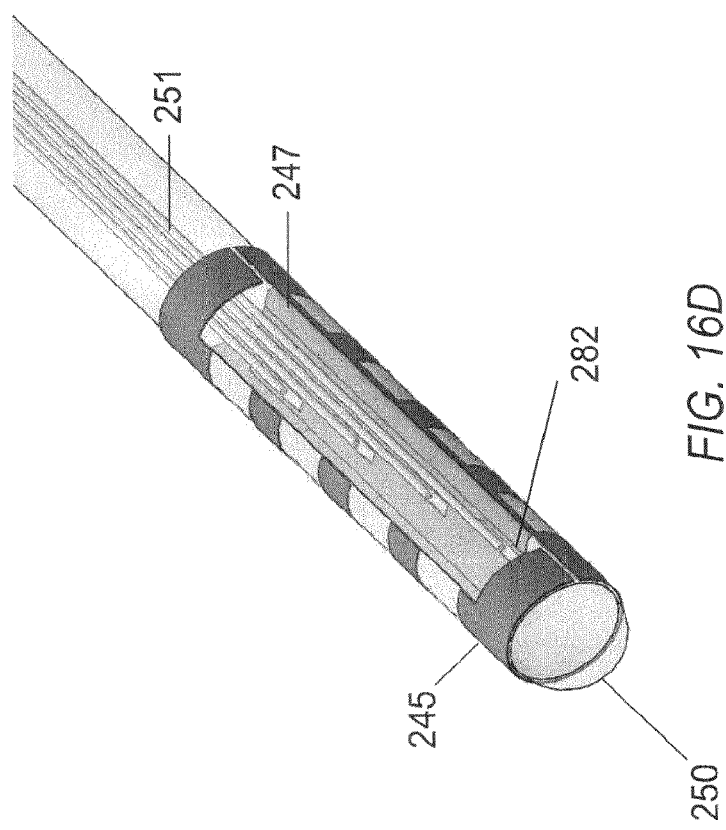
Figure 16C:
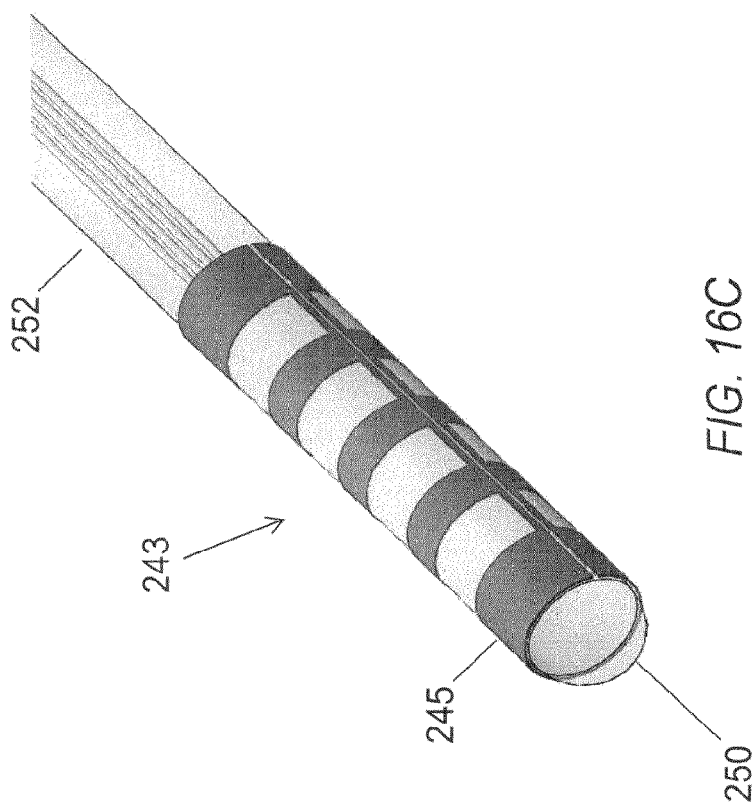

Referring now to FIG. 16C, the distal portion of a neurological probe 243 which is very similar to FIG. 4 is shown. The cutaway image is shown in FIG. 16D with part of the microelectrode film 245 removed. In this embodiment a cylindrical member 252 contains one or more conductive lead wires 251 along an inner lumen, or alternatively, the lead wires have been molded in place when the cylindrical member 252 was formed. In this embodiment the extension 247 connecting the cylindrically formed outer surface of the microelectrode film 245 is wrapped radially into the most distal portion of the cylindrical member 251. It remains within the inner cylindrical volume formed by the microelectrode film 245. The distal portion is covered and sealed using end cap 250 which may be implemented in a semi-rigid material such as silicone, or a rigid polymeric or metallic material such as stainless steel. If it is conductive it can also be electrically attached (not shown) to the lead wires 251. Alternatively, end cap 250 can be molded in place, as a glob-top of a polymerizable material such as epoxy or silicone. The lead wires 251 are attached to contact pads 282 thereby electrically connecting the proximal portion of the neurological probe to the distal portion.

Referring now to FIG. 17A, the distal portion of a neurological probe 263 which is very similar to FIG. 4 is shown. The cutaway image is shown in FIG. 17B with part of the entire outer portion of the microelectrode film 265 removed. In this embodiment two tubular members constitute the axis of the neurological probe. A first, outer tubular member 266 is implemented in a polymeric material such as polyurethane or silicone. A second tubular member 267, has an outer diameter less than the inner diameter of outer tubular member 266, and is implemented in a polymeric material such as polyurethane, silicone, or polyimide. Along the space between the two tubular members run one or more conductive lead wires 273. Alternatively, the lead wires can be molded in place when the outer or inner tubular member is formed. In this embodiment the extension 275 connecting the cylindrically formed outer surface of the microelectrode film 265 is wrapped at the most distal portion between the two tubular members. The lead wires 273 are attached to contact pads 283 thereby electrically connecting the proximal portion of the neurological probe to the distal portion.

FIG. 18A illustrates in more detail a proximal portion of the elongated probe assembly 420, showing extension of the open ended lumen 424 to the proximal end, terminating in the open end 430. A cross sectional view of the four cylindrical contacts 426 is illustrated in FIG. 18B. As shown, each of the elongated helically wound internal electrical conductors 428 is connected to a respective one of the four cylindrical contacts 426. Electrical contact can be maintained through bonding, soldering, conductive adhesives, mechanical fasteners, or any combination or suitable contact means to maintain electrical conductivity between the cylindrical contact 426 and the respective internal electrical conductor 428.

Figure 18C:
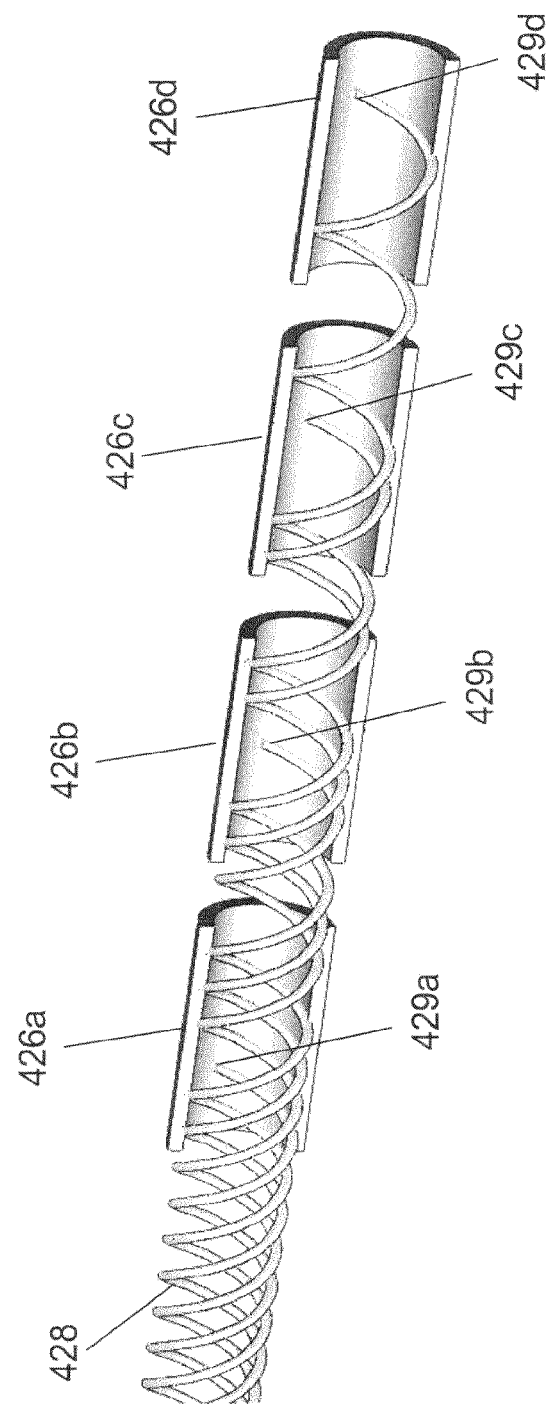
FIG. 18C is a more detailed cross-sectional view of an alternative assembly of the proximal portion of an elongated microelectrode assembly.

FIG. 18C illustrates in more detail a proximal portion of the elongated probe assembly 420, in an embodiment where lead wires have been wrapped axially around an inner tubular structure such as in FIG. 16E. A cross sectional view of the four cylindrical contacts 426 is illustrated. As shown, each of the elongated helically would internal electrical conductors 429 is connected to a respective one of the four cylindrical contacts 426. Electrical contact can be maintained through bonding, soldering, conductive adhesives, mechanical fasteners, or any combination or suitable contact means to maintain electrical conductivity between the cylindrical contact 426 and the respective internal electrical conductor 429.

Figure 19:
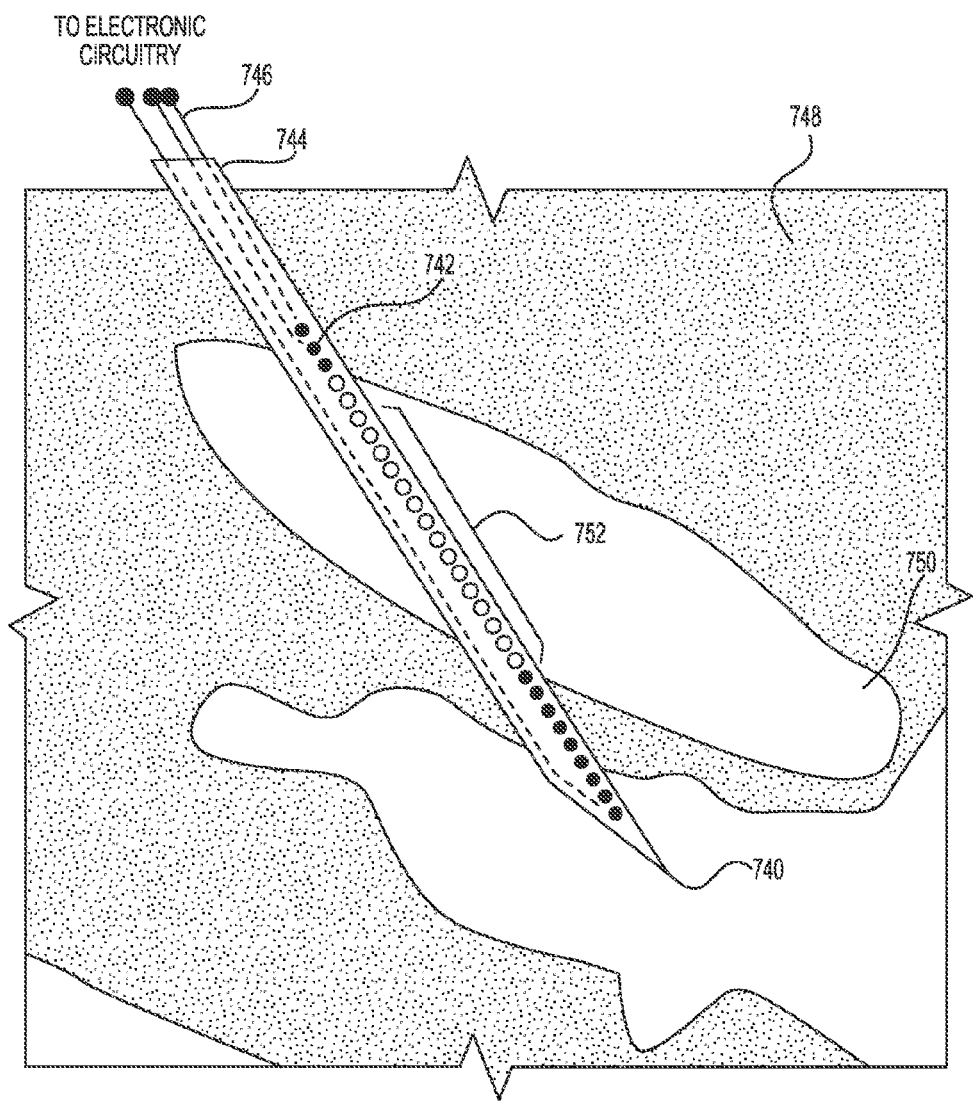
FIG. 19 is a schematic view of a cross-sectional of a portion of a human anatomy illustrating an exemplary microelectrode structure positioned at a neurological target.

Referring now to FIG. 19 a cross-sectional view of a portion of an anatomy 748 is shown, illustrating an exemplary microelectrode probe assembly 740 positioned at a neurological target 750. In general, the probe assembly 740 is representative of an any of the probe assemblies described herein. The microelectrode probe assembly 740 includes an array of microelectrode elements 742 distributed along an elongated supporting structure 744. Preferably, the microelectrode probe assembly 740 is shaped and sized to allow one or more of the microelectrode elements 742 to be positioned at the neurological target 750. To this end, materials used in construction of microelectrode probe assembly, as well as one or more of its construction features, size, shape, and orientation can be selected for biocompatibility. As illustrated, one or more of the microelectrode elements 742 of the microelectrode probe assembly 740 are positioned in intimate contact with the neurological target 750. One or more additional microelectrode elements 742 of the probe assembly 740 may reside at locations not in the immediate vicinity of the neurological target 750. In at least some embodiments, one or more of the microelectrode elements 742 are remotely accessible from a proximal end of the probe assembly 740 via one or more electrically conductive leads 746.

The supporting structure 744 can be a ridged, or semi ridged structure, such as a an elongated, flat shaft. Alternatively or in addition, the structure can be a flexible structure, such as one or more flexible substantially non conducting substrate (i.e., a bi-electric ribbon) onto which the microelectrode elements 742 are formed as electrically conductive film layers. The one or more microelectrode elements 742 are in communication with electronic circuitry (not shown) through one or more electrical leads 746 that can be routed through an internal lumen of a supporting structure 744 and/or formed using elongated film layers along a flexible, ribbon like supporting structure 744.

In some embodiments, the microelectrode elements 742 can be placed into the brain generally for recording and/or stimulation of the cortex and for deep brain stimulation and/or recording of neurological targets including the subthalamic nucleus and the globus pallidus. The microelectrode elements 742 can also be placed in other parts of the body, such as the retina, the peripheral nervous system for neural recording and/or neural stimulation of such portions of an animal anatomy. Although microelectrodes are discussed generally throughout the various embodiments, there is no intention to limit the upper or lower size of the microelectrodes. The devices and methods described herein are generally scalable, with a microelectrode size determined according to the attended application. For at least some of the neurological applications, microelectrodes are dimensioned sub-millimeter. In some embodiments, microelectrodes are dimensioned sub-micron. In some embodiments, the microelectrodes are formed as planar structures having a diameter of about 50 µm that are arranged in a linear array with center to center spacing of about 100 µm. The planar structure of the microelectrodes can have regular shapes, such as circles, ellipses, polygons, irregular shapes, or a combination of such regular and/or irregular shapes.

This probe assembly 740 is implantable near a neurological target, such as a target brain structure, using common neurosurgical techniques such as stereotaxis or endoscopy. The device might be inserted without support or within a cannula which may have an inner dimension slightly larger than the outer dimension of the device. When used, such a cannula would be retracted once the device is in position.

The operator can connect the probe assembly 740 to a recorder unit configured to identify certain regions of the neurological target (e.g., the brain) according to the electrical activity. In some embodiments, the microelectrode elements 742 used to record from the neurological target 750 can be the same microelectrodes as those used to stimulate the target in application in which both recording and stimulation are accomplished. Alternatively or in addition, the microelectrodes 742 used to record from the neurological target 750 can be separate microelectrodes 742 from those used to stimulate the target 750. In some embodiments, microelectrodes destined for recording may differ in one or more of size, shape, number, an arrange from those microelectrodes destined for stimulation, using different microelectrodes.

The microelectrode elements 742 can be connected to a stimulation source through one or more interconnecting leads. In some embodiment, at least a portion of the stimulation source can be extracorporeal. Alternatively or in addition, the stimulation source can be in vivo. Any implanted elements of the stimulation source are preferably fabricated and/or contained with a hermetically sealed, bio-compatible envelope. Such bio-compatible packaging of signal sources is well known, for example, in the area of artificial pacemakers. The stimulation source, when provided, may be a controllable signal generator producing a desired signal according to a prescribed input. For example, the signal generator may receive an input indicative of a desired output stimulation signal frequency. Such output stimulation signals can have a variety of wave forms, such a pulses, charged balanced pulses, sinusoidal, square wave, triangle wave, and combinations of such basic wave forms.

In some embodiments, the stimulation source includes a pulse generator for applying signals to the microelectrodes site. The signals from the pulse generator can be connected directly to the microelectrodes, or they can be preprocessed using electronics. In some embodiments, such preprocessing electronics are embedded within the implantable device. The preprocessing electronics can filter certain parts of an original signal, such as a cardiac pacemaker signal, in order to select preferred frequency components of the original signal that are at or near a peak resistance frequency of the microelectrodes. For embodiments in which there are more microelectrodes than signals, electronics can route the stimulation signals to preferred one or more of the microelectrodes.

Figure 20:
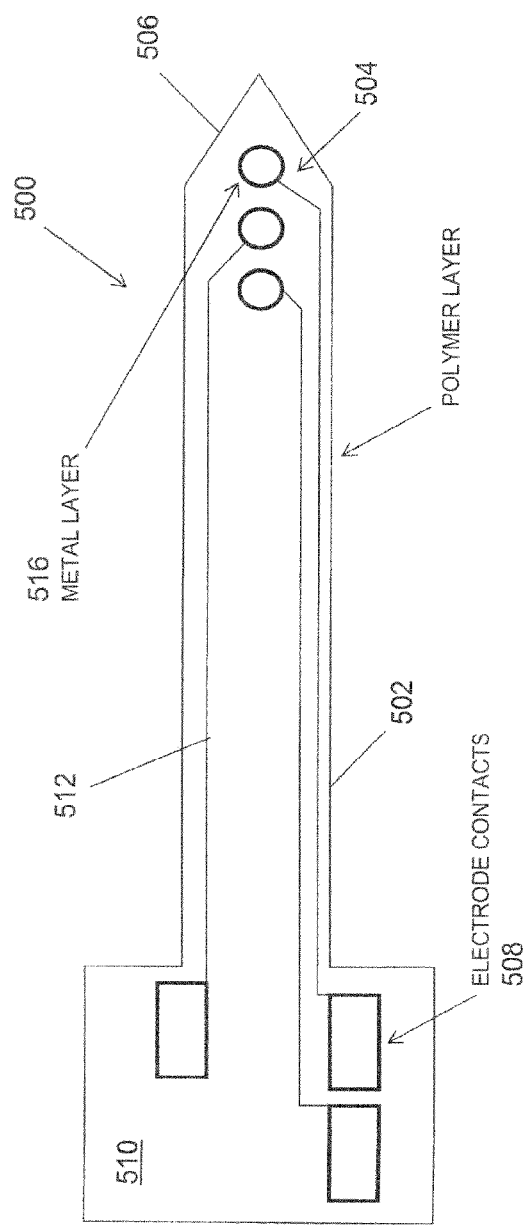
FIG. 20 is a schematic diagram of one embodiment of an electrode tip assembly.

FIG. 20 is a schematic diagram of one embodiment of a microelectrode tip assembly. The microelectrode tip assembly 500 includes a supporting member 502 including an elongated portion terminating in a distal tip 506 and a somewhat more expansive proximal extension 510. A linear array of three microelectrode elements 504 is arranged along a longitudinal axis of the elongated portion of the support member 502. A corresponding number of three electrode contacts 508 are located on the proximal extension 510. Each microelectrode element of the array 504 is interconnected to a respective one of the electrode contacts 508 through a respective electrically conducting lead trace 512. In the exemplary embodiment, a polymer layer 514 is applied to at least one surface of the underlying support member 502. Each of the microelectrode leads, electrode contacts 508, and interconnecting lead traces 512 is implemented as an electrically conducting layer on or within the polymer layer 514. Although a linear array of microelectrode elements is shown, other embodiments are possible with nonlinear, planar, curved surface, and volumetric (i.e., three-dimensional) distributions of such microelectrodes are possible.

Figure 21:
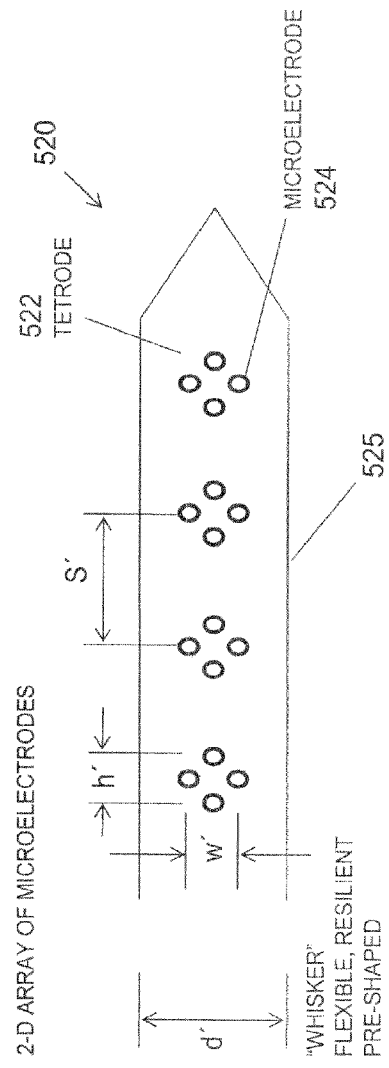
FIG. 21 is a schematic diagram of a distal portion of another embodiment of an microelectrode tip assembly.

FIG. 21 is a schematic diagram of a distal portion of another embodiment of an microelectrode tip assembly 520, including a linear arrangement of microelectrode element arrays 522. Each microelectrode element array 522 includes multiple sub-microelectrode elements 524. In the illustrative embodiments, each of the microelectrode element arrays 522 includes four sub-microelectrode elements 524 arranged in a diamond pattern and referred to herein as a tetrode. In some embodiment, each of the sub-microelectrode elements 524 is in communication with a respective electrode contact (not shown) through a respective lead trace (not shown). Alternatively or in addition, one or more of the sub-microelectrode elements 524 may share a common lead trace.

The width w' of the tetrode array 522 is less than a diameter of the elongated support member 525. A height h' of the tetrode array 522 may be the same as the width w' or different, thereby controlling an aspect ratio of the tetrode array 522. The center-to-center spacing of adjacent tetrode array elements 522, S' can be the same, or different measured along the length of the array. As shown, each of the sub-microelectrode elements 524 is identical and circular. In some embodiments, the tetrode elements 524 are shaped, such as polygons, ellipses, annular rings, and the like. Alternatively or in addition, one or more of the sub-microelectrode elements 524 of the tetrode array 522 may differ from other elements of the same array 522. Additionally, tetrode array elements 522 may differ in geometry, size, and configuration along the length of the elongated support member. Once again, two and three dimensional arrangements of such array elements are possible.

Beneficially, the exemplary configuration of sub-microelectrode elements may be energized in a variety of different configurations. For example, all four sub-elements 524 may be connected to the same recording or stimulation lead. Alternatively, one or more of the sub-elements 524 may be coupled to the same recording or stimulation lead (e.g., anode), while one or more of the other sub-elements of the same array 522 may be coupled to a different recording or stimulation lead (e.g., cathode). In some embodiments, one or more of the sub-microelectrode elements is connected to an electrical ground.

In some embodiments, each of the sub elements 524 of the exemplary tetrode array 522 is coupled to a respective lead. In recording mode, each sub element 524 is coupled to a respective recording lead. Thus, for each tetrode array 522, the recorder will record four separate channels Accordingly, electrophysiological activity from the same neurological target may be recorded independently through each of the independent sub elements 524 of the tetrode array 522. Dependent at least in part upon the relative location of the neurological target, the same electrophysiological activity may be recorded with different time delays, and perhaps different amplitudes. Using available signal processing techniques, the different signals recorded from two or more of the tetrode sub elements 524 can be further processed to determine relative location of the neurological target with respect to the tetrode array 522. Some exemplary techniques available for solving direction to the target include triangulation and time-difference-of-arrival, in which relative delay of the received signals, combined with knowledge of the arrangement and spacing of the sub-elements 524 can be used to solve for distances and/or angles to the target. In use, the tetrode of such a tetrode-stimulator hybrid microelectrode would be used to record neural activity from a volume of tissue immediately in front of the microelectrode. The stimulation electrode would be used to stimulate neural activity and transfer charge to that same volume of tissue.

Figure 22A:
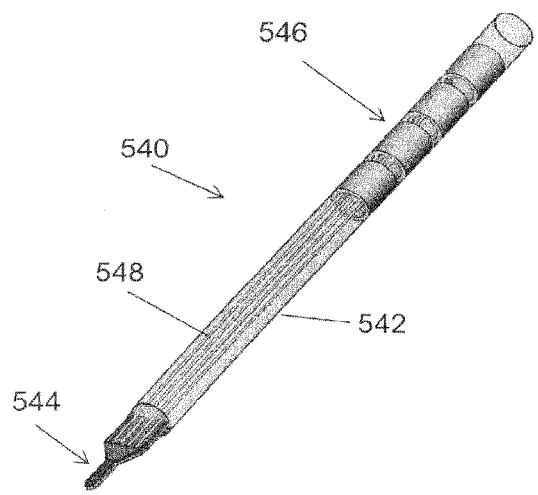
FIG. 22A is a perspective view of one embodiment of an elongated microelectrode assembly having a microelectrode tip assembly at a distal end.
Figure 22B:
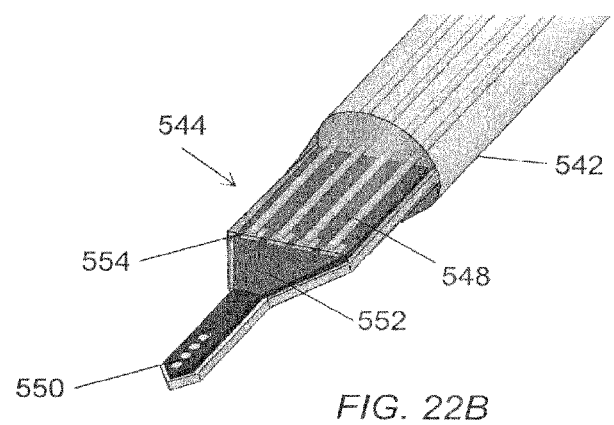
FIG. 22B is a more detailed view of a distal end of the elongated microelectrode assembly of FIG. 22A.

FIG. 22A is a perspective view of one embodiment of an elongated microelectrode assembly 540 having a microelectrode tip assembly 544 disposed at a distal end. The exemplary configuration is similar to the neurological probe device 100 illustrated in FIG. 1, except that the microelectrode array 544 is provided on a distal extension protruding away from a distal tip of the assembly 540, rather than being wrapped around the distal end as shown in FIG. 1. Additionally, there are no microelectronic devices included in this assembly 540. Thus, neurological signals, be they detected signals or stimulation signals, are directed along internal wire leads 548 between each of the proximal contacts 546 and a respective one of the distal microelectrode elements 550, shown in more detail in FIG. 22B. The length of the elongated supporting cylinder 542 can vary. Also shown in FIG. 22B is a proximal extension 522 including four wire lead contacts 544, each coupled to a distal end of a respective one of the internal wire leads 548. In some embodiments, the microelectrode array 544 incorporates a rigid or semi-rigid backing.

Figure 22C:
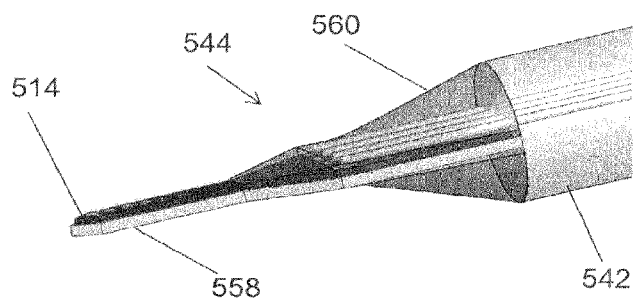
FIG. 22C is another more detailed view of the distal end of the elongated microelectrode assembly of FIG. 22A.

FIG. 22C is another more detailed view of the distal end of the elongated microelectrode assembly 540 (FIG. 22A). In some embodiments, the rigid tip 544 can be held in place with a biocompatible adhesive 560. Alternatively or in addition, at least a distal portion of the elongated supporting cylinder is formed around (e.g., injection molded) a proximal portion of the rigid tip 544. Also apparent in the exemplary embodiment is the relative arrangement of a support substrate 558 and a polymer layer 514.

Figure 23:
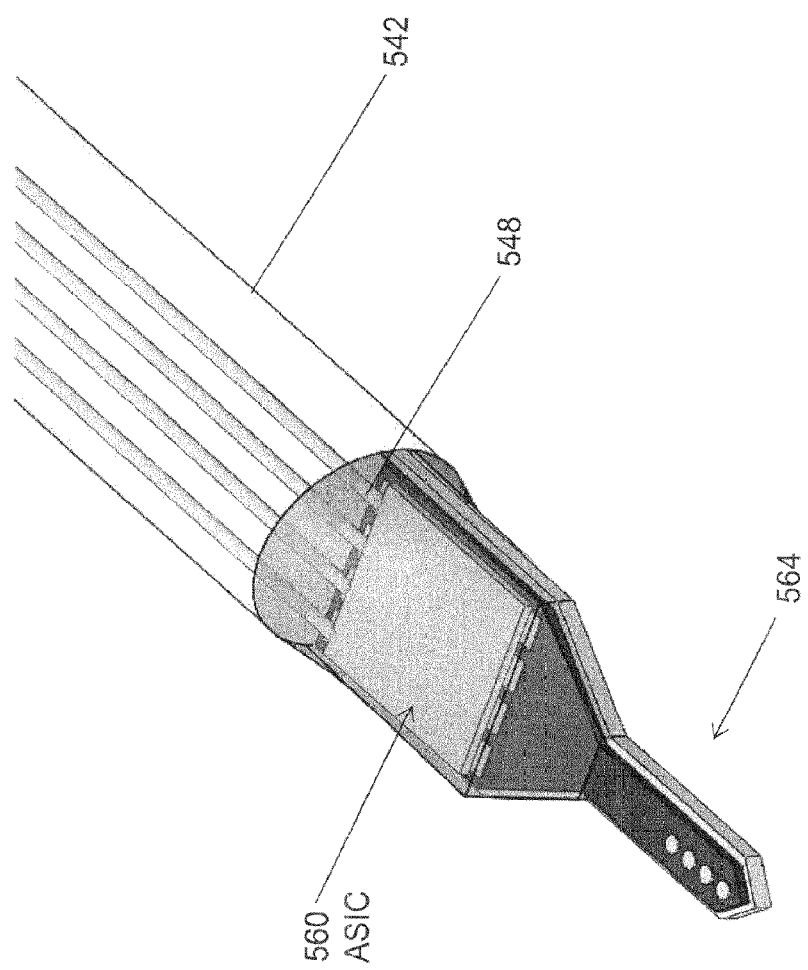
FIG. 23 is a perspective view of a distal end of another embodiment of an elongated microelectrode assembly having an electrode tip assembly at a distal end.

FIG. 23 is a perspective view of a distal end of another embodiment of an elongated microelectrode assembly having an electrode tip assembly 564 disposed at its distal end. In particular, the electrode tip assembly 564 includes a microelectronic device 560 mounted thereon. The microelectronic device 560 can include an application specific integrated circuit (ASIC), standard integrated circuits, and other circuit elements, including resistors, capacitors, inductors, diodes, and transistors. Note that the wires 548 from the contact rings come into contact with the electronics. The electronics process the signals and direct them between one or more remote medical devices and one or more of the microelectrode sites.

Figure 24:
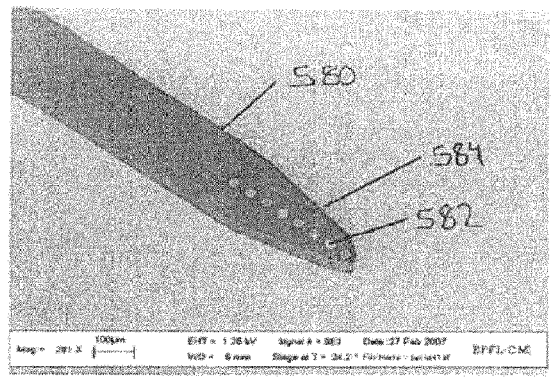
FIG. 24 is a micrograph of a distal portion of an embodiment of a microelectrode tip.
Figure 25:
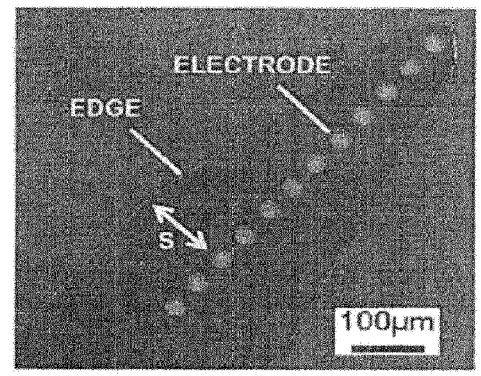
FIG. 25 is a micrograph of the distal portion of the microelectrode tip illustrated in FIG. 24.
Figure 26:
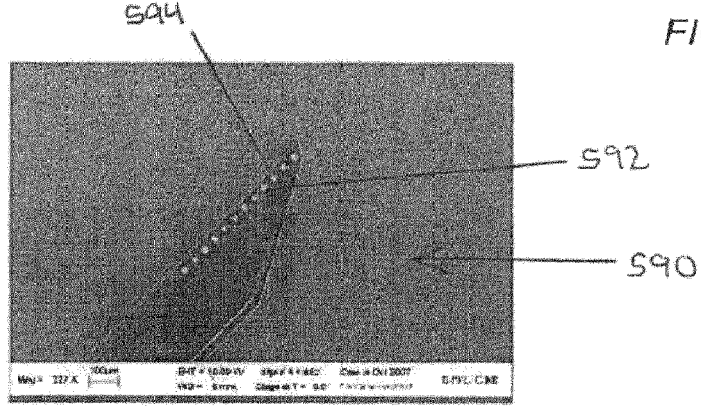
FIG. 26 is a micrograph of a distal portion of another embodiment of a microelectrode tip.

FIG. 24 is a micrograph of a distal portion of an embodiment of a microelectrode tip 580 including a linear array of eight microelectrode elements 582. The linear array of microelectrode elements 582 is arranged along a central elongated axis. Distal edges 584 of the device are spaced apart from either side the proximal most microelectrode array element and taper towards a distal tip as shown. Placement of the elements apart from the device edge can be beneficial in avoiding unwanted tissue reaction occurring along the edge, the more distal microelectrode elements are relatively closer to their adjacent edges 584. FIG. 25 is a more detailed micrograph of the distal portion of the microelectrode tip illustrated in FIG. 24. FIG. 26 is a micrograph of a distal portion of another embodiment of a microelectrode tip 590 in which a linear array of microelectrode elements 594 is arranged along a parallel edge 594 of the device 590.

Figure 27:
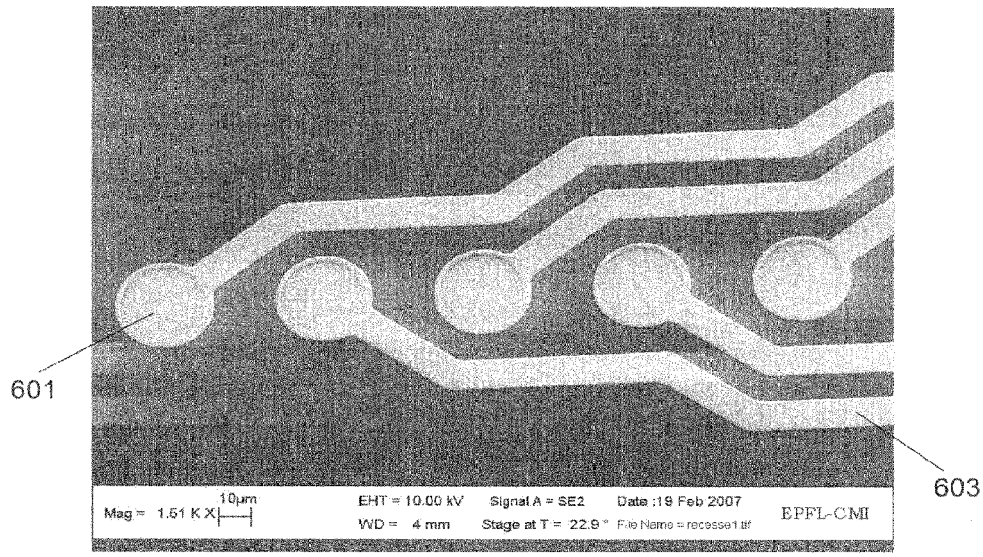
FIG. 27 is a micrograph of conductive elements of an embodiment of a microelectrode array.

FIG. 27 is a micrograph of a top view of an exemplary arrangement of conductive elements 601 along an embodiment of a microelectrode array. The device includes a typical microelectrode 601 and trace 603 architecture, in which a respective trace interconnecting lead 603 is routed to each of the microelectrode elements.

Figures 28A, 28B:
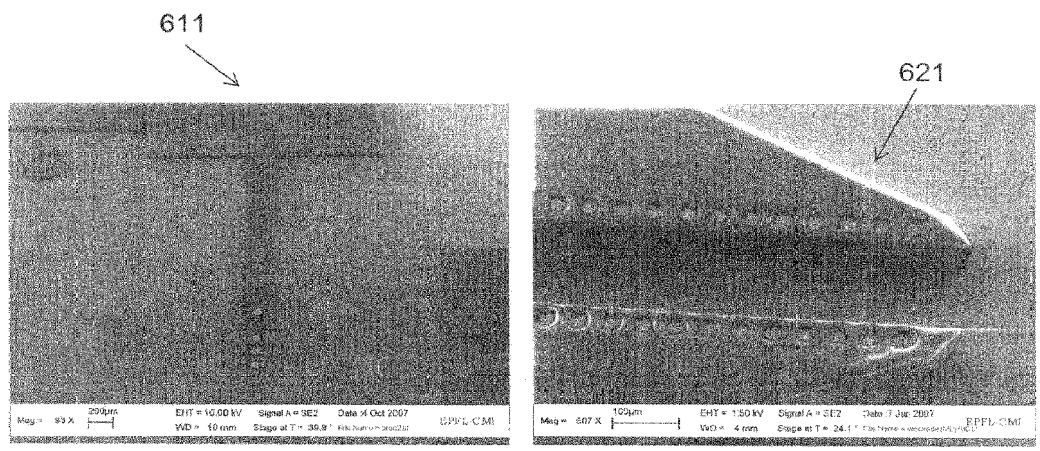
FIG. 28A is a micrograph of a distal portion of another embodiment of a microelectrode tip.
FIG. 28B is a micrograph of opposing sides of a distal portion of an embodiment of a microelectrode tip.

FIG. 28A and FIG. 28B are micrograph images of a distal portion of other embodiments of a microelectrode tip 611, 621.

Fabrication Methods

There are several techniques to achieve the microfabricated component and the required mechanical and electrical characteristics. The fabrication procedure is a series of procedural steps in which various layers are deposited or removed (e.g., etched) to achieve a final form. Exemplary sequence of procedural steps is described herein.

Step 1: The Carrier Wafer and Sacrificial Layer

In a first step illustrated in FIG. 29A, a carrier substrate 650 is provided, such as a wafer composed of a crystalline material, such as Silicon, or an amorphous material, such as glass, in particular a thermal shock resistant borosilicate glass commercially available under the brand name PYREX®, or other suitable smooth supportive material. A first layer 652 comprising at least two sub-layers is applied to a surface of the wafer 650. One of the sub-layers 652 is a sacrificial layer deposited on the wafer 650, which will be removed in a subsequent electrochemical etch step. Preferably, the sacrificial sub-layer is preceded by another sub-layer, referred to as an underlayer, that will serve to form the electrochemical cell required to etch the sacrificial layer. In the preferred embodiment, the sacrificial sub-layer is Aluminum, or an alloy of Aluminum such as AlSi, which has a smaller granularity, whereas the underlayer is a TiW alloy, Chrome, or similar metal. The sacrificial layer is represented as a black line 652 in the image below, the carrier wafer 650 is shown in gray. Each of the images illustrated in this series represents a cross section of an exemplary embodiment, and are used herein to describe the procedural steps.

Figure 30:
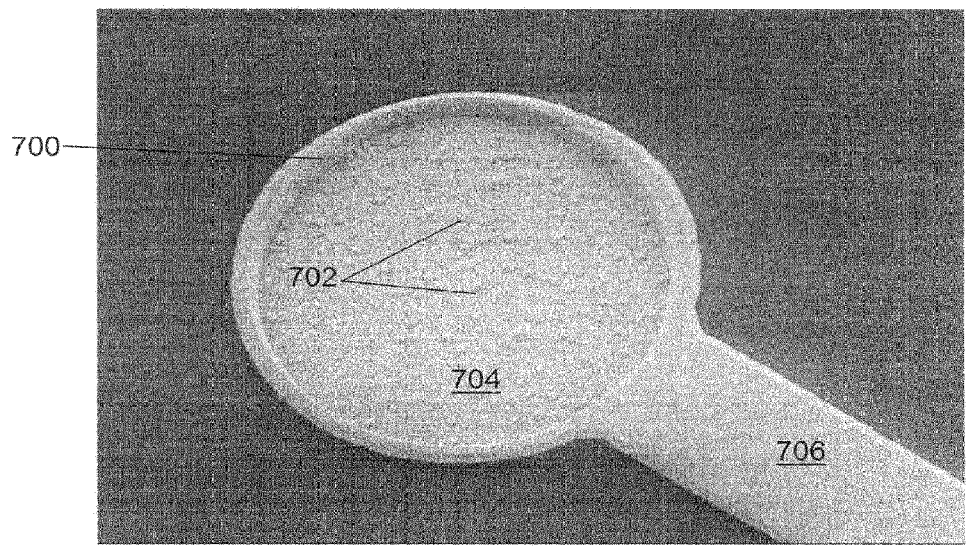
FIG. 30 is a micrograph of an embodiment of a microelectrode.

In some embodiments, the sacrificial layer 652, in addition to facilitating electrochemical removal of the finished device, is to establish a granularity, or grain size to the surface of the finished device. Namely, the sacrificial layer can add a micro or nano-roughness to the surface that can be precisely controlled at least in part by the selection of a suitable underlayer. For example, Aluminum can be deposited by DC Sputtering with a grain size ranging from 5 nm or less to 600 nm or more. This grain size provides a first grainy surface. A polymeric layer is subsequently deposited over the grainy sacrificial layer. This polymeric layer can be locally etched in order to create vias that open onto the grainy sacrificial layer. Subsequently, a metal layer is deposited over the resulting grainy surface, and polymeric layer, in which the deposited metal serves as the neuro-recording/stimulation microelectrode element, and wire trace. The area of the metal that falls into the via in the polymeric layer forms the microelectrode surface. The area of the metal falls on the polymeric layer can be etched into linear traces and form the interconnect between microelectrodes and bond pads or circuitry. The process is described below as a "backside microelectrode." Due to such an increase in granularity over a relatively flat surface, the overall surface area of the metal layer will have a higher effective surface area than that area subtended by the perimeter of the element. Beneficially, the increased surface area results in a corresponding decrease in electrical impedance of the electrode element. This concept is important in that it facilitates recording, allowing a greater recording fidelity with less complexity due to the reduction in impedance, while maintaining the same small diameter that guarantees high localization of the neural activity. An electrically conducting surface of an exemplary microelectrode element thus formed is illustrated in the image of FIG. 30.

Step 2: Deposition of First Polymeric Layer

Referring to FIG. 29B, the next step in the fabrication process includes depositing a first polymeric layer 654— sometimes referred to as a resin layer 654. The first polymeric layer 654 can be deposited upon the sacrificial layer 652. This can be done by any suitable means known to those skilled in the art of MEMS processing, by: (i) spin coating a liquid polymer precursor such as Polyimide or Silicone precursor; (ii) depositing a polymer through chemical vapor deposition as is done with parylene-C; or (iii) laminating a polymer sheet 654 onto the wafer 650. In some embodiments, the polymer layer 654 is heated, or baked, to polymerize.

Referring next to FIG. 29C and FIG. 29D, an optional step includes etching of first polymeric layer 654, as may be beneficial when preparing a device having one or more backside electrodes, that will ultimately be located along an underside of the finished device. In this optional step, the first polymeric layer 654 is locally etched in order to form open areas 652, where metals for such backside microelectrodes may be later deposited. This step is optional, and unnecessary when there is no need for any such backside electrodes on the finished device—all microelectrode contacts being formed on a front surface of the finished device. This step is also advantageous, because the backside electrode metal layer, when included, will also benefit from the higher effective surface area that can be gained from the sacrificial layer's granularity.

The etching can be performed by depositing a mask 656 on the first polymeric layer 654. Using well established methods for thin film processing, the mask 656 can be photolithographically defined. For example, a photosensitive resin 656 is spin coated onto the polymeric layer 654. A process of exposing an unmasked portion of the resin layer 657 to UV light is used for those areas in which the operator chooses to remove the polymer layer 654. The device is developed in a solvent that will selectively remove only the unmasked areas 657 that were exposed to UV light. This selective etching process locally opens areas of the polymeric layer 654, by etching, exposing in this instance the underlayer 652. In some embodiments the device is etched in oxygen plasma to remove the exposed portion of the polymer layer 657. The etch mask 656 may also be removed by the same etching process, but if it is thicker than the polymer layer it may not be completely removed. Illustrated in the figures is a defined etch mask 656. Alternatively or in addition, the etch mask 656 can also be implemented in a non-photodefinable layer, such as Silicon Dioxide deposited by DC Sputtering. The Silicon Dioxide then has the photoresist deposited and photolithographically defined on top of it. After etching the polymeric layer 654, the Silicon Dioxide mask can be optionally removed.

FIG. 29D illustrates the device after the exposed portion of the polymer layer 657 was removed. As illustrated, a portion of the sacrificial layer 652 is now exposed. In some embodiments, the photoresist mask 656 cab be subsequently removed using a suitable solvent.

Step 3: Deposition and Definition of Metal Layer

The deposition of the layer can also be made through a resist mask 670, as shown in FIG. 29G. In this case a photoresist mask 686' would be photolithographically defined on the polymer layer 654. An electrically conductive (e.g., metal) layer 692' can then be deposited over the masked device. Thus, unmasked areas 687 at which it is desirable to have an electrically conducting layer 690 formed, are open with respect to the photoresist mask 686', such that the a portion of the deposited electrically conductive layer 692' lands directly onto the polymeric layer 654 at the unmasked area 687. This technique is sometimes referred to as a "lift off" technique. The photoresist mask 686', with any electrically conductive layer 692' thereon, is then dissolved, such that the only remaining metal 690 is on the polymer at the formerly unmasked areas. Note that the metal layer 692' on top of the photoresist 686' is also removed by removal of the photoresist mask 686'. Beneficially, that portion of the electrically conducting layer 690 in contact with the polymeric layer 654 remains after removal of the mask 686'.

In an alternative method, referring now to FIG. 29H, a metal layer 692" can be deposited onto the entire surface of a wafer 650. As illustrated, the metal layer 692" is provided on top of the polymeric layer 654, which is provided on top of the sacrificial layer 652. A masking layer 686" is provided over that portion of the metal layer 692" to remain. Exposed regions of the metal layer 692" can then be removed locally by a photolithographic step such as demonstrated below.

Referring next to FIG. 29E, an electrically conductive layer that serves as the electrode 680 and one or more electrically conductive traces 682 is next deposited. Such an electrically conductive layer can include a metal layer deposited by any suitable thin-film process, such as DC sputtering, RF Sputtering, or evaporation techniques. The metal deposited in the electrically conductive layer 680, 682 is preferably platinum, iridium, platinum-iridium alloy, iridium-oxide, titanium, or a titanium alloy to ensure acceptable electrical characteristics (such as charge transfer) and mechanical strength.

In a preferred embodiment the metal layer 680, 682 is deposited with an adhesion promotion layer in contact with the polymer. For example, titanium can be sputtered onto the polyimide layer 654 in an initial partial step to improve adhesion, followed by a platinum layer deposited in an intermediate partial step, and optionally, a titanium layer may them be deposited onto the platinum layer in a subsequent partial step. This creates a Ti—Pt—Ti sandwich, where the titanium is responsible for adhering the platinum to the polyimide on either side of it, and the platinum is the metal layer that will be used.

For embodiments that produce backside electrodes, as described above in reference to FIG. 29C through FIG. 29E, then the electrically conductive layer 680 will be in contact with the sacrificial layer 652 in the region of the backside electrode 680. The metal deposition technique is selected to ensure that there is contact between the metal on top of the polymeric layer 654, and the metal on the exposed portion of the sacrificial layer 652. This is done by ensuring the metal 680 is conformally deposited, and that the polymeric layer 654 is not too thick. The metal layer 680 can then be photolithographically defined as explained above. An etch in a plasma, such as Chlorine gas plasma, can be used to remove the metal layers deposited using a photoresist mask. The photoresist mask can then be removed in a solvent.

Step 4: Deposition of 2nd Polymeric Layer

Referring next to FIG. 29I for a backside electrode embodiment and FIG. 29H, a second polymeric layer 672, 692 is deposited using a suitable technique, such as any of the techniques described above with respect to FIG. 29B. The second polymeric layer 672, 692 is deposited onto the underlying polymeric layer 654, 664, and any exposed metal layer 658, 668. In some embodiments, the first polymeric layer 654, 664 can be processed in order to increase its adhesion to the second polymeric layer 672, 692. For example, such processing can be accomplished through surface roughening or chemical alteration using an oxygen plasma. The second insulative, or polymeric layer 672, 692 isolates the electrical traces, when formed on different layers with respect to each other. In some embodiments, the polymeric material can be subjected to thermal process, such as baking.

Step 5: Definition of Polymeric Layers

Referring next to FIG. 29I through FIG. 29K, to define the one or more polymer layers 654, 691 and therefore the device itself, an etch mask 695 is deposited to an external surface of the device. This etch mask 695 may consist of a photodefinable resist but preferably it will be a hard etch mask such as silicon dioxide or amorphous silicon which can withstand the etch of the polymeric layer without significant degradation.

The wafer 650 at this point also has a hard mask 693 deposited, for example, by DC or RF sputtering. A photodefinable 695 resist is deposited on the hard mask 693 and the areas of the polymer 654, 691 that are to be etched are defined.

The hard mask 693 is then etched with a different gas then would be used to etch the polymeric layer 654, 691, for example CF4 plasma. Now the one or more polymeric layer 654, 691 can be etched with a gas, such as oxygen plasma, to the sacrificial layer 652, as shown. Thus, the remaining portions of the hard mask shown in FIG. 29K define the extent of the device, by defining the device's edges 659.

Figure 32A:
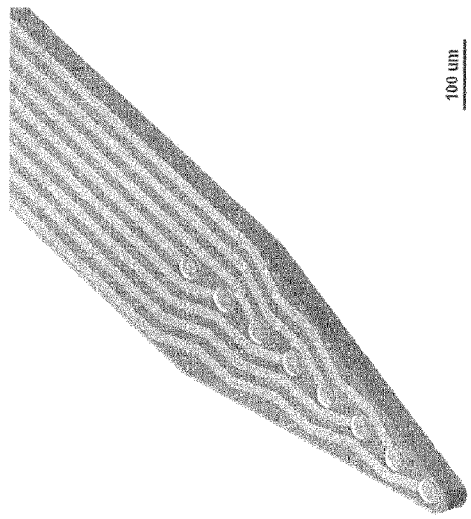
FIG. 32A is a perspective view of a distal portion of a microelectrode tip.
Figure 32B:
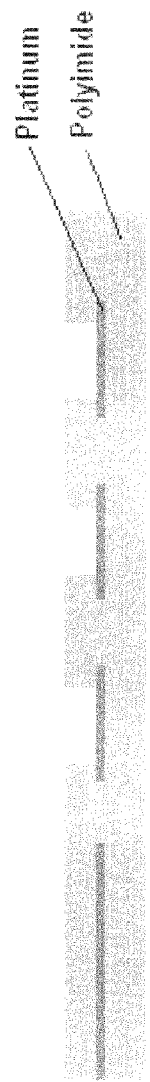
FIG. 32B is a cross sectional view of the distal portion of the microelectrode tip illustrated in FIG. 32A.

The remaining portions of the hard mask 693 can be optionally removed in a subsequent step. The goal of this etching process is to: (i) define the microelectrode sites; (ii) define the device shape; and (iii) define the contact areas for electronics or wire attachment. A top view of an exemplary finished microelectrode device is shown in FIG. 31D. A cross-section of another exemplary finished microelectrode device is shown in FIG. 32A.

If the option of making backside electrodes is taken in step 2, the device will have microelectrodes at its surface once removed from the substrate. Such a device is shown in FIG. 24 and FIG. 25. Exemplary front side electrodes are shown in the device of FIG. 28B.

Step 6: Optional Bonding of Electronics

If the device is to be integrated with electronics, referring now to FIG. 29L, the contact pads 699 can be used at this point to connect to an electrical circuit device 697. For example, an Integrated Circuit chip 697 can be connected to the contacts 690 (FIG. 29K) by flip-chip bonding the chip 697 to the device 661, using a conductive epoxy interlayer. The chip 697 can then be further attached by chemical bonding, such as an epoxy to ensure a strong and reliable connection to the device 661.

Step 7: Removal of Devices from Carrier Wafer

A final step of the fabrication process is illustrated in FIG. 29M, to remove the device 661, such as a MEMS device, from the underlying wafer 650. The sacrificial layer 652 (e.g., FIG. 29L) is electrochemically etched away. Removal of the sacrificial layer 652 from under the device 661, frees the underside of the device 661 from the wafer 650. This can be accomplished by placing the wafer in a saline bath with a high NaCl concentration. A platinum electrode in the bath can be used as a reference. A voltage is applied to the aluminum layer with respect to the platinum electrode. The electrochemical cell created by the Aluminum and TiW etches the aluminum, and this etch continues below the devices. The devices fall into the bath and are removed.

FIG. 30 is a micrograph of an embodiment of a backside microelectrode element 700. The image is taken at the process step shown in FIG. 29E. The granularity 702 of the aluminum sacrificial layer surface 704 is used to increase the effective surface area of a metal electrode in a subsequent step. Also shown is a portion of an interconnecting lead 706 in electrical communication with the microelectrode element 700.

Figure 31A:
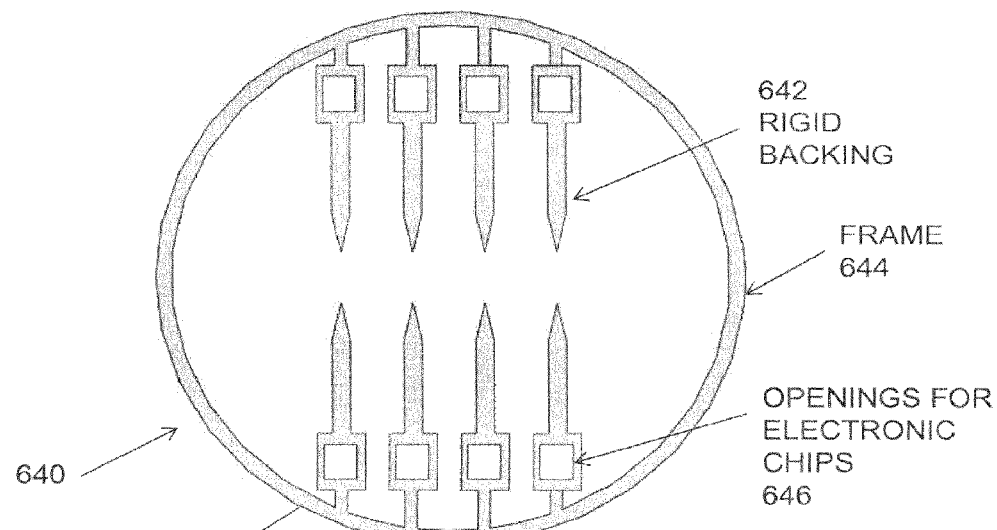
FIG. 31A is a planar view of a construction element of an embodiment of a microelectrode tip.
Figure 31B:
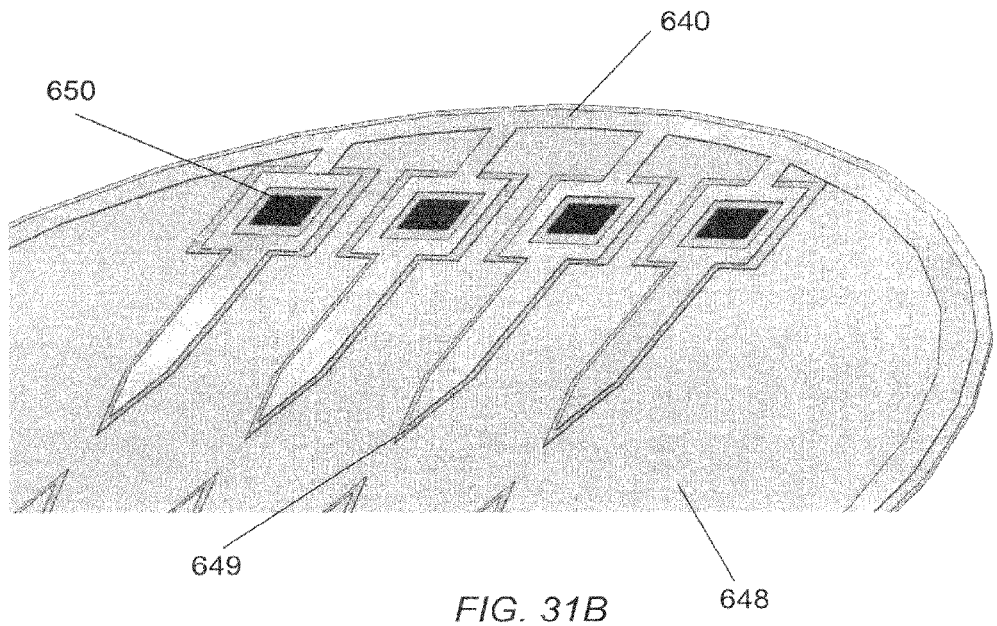
FIG. 31B is a schematic view of a portion of the construction element illustrated in FIG. 31A.

FIG. 31A is a planar view of a construction element of an embodiment of a microelectrode tip. The construction element includes a stencil frame tree 640 including eight rigid backing members 642 releasably attached to a supporting construction frame 644. Each of the rigid backing members 642 includes an elongated portion, and an proximal portion having an opening 646 to accommodate one or more electronic devices, when fabricated. The stencil frame tree 640 can be implemented in a rigid material, such that each of the individual supporting construction frames can be bonded to the devices on the carrier wafer.

Figure 31C:
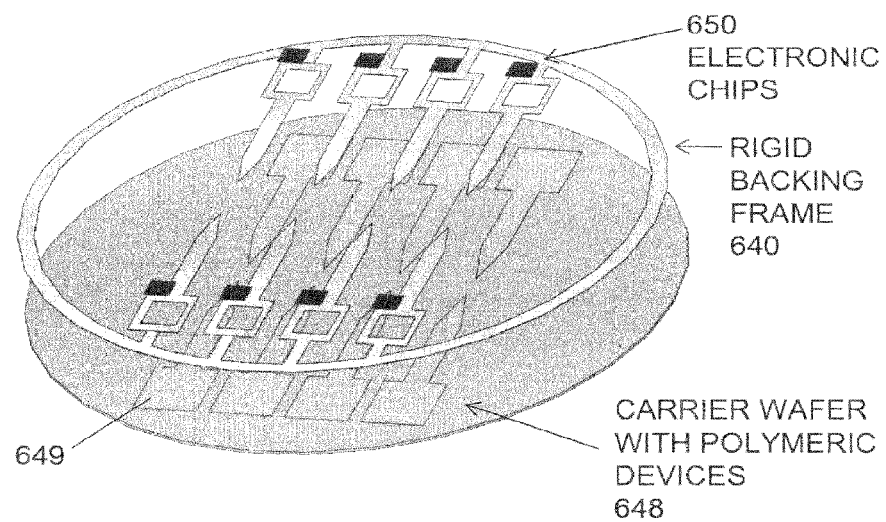
FIG. 31C is an exploded schematic view of a construction element of an embodiment of a microelectrode tip.
Figure 31D:
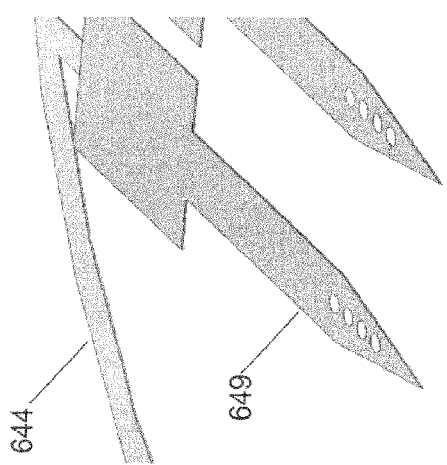
FIG. 31D is a schematic view of another portion of the construction element illustrated in FIG. 31B.

FIG. 31C illustrates an exploded schematic view of a construction element of an embodiment of a microelectrode array tip. The stencil frame tree 400 is placed on a surface of a carrier wafer including micro-array devices 649 formed therein. The stencil frame tree 400 is suitably aligned with the micro-array devices 649 of the carrier wafer 648, and bonded thereto. One or more electronic devices can be suitably placed on the polymer devices either after or before the stencil frame tree 400 is bonded to the carrier wafer 648.

FIG. 31B is a schematic view of a portion of the construction element illustrated in FIG. 31C, illustrating a close up of the assembled components. In this exemplary embodiment, the polymer devices were fabricated using a "backside" electrodes process.

FIG. 31D is a schematic view of another portion of the construction element illustrated in FIG. 31B. Once the sacrificial layer has been removed as described above in relation to FIG. 29, the devices 649 are released from the carrier wafer 648 and are now bonded to the stencil 640 for support. In the exemplary embodiment, the side of the polymeric device 649 facing the carrier wafer 648 (and in contact with the sacrificial layer) has the microelectrodes at its surface. In general, microelectrodes may be included in either or both sides as described herein.

In some embodiments, a rigid back 642 (FIG. 31A) on the polymer micro-device 649 is required. This renders the device 649 fully, or locally, rigid. This rigidity might be advantageous for insertion into tissue. The concept is a stencil shape 640 which can be bonded onto the devices on the carrier wafer where they have been fabricated. The stencil shape 640 can be implemented in a polymer, such as PEEK or Polyurethane, or in metal such as Medical Grade Stainless Steel or Titanium. It can be molded into shape, cut by machining or laser, or stamped out. When this rigid structure has been attached to the devices, the electronic chip can be bonded. The electronic chip can also be bonded to the devices beforehand. After the assembly process the devices can be removed from the carrier wafer using the same sacrificial etching techniques as described above. A further assembly procedure can be to remove the rigid backing from its frame and integrate the device with its final structure. In some embodiments, the rigid backing is conductive. In other embodiments, the rigid backing is non-conductive. When this support structure is of a conductive material, it can also serve as the electrical ground or reference for the stimulation.

Electronic Components

The electronic components of the device enable: (i) recording of neural activity from the microelectrode array to identify which microelectrode sites are closest to the stimulation region of interest; and (ii) stimulation and modulation of neuronal activity with the microelectrode array and the ability to select which microelectrode sites stimulating.

The electronics can be implemented using discrete components, integrated circuit technology, or a combination of both. A black box design of the electronics is shown below. The electronics can be driven by an existing Implantable Pulse Generator (IPG), but will include a telemetric programming interface to properly condition or route the signal from the IPG to the microelectrode array. An embodiment of the electronic components exists which does not require the IPG.

Mechanical Components

The mechanical components and associated assembly processes serve to house the device in a hermetic and biocompatible manner. They also enable connection to an existing Implantable Pulse Generator or the extra-corporeal control unit. The extra-corporeal unit provides power, programming ability and retrieval of information. It can be implanted much like the external cochlear stimulation systems that exist today. In an embodiment that includes an Implantable Pulse Generator, it would serve to retrieve information and program the electrical unit to route the signals from the IPG to the microelectrode array.

Figure 33:
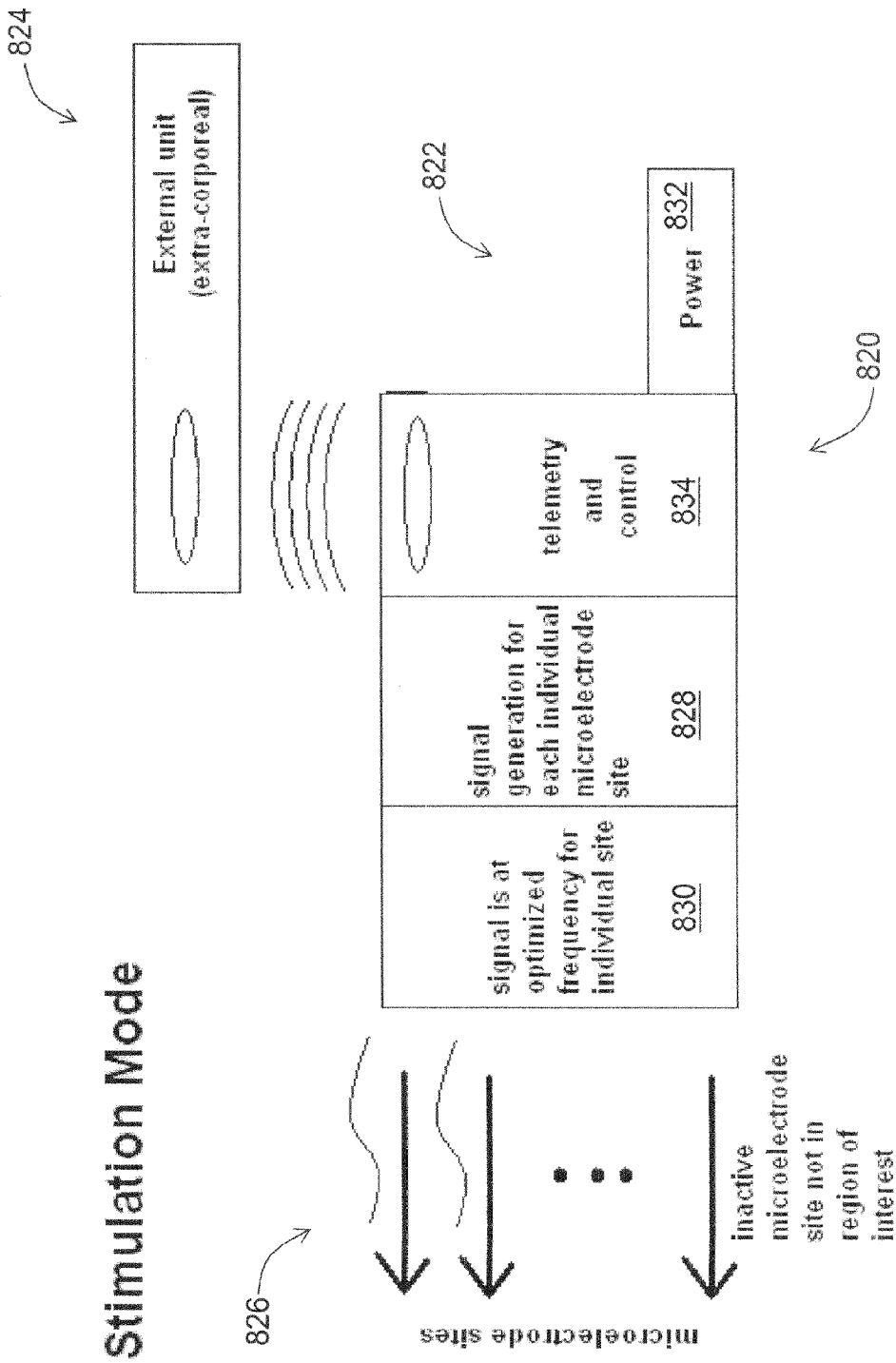
FIG. 33 is a functional block diagram of an exemplary embodiment of a neurological microelectrode system configured in stimulation mode.
Figure 34:
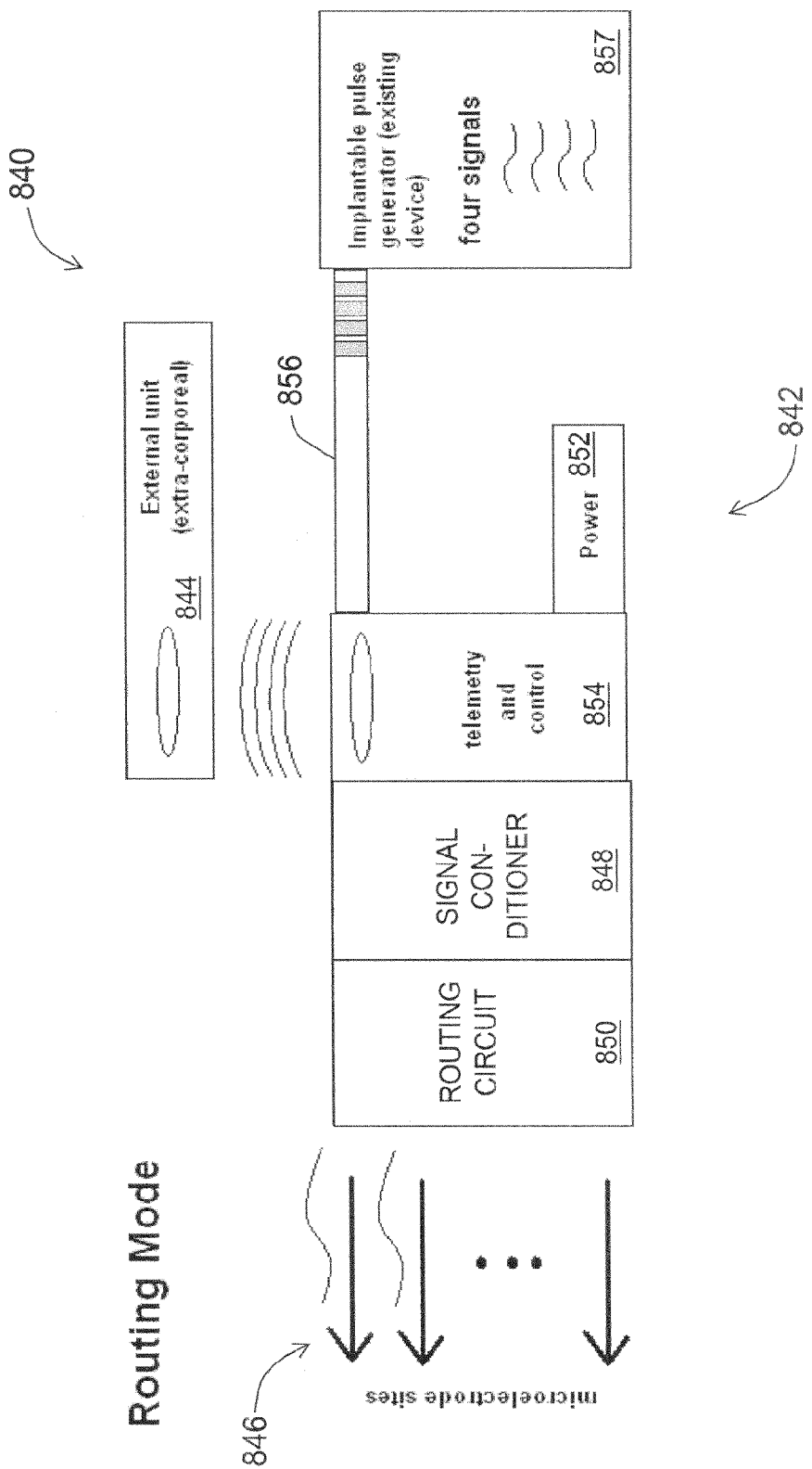
FIG. 34 is a functional block diagram of an exemplary embodiment of a neurological microelectrode system configured in routing mode.

Referring to FIG. 33, a functional block diagram of an exemplary embodiment of a neurological target stimulator 820 configured in a stimulation mode. The stimulator 820 includes an implantable portion 822 including a microelectrode array 826 positionable at a neurological target. The implantable portion 822 also includes a signal generation device 828 for actively stimulating the neurological target. In some embodiments, each of the one or more microelectrodes of the microelectrode array 826 is in communication with a dedicated signal generation device 828. The respective stimulation signal provided at an optimized frequency for each individual microelectrode-tissue interface, based on a peak resistance frequency. The implantable portion 822 can include a power source 832, such as a battery. In some embodiments, the implantable portion 822 also includes a telemetry and control module 834 configured for external communication with an extra-corporeal unit 824. Such a feature can be used to provide extra-corporeal control for operating the implantable portion 822.

Referring to FIG. 33, a functional block diagram of another exemplary embodiment of a neurological target stimulator 840 is illustrated configured in so-called routing mode. The stimulator 840 includes an implantable portion 842 including a microelectrode array 846 positionable at a neurological target. The implantable portion 842 also includes a signal routing circuit 850 configured to direct a stimulation signal to one or more of the microelectrodes 846 for actively stimulating the neurological target. In this embodiment, the stimulation signal is obtained from a separate, implantable pulse generator 857. The pulse generator 857 is in communication with the implantable portion 842 through an interconnection cable 856 containing one or more signal leads. The implantable portion 842 also includes at least one signal conditioner 848 configured to condition an output signal from the pulse generator 857 suitable for stimulation of the neurological target through one or more of the microelectrodes 846. The implantable portion 232 generally includes a power source 852, such as a battery. In some embodiments, the implantable portion 842 also includes a telemetry and control module 854 configured to communicate with an extra-corporeal unit 844, to provide controls for operating the implantable portion 842.

Filtering of an Existing Signal

In some embodiments, the signal conditioner 848 include a filtering circuit to pre-filter or gain adjust (e.g., pre-amplify and/or attenuate) or otherwise condition an existing signal before routing it to a microelectrode array. Several popular filter options include digital filters, such as infinite impulse response (IIR) filters, electronic filters using one or more electrical components, such as inductors and capacitors, and surface acoustic wave (SAW) devices. The filters can be designed through well known filter synthesis techniques to have a preferred performance features. Some of the controllable features in filter synthesis include filtration bandwidth, corner frequency, pass-band ripple, and relative sideband level. Such filters include categories referred to as Butterworth, Chebyshev 1 and 2, and Elliptic filters. The particular implementation—whether analog or digital, passive or active, makes little difference as the output from any implementation would still match the desired output.

Figure 35:
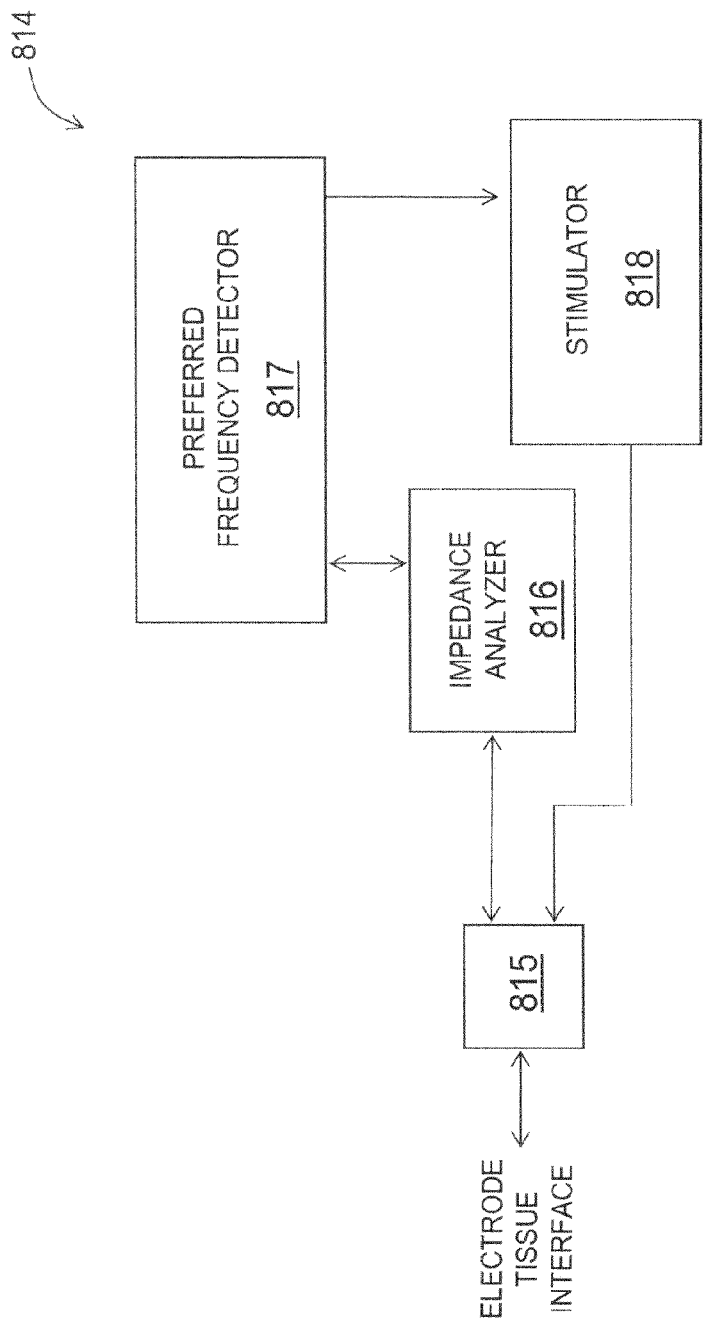
FIG. 35 is a functional block diagram of another embodiment of a neurological microelectrode system.

FIG. 35 is a functional block diagram of another embodiment of a neurological microelectrode target stimulator 814 is shown. The stimulator 814 includes a microelectrode array 815 positionable at a neurological target of interest. The stimulator 814 also includes an impedance analyzer 816 configured for measuring an electrical impedance, a preferred frequency detector 817, and a stimulator 818 for electrically stimulating the neurological target.

The impedance analyzer 816 can use any of various known techniques for measuring electrical impedance. Generally, the impedance analyzer 816 provides a test electrical signal having known or measurable attributes to the microelectrode-tissue interface. Such attributes include a voltage level of a voltage source, or a current level of a current source. The test voltage or current, as the case may be, when applied to the microelectrode-tissue interface, induces a sensed current or voltage according to physical properties of the microelectrode-tissue interface. The impedance analyzer 816 can form a ratio of the test signal to the sensed signal, yielding an impedance value according to Ohm's Law: $Z=V/I$. As the microelectrode-tissue impedance $Z$ is a complex quantity, each of the test and sensed electrical signals is identified as having both a magnitude and a phase.

In operation, the impedance analyzer measures a complex impedance of the microelectrode-tissue interface surrounding the at least one microelectrode 815. The impedance analyzer repeats the measurements at multiple different frequencies, by varying frequency of the applied test electrical signal. Preferably, the multiple frequencies span a frequency range that includes biologically relevant frequencies. The preferred frequency detector 817 identifies the measured impedance being closest to a pure resistance. Such a determination can be accomplished by identifying the measured impedance value having a phase value closest to zero. For example, a measured impedance can be identified having minimum absolute value phase (i.e., $MIN|\angle Z|$). Such a determination can also be accomplished by identifying the measured impedance value having a minimum reactance (i.e., $MIN(Im\{Z\})$). The frequency at which the impedance determined to be closest to a pure resistance is identified as a preferred stimulation frequency. The stimulator 818 is then adjusted to provide a stimulation signal at a frequency, or frequency band, at or near the preferred stimulation frequency. The stimulation signal is then applied to the microelectrode array 815.

Figure 36:
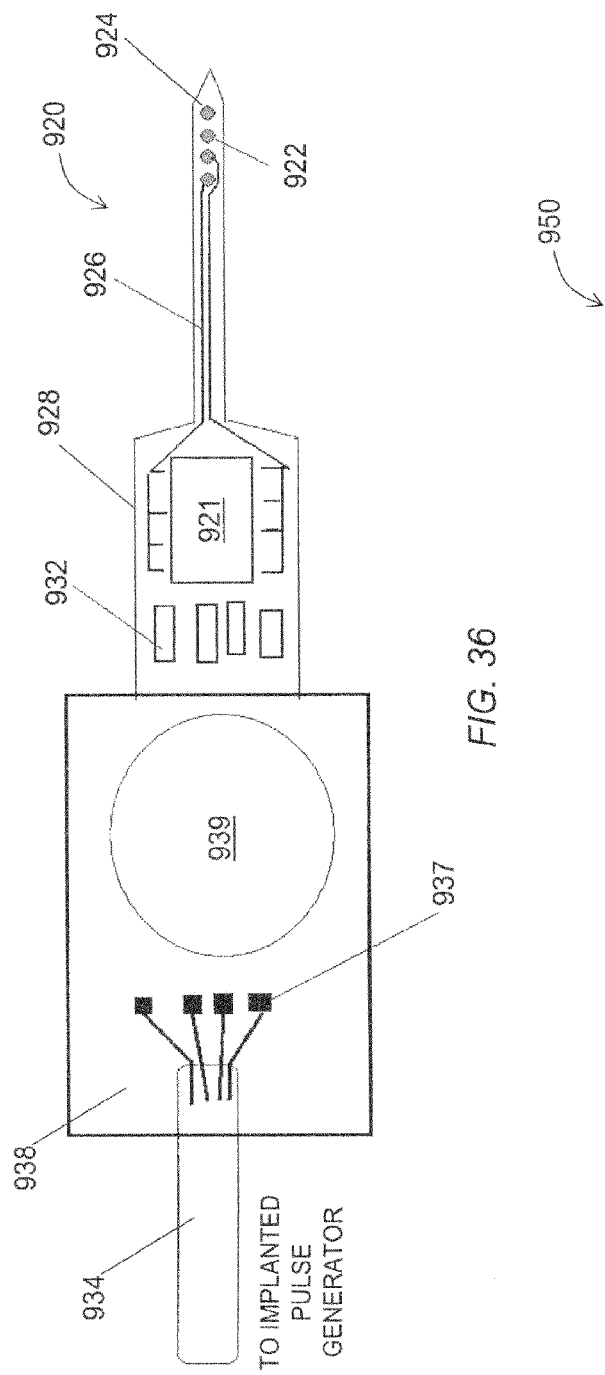
FIG. 36 is a schematic view of an embodiment of a neurological target stimulator.

A top view of an exemplary embodiment of a microelectrode assembly 920 is illustrated in FIG. 36. The assembly 920 includes an array of microelectrodes 922 positioned along a distal end of an elongated probe substrate 924. A first electronic assembly 928 is positioned at a proximal end of the elongated probe substrate 924. The first electronic assembly 928 can include one or more integrated circuit elements 921, such as a microprocessor, and one or more discrete electronic components 932. The first electronic assembly 928 is interconnected to each of the microelectrodes 922 through a respective trace 926 running along the elongated probe substrate 924. The electronic assembly 928 and can be configured to implement one or more functions of the implantable neurological stimulator described herein. In some embodiments, the elongated probe substrate also includes at least a portion of the electronic assembly 928.

In some embodiments, the first electronic circuitry 928 is connected to an implanted pulse generator (not shown) through a cable 924. In some embodiments, as shown, a second electronics assembly (or a portion of the first electronics assembly) includes telemetry circuitry 939, such as a telemetry antenna. In the exemplary embodiment, at least a portion of electronic circuitry 928, 938 is positioned adjacent to the microelectrodes 922, for example being joined by the elongated probe substrate 924.

The mechanical components and associated assembly processes serve to house the assembly 920 in a hermetic and biocompatible manner. They may also enable connection to an existing Implantable Pulse Generator or the extra-corporeal control unit. The extra-corporeal unit can provide power, programming ability, and retrieval of information. In some embodiments, the assembly 920 can be implanted much like currently available external cochlear stimulation systems. In an embodiment that includes an implantable pulse generator, it would serve to retrieve information and program the electrical unit to route the signals from the implantable pulse generator to the microelectrode array 922.

The device provides highly localized and efficient stimulation by incorporating microfabricated components, electronic components and mechanical components. The microfabricated component consists of a microelectrode array. This array can be implemented in a polymeric material such as polyimide, polyurethane, parylene, or polysiloxane (silicone) and includes thin film or plated layers of a metal or metal oxide with high charge transfer capability such as platinum, platinum-iridium, iridium, iridium oxide or titanium. The polymeric and metallic layers can be deposited sequentially and formed using established principles of microfabrication such as spin coating, DC/RF sputtering, photolithography, plasma etching, and etching with a mask consisting of a secondary or sacrificial material such as silicon dioxide or photosensitive resist. The metallic layer can be formed to create the microelectrode arrays and traces which connect the array to the electronics and housing. The polymeric layers serve to isolate the traces from each other but also provide the structure of the implant's stimulating/recording tip. There are several fabrication methods which can be described to build such a microfabricated component.

The electronic or microelectronic components of the device enable: (i) the ability to identify the peak resistance frequency for each individual microelectrode site using electrical impedance spectroscopy; (ii) stimulate at the characteristic peak resistance frequency of each microelectrode (this guarantees minimized signal distortion and maximum charge transfer to the tissue); and (iii) stimulation and modulation of neuronal activity with the microelectrode array and the ability to select which microelectrode sites are stimulating.

The electronics can be implemented using discrete components, integrated circuit technology, digital signal processing (DSP), or a combination of all three. The electronics can be incorporated in one unit, or can be used in conjunction with an existing implantable pulse generator (IPG). The electronics may include a telemetric programming interface to properly condition or route the signal from the IPG to the microelectrode array.

Figure 37:
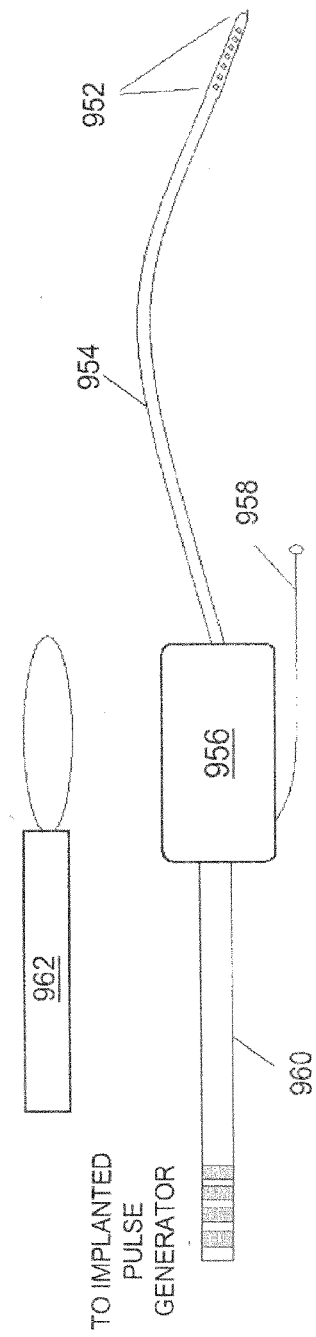
FIG. 37 is a schematic view of an embodiment of a neurological target stimulator system.

Referring to FIG. 37, a side view of an exemplary alternative embodiment of a microelectrode structure is illustrated. In this embodiment, an electronics assembly 956 is positioned remote from the microelectrode array 952. The microelectrode array 952 is joined to the electronics assembly 956 through an arrangement of interconnecting electrical leads 954. The electronics assembly 956 can be configured to implement one or more functions of the implantable neurological stimulator described herein. As illustrated, the electronics assembly 956 can also be connected to an implanted pulse generator (not shown) through an interconnecting cable 960. Alternatively or in addition, the electronics assembly 956 can include telemetry circuitry for communicating with an external telemetry device 962.

The electronics assembly can include an electrical grounding lead for interconnection to an electrical ground potential 958. In any of the embodiments described herein, impedance measurements and/or stimulation can be implemented between two or more microelectrodes (e.g., adjacent microelectrodes). Alternatively or in addition, impedance measurements and/or stimulation can be implemented between one or more microelectrodes and an electrical ground reference.

Note that a device can be assembled to not include electronics. This device would then transfer the signal from the Implantable Pulse Generator directly to the electrodes. A device with electronics would first "pre-filter" the signal before applying to the electronics. This "pre-filter" might take the form of signal filtering in order to achieve a certain signal spectrum, multiplexing and routing in order to direct signals from a pulse generator to a choice of microelectrode sites. The following figures demonstrate the different components and embodiments.

Various exemplary embodiments of microelectrode array element configurations including tetrode arrangements are illustrated in FIG. 38A through FIG. 38D. Referring to FIG. 38A, a microelectrode array element 1000 includes a stimulation electrode 1002 and four recording electrodes 1004. In the exemplary embodiment, the stimulation electrode 1002 is disc-shaped; however, other shapes are anticipated, such as polygons, ovals, and irregular shapes. In this embodiment, the recording electrodes 1004 are substantially smaller than the stimulation electrode 1002, and positioned within the outer perimeter of the stimulation electrode 1002. In order to accommodate this arrangement, the stimulation electrode includes a respective open area 1006, one for each of the recording electrodes. In the exemplary embodiment, the recording electrodes 1004 are uniformly spaced having about 90° angular separation between adjacent pairs.

In general, the open areas 1006 can have any shape, and the shape need not be the same as the shape of any recording electrode 1004 that may be positioned therein. In the exemplary embodiments, the open areas 1006 do have a similar shape, namely a circle, as the disc-shaped recording electrodes 1004. The openings are dimensioned larger than the recording electrodes 1004, such that the recording electrodes can be placed within the open areas 1006, without touching the stimulation electrode 1002. An annular region of separation exists between the two electrodes 1002, 1004. The recording electrodes 1004 may each be similarly shaped and/or similarly sized with respect to each other. They may have similar shape as the stimulation electrode 1002, or have a different shape. In some embodiments, at least some of the recording electrodes 1004 have different shapes and/or different sizes with respect to each other.

In the exemplary embodiment, the four disc electrodes 1004 embedded within the larger, stimulation electrode 1002. The recording electrodes 1004 each have a respective diameter of about 50 μm, and a relative separation to their nearest neighbors of about 150 μm. The stimulation electrode has a diameter of 300 μm. In some embodiments, the diameter of each recording electrode can range between about 2 μm or less, and about 300 μm or more. In some embodiments, the diameter of the stimulation electrode can range between about 5 μm or less, and about 1,000 μm or more.

Referring to FIG. 38B, an alternative embodiment of a microelectrode array element 1010 shows a stimulation electrode 1012 as a non-closed disc. The outer perimeter of the stimulation electrode 1012 generally follows a circular arc, with indentations defining open areas 1016 extending in from the perimeter, towards the center of the electrode 1012. In particular, four such open areas 1016, or slots, each accommodate a respective recording electrode 1014. The recording electrode 1014 is positioned toward an inner end of the open area 1016, nearest the center of the stimulation electrode 1012. In at least some embodiments, the recording electrode 1014 is spaced apart from a perimeter of the open area 1016, such that the recording electrode 1014 does not touch the stimulation electrode 1012. In some embodiments, the perimeter of the stimulation electrode 1012 are generally rounded, without sharp corners, in order to prevent highly localized fields. Although a four-recording electrode embodiment is shown, other embodiments are possible including one or more recording electrodes positioned within respective open areas 1016. Although circular shapes are illustrated for each of the stimulation electrode and the recording electrode, different shapes can be used. The shapes can be regular, such as ellipses, polygons, and irregular shapes.

Referring to FIG. 38C, illustrates a similar embodiment of a microelectrode array element 1020 to that described above, except that two tetrodes 1024a, and 1024b are embedded within the same stimulation electrode 1022. The two tetrodes 1024a, 1024b can record neural activity from different tissue volumes sizes, with different sensitivities to neural activity. The "inner tetrode" 1024b can have the same, or different microelectrode diameters than the "outer tetrode" 1024a. The diagram shows an "inner tetrode" with 50 μm discs, and an "outer tetrode" with 60 μm discs. Other shapes, sizes, and numbers of tetrode elements are possible.

Referring to another microelectrode element embodiment 1030 illustrated in FIG. 38D, a tetrode 1034 is only slightly embedded into the stimulation electrode 1032. As shown, the innermost portion of the open area 1036 is spaced apart from an outer perimeter of the stimulation electrode 1032 by a distance less than a diameter of the recording element 1034. Such a configuration would allow adjustment and optimization of the sensitivity and volume of tissue being recorded.

Various embodiments of neurological stimulation devices and techniques have been described herein. These embodiments are given by way of example and are not intended to limit the scope of the present invention. It should be appreciated, moreover, that the various features of the embodiments that have been described may be combined in various ways to produce numerous additional embodiments.

One or more of any of the microelectrode array elements 1000, 1010, 1020, 1030 described above can be positioned on an elongated cylindrical member, forming a microelectrode array. Alternatively or in addition, one or more of any of the microelectrode array elements 1000, 1010, 1020, 1030 described above can be positioned on an elongated planar member, also forming a microelectrode array. An exemplary planar probe extension 1040 is illustrated in FIG. 39A. The probe extension 1040 includes four microelectrode elements 1045. Each of the microelectrode elements 1045 includes a respective stimulation electrode 1042 and tetrode arrangement of recording electrodes 1044. In the illustrative embodiment, discoid tetrode elements 1044 are disposed along an external perimeter of a discoid stimulation electrode 1042, such that the tetrode elements 1044 are spaced apart from the outer perimeter of the stimulation electrode 1042.

Another alternative embodiment of a planar probe extension 1050 is illustrated in FIG. 39 In this embodiment, each of the a probe extension 1050 includes four microelectrode elements 1055. Each of the microelectrode elements 1055 includes a respective stimulation electrode 1052 and tetrode arrangement of recording electrodes 1054. In the illustrative embodiment, discoid tetrode elements 1054 are disposed within an open interior region of an annular stimulation electrode 1052, such that the tetrode elements 1054 are spaced apart from the inner annular perimeter of the stimulation electrode 1052.

Various embodiments of micro-fabricated neurostimulation devices have been described herein. These embodiments are giving by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

Although some devices described herein are identified as either cutaneous or chronic, it is understood that such cutaneous devices may be used in chronically, being implanted for extended periods, or even indefinitely. Similarly, any devices described herein as being chronic, it is understood that such devices may also be used cutaneously.

While this invention has been particularly shown and described with references to preferred embodiments thereof, it will be understood by those skilled in the art that various changes in form and details may be made therein without departing from the scope of the invention encompassed by the appended claims.

What is claimed:

1. An implantable neurological device, comprising:
a support tube;
a cylindrical member having a distal end, a proximal end, and an internal lumen; and
a microelectrode film attached to an outer surface of the support tube to form a cylindrical substrate and with the support tube defining a lumen of the cylindrical substrate, the microelectrode film comprising a plurality of microelectrode elements, a longitudinal extension extending from a distal end of the microelectrode film, and a proximal end, the distal end of the microelectrode film disposed toward the distal end of the cylindrical member, a portion of the longitudinal extension extending in the internal lumen of the cylindrical member toward the proximal end of the cylindrical member.

2. The device of claim 1, the microelectrode film comprising:
a first insulative layer;
a plurality of lead contacts;
a plurality of conductive traces to couple the plurality of lead contacts to the plurality of microelectrode elements; and
a second insulative layer disposed on the plurality of conductive traces and the first insulative layer.

3. The device of claim 1, wherein each of the plurality of microelectrode elements are individually addressable.

4. The device of claim 1, comprising:
an electronic component electrically coupled between the plurality of microelectrode elements and a plurality of lead contacts disposed on the longitudinal extension of the microelectrode film.

5. The device of claim 4, comprising:
the electronic component including a router to selectively couple the plurality of microelectrode elements with the plurality of lead contacts disposed on the longitudinal extension of the microelectrode film.

6. The device of claim 1, comprising:
at least one of the plurality of microelectrode elements shaped substantially different from another microelectrode element of the plurality of microelectrode elements.

7. The device of claim 1, the plurality of microelectrode elements comprising at least one circumferential electrode.

8. The device of claim 1, the plurality of microelectrode elements comprising at least one segmented electrode.

9. The device of claim 1, comprising:
the plurality of microelectrode elements configured as a micro-electromechanical system (MEMS).

10. The device of claim 1, comprising:
one or more of the plurality of microelectrode elements including a recording element; and
one or more of the plurality of microelectrode elements including a stimulating element.

11. An implantable neurological device, comprising:
a support tube;
a microelectrode film attached to an outer surface of the support tube to form a cylindrical substrate, the support tube defining a lumen of the cylindrical substrate, the microelectrode film comprising:
one or more microelectrode elements; and
an extension, a portion of the extension extending into the lumen defined by the cylindrical substrate.

12. The device of claim 11, wherein the extension extends from a distal end of the microelectrode film into the lumen defined by the cylindrical substrate.

13. The device of claim 11, wherein the extension extends radially from the microelectrode film into the lumen defined by the cylindrical substrate.

14. The device of claim 11, the microelectrode film comprising:
a first insulative layer;
a plurality of lead contacts;
a plurality of conductive traces to couple the plurality of lead contacts to the one or more microelectrode elements; and
a second insulative layer disposed on the plurality of conductive traces and the first insulative layer.

15. The device of claim 14, comprising:
an electronic component electrically coupled between the one or more microelectrode elements and a plurality of lead contacts.

16. The device of claim 15, comprising:
a router to couple the one or more microelectrode elements with the plurality of lead contacts.

17. The device of claim 11, comprising:
at least one circumferential electrode.

18. The device of claim 11, comprising:
at least one segmented electrode.

19. The device of claim 11, comprising:
one or more microelectrode elements configured as a micro-electromechanical system (MEMS).

20. A method of forming an implantable neurological device, comprising:
providing a support tube;
providing a microelectrode film comprising a plurality of microelectrode elements, a longitudinal extension extending from a distal end of the microelectrode film, and a proximal end;
shaping the microelectrode film to form a cylindrical shape;
attaching the microelectrode film with an outer surface of the support tube such that the support tube defines a lumen through the cylindrical shape; and
inserting the longitudinal extension into the lumen.

21. The method of claim 20, comprising:
shaping the microelectrode film by heating the microelectrode film.

* * * * *